United States Patent
Oh et al.

(10) Patent No.: US 12,144,245 B2
(45) Date of Patent: Nov. 12, 2024

(54) COMPOUND FOR AN ORGANIC ELECTRIC ELEMENT, AN ORGANIC ELECTRIC ELEMENT USING THE SAME, AND AN ELECTRONIC DEVICE THEREOF

(71) Applicant: DUK SAN NEOLUX CO., LTD., Cheonan-si (KR)

(72) Inventors: Hyun Ji Oh, Cheonan-si (KR); Soung Yun Mun, Cheonan-si (KR); Sun Hee Lee, Cheonan-si (KR); Hyung Dong Lee, Cheonan-si (KR); Byoung Yeop Kang, Cheonan-si (KR); Ui Sik Kwon, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 725 days.

(21) Appl. No.: 17/304,625

(22) Filed: Jun. 23, 2021

(65) Prior Publication Data

US 2021/0320258 A1     Oct. 14, 2021

Related U.S. Application Data

(63) Continuation-in-part of application No. PCT/KR2019/016421, filed on Nov. 27, 2019.

(30) Foreign Application Priority Data

Dec. 26, 2018   (KR) .................. 10-2018-0169810

(51) Int. Cl.
| | | |
|---|---|---|
| H01L 51/50 | (2006.01) | |
| C07D 407/12 | (2006.01) | |
| C07D 411/12 | (2006.01) | |
| C07D 411/14 | (2006.01) | |
| H10K 85/60 | (2023.01) | |

(Continued)

(52) U.S. Cl.
CPC ......... *H10K 85/636* (2023.02); *C07D 407/12* (2013.01); *C07D 411/12* (2013.01); *C07D 411/14* (2013.01); *H10K 50/11* (2023.02); *H10K 50/15* (2023.02); *H10K 50/16* (2023.02); *H10K 50/17* (2023.02); *H10K 50/171* (2023.02); *H10K 85/657* (2023.02); *H10K 85/6574* (2023.02); *H10K 85/6576* (2023.02)

(58) Field of Classification Search
None
See application file for complete search history.

(56) References Cited

U.S. PATENT DOCUMENTS

2012/0018717 A1* 1/2012 Kim .................. C07D 209/94
                                                  546/276.7

FOREIGN PATENT DOCUMENTS

KR    10-2009-0041040 A    4/2009
KR    10-1120892 B1        2/2012
(Continued)

*Primary Examiner* — Gregory D Clark
(74) *Attorney, Agent, or Firm* — Vorys, Sater, Seymour and Pease LLP; Mih Suhn Koh

(57) ABSTRACT

Provided are compound represented by Formula 1, an organic electric element including a first electrode, a second electrode, and an organic material layer formed between the first electrode and the second electrode, and electronic device thereof, and by including the compound represented by Formula 1 in the organic material layer, the driving voltage of the organic electric element can be lowered, and the luminous efficiency and life time of the organic electric element can be improved.

9 Claims, 1 Drawing Sheet

(51) Int. Cl.
    *H10K 50/11*           (2023.01)
    *H10K 50/15*           (2023.01)
    *H10K 50/16*           (2023.01)
    *H10K 50/17*           (2023.01)

(56) References Cited

FOREIGN PATENT DOCUMENTS

| KR | 10-2014-0134884 A | | 11/2014 |
|---|---|---|---|
| KR | 10-2015-0077263 A | | 7/2015 |
| KR | 10-2015-0079911 A | | 7/2015 |
| KR | 2015-0077263 | * | 7/2015 |
| KR | 10-2018-0006763 A | | 1/2018 |

* cited by examiner

COMPOUND FOR AN ORGANIC ELECTRIC ELEMENT, AN ORGANIC ELECTRIC ELEMENT USING THE SAME, AND AN ELECTRONIC DEVICE THEREOF

CROSS-REFERENCE TO RELATED APPLICATION

This patent application is a Continuation-in-Part of International PCT Application No.: PCT/KR2019/016421, filed on Nov. 27, 2019, and claims priority from and the benefit under 35 U.S.C. § 119 to § 121, and § 365 of Korean Patent Application No. 10-2018-0169810, filed on Dec. 26, 2018 which is hereby incorporated by reference for all purposes as if fully set forth herein. Further, this application claims the benefit of priority in countries other than U.S., which is hereby incorporated by reference herein.

BACKGROUND

Technical Field

The present invention relates to compound for an organic electric element, an organic electric element comprising the same, and an electronic device thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

The most important issues in organic electroluminescent element are life and efficiency, and as the display becomes larger, these efficiency and life problems must be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase.

However, efficiency cannot be maximized only by simply improving the organic material layer. This is because long life span and high efficiency can be simultaneously achieved when energy levels and T1 values among the respective layers included in the organic material layer, inherent material properties (mobility, interfacial properties, etc.) and the like are optimal combination.

In addition, an emission-auxiliary layer must be present between the hole transport layer and the light emitting layer in order to solve the problem of luminescence in the hole transport layer of recent organic electroluminescent devices, and material of different emission-auxiliary layers have been developed for each of the light emitting layers (R, G, B).

In general, an electron is transferred from an electron transport layer to a light emitting layer and a hole is transferred from a hole transport layer to the light emitting layer, as a result, an exciton is formed by the recombination of the electron and hole. However, the material used for the hole transport layer has a low HOMO value and therefore has a low T1 value. As a result, the exciton generated in the light emitting layer is transferred to the hole transport layer, resulting in a charge unbalance in the light emitting layer and light is emitted at the interface of the hole transport layer.

When light is emitted at the interface of the hole transport layer, the color purity and efficiency of the organic electric element are lowered and a problem occurs in that the life time is shortened. Therefore, it is necessary to develop the emission-auxiliary layer material having a high T1 value and a HOMO level between the hole transport layer and the light emitting layer.

On the other hand, there is a need to develop a hole injection layer material that delays penetration and diffusion of metal oxide from the anode electrode (ITO) into the organic layer, which is one of the causes of shortening the lifespan of organic electric element, and has stable characteristics against Joule heating generated during element driving, that is, a high glass transition temperature. The low glass transition temperature of the hole transport layer material deteriorates the uniformity of the thin film surface during element driving and it is reported that this has a significant effect on the element lifespan. In addition, OLED element are mainly formed by a deposition method, and it is necessary to develop a material that can withstand for long time during deposition, that is, a material with strong heat resistance.

That is, in order to fully exhibit the excellent characteristics of the organic electric element, materials forming the organic material layer in the element, such as a hole injection material, a hole transport material, a light emitting material, an electron transport material, an electron injection material, an emission-auxiliary layer material, etc. should be prerequisite to support by a stable and efficient material. However, the stable and efficient material of organic material layer for an organic electric element has not been fully developed yet. Therefore, it is strongly required to develop material for the development of new materials, in particular, material for an emission-auxiliary layer, is continuously required.

Object, Technical Solution and Effects of the Invention

An object of the present invention is to provide compound lowering a driving voltage, improving luminous efficiency and lifetime of the element, an organic electric element comprising the same, and an electronic device thereof.

In an aspect of the present invention, the present invention provides the compound represented by the following formula.

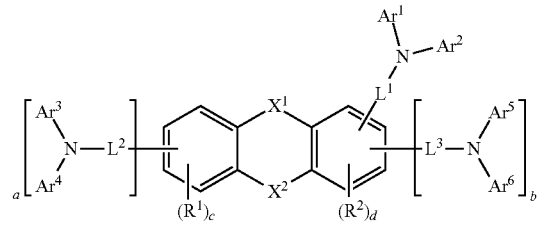

In another aspect of the present invention, the present invention provides an organic electric element employing the compound represented by formula above and an electronic device thereof.

By using the compound according to embodiment of the present invention, a driving voltage of element can be lowered and the luminous efficiency and lifetime of the element can be also significantly improved.

DETAILED DESCRIPTION

Figure 1:
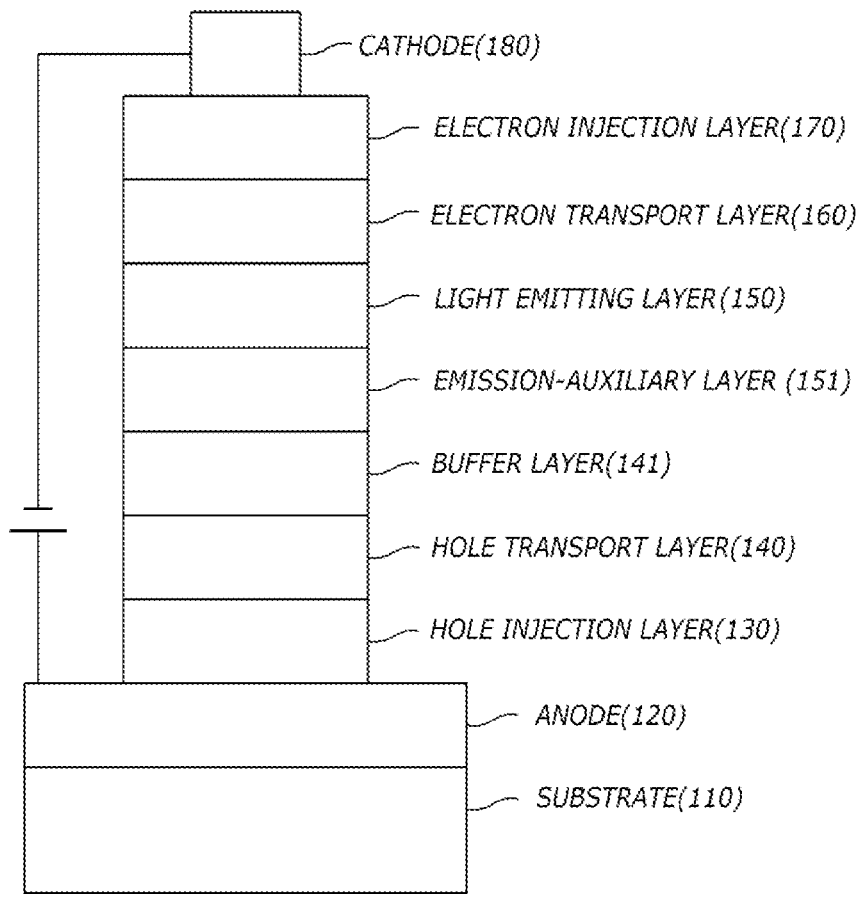
FIG. 1 illustrates an example of an organic electroluminescent element according to the present invention: 100 is an organic electric element, 110 is a substrate, 120 is a first electrode, 130 is a hole injection layer, 140 is a hole transport layer, 141 is a buffer layer, 150 is a light emitting layer, 151 is an emission-auxiliary layer, 160 is an electron transport layer, 170 is an electron injection layer, and 180 is a second electrode.
Figure 2:
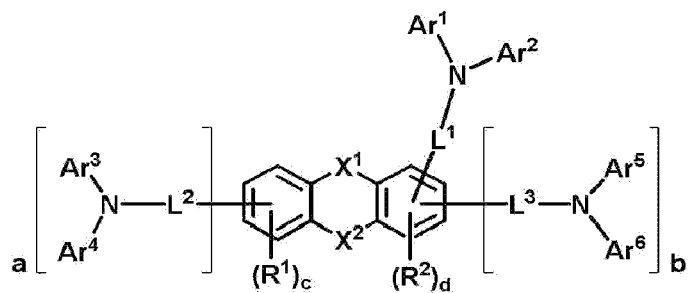
FIG. 2 illustrates Formula according to an aspect of the present invention.

Unless otherwise stated, the term "aryl group" or "arylene group" as used herein has, but not limited to, 6 to 60 carbon atoms. The aryl group or arylene group in the present invention may comprise a monocyclic ring, ring assemblies, a fused polycyclic system, spiro-compounds and the like. In addition, unless otherwise stated, a fluorenyl group may be comprised in an aryl group and a fluorenylene group may be comprised in an arylene group.

Unless otherwise stated, the term "fluorenyl group" or "fluorenylene group" as used herein means univalent or bivalent functional group in which R, R' and R" are all hydrogen in the following structure, "substituted fluorenyl group" or "substituted fluorenylene group" means that at least any one of R, R' and R" is a substituent other than hydrogen, and the case where R and R' are bonded to each other to form the spiro compound together with the carbon bonded to them is comprised.

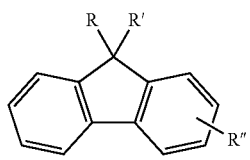

The term "spiro-compound" as used herein has a spiro union which means union having one atom as the only common member of two rings. The common atom is designated as 'spiro atom'. The compounds are defined as 'monospiro-', 'dispiro-' or 'trispiro' depending on the number of spiro atoms in one compound.

The term "heterocyclic group" used in the specification comprises a non-aromatic ring as well as an aromatic ring like "heteroaryl group" or "heteroarylene group". Unless otherwise stated, the term "heterocyclic group" means, but not limited to, a ring containing one or more heteroatoms and having 2 to 60 carbon atoms. Unless otherwise stated, the term "heteroatom" as used herein refers to N, O, S, P or Si and heterocyclic group means a monocyclic, ring assemblies, a fused polycyclic system or spiro compound containing a heteroatom.

The term "heterocyclic group" used in the specification may comprise compound comprising a heteroatom group such as $SO_2$, $P=O$, etc., as the following compounds, instead of carbon forming a ring.

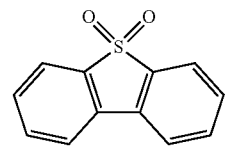 [SMILES: O=S1(=O)c2ccccc2-c2ccccc21]

The term "aliphatic ring group" as used herein refers to a cyclic hydrocarbon except for aromatic hydrocarbons, and comprises a monocyclic ring, ring assemblies, a fused polycyclic system, spiro compounds, and the like, and unless otherwise specified, it means a ring of 3 to 60 carbon atoms, but not limited thereto. For example, a fused ring formed by benzene being an aromatic ring with cyclohexane being a non-aromatic ring corresponds to aliphatic ring group.

In this specification, a 'group name' corresponding to an aryl group, an arylene group, a heterocyclic group, and the like exemplified for each symbol and its substituent may be written in the name of functional group reflecting the valence, and may also be described as the name of a parent compound. For example, in the case of phenanthrene which is a kind of aryl group, it may be described by distinguishing valence such as 'phenanthryl (group)' when it is 'monovalent group', and 'phenanthrylene (group)' when it is 'divalent group', and regardless of its valence, it may also be described as 'phenanthrene' which is a parent compound name. Similarly, in the case of pyrimidine, it may be described as 'pyrimidine' regardless of its valence, and it may also be described as the name of corresponding functional group such as pyrimidinyl (group) when it is 'monovalent group', and 'pyrimidinylene (group)' when it is 'divalent group'.

In addition, in the present specification, the numbers and alphabets indicating a position may be omitted when describing a compound name or a substituent name, For example, pyrido[4,3-d]pyrimidine, benzopuro[2,3-d]pyrimidine and 9,9-dimethyl-9H-fluorene can be described as pyridopyrimidine, benzofurropyrimidine and dimethylfluorene, respectively. Therefore, both benzo[g]quinoxaline and benzo[f]quinoxaline can be described as benzoquinoxaline.

In addition, unless otherwise expressed, where any formula of the present invention is represented by the following formula, the substituent according to the index may be defined as follows.

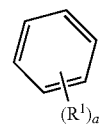

In the above formula, where a is an integer of zero, the substituent $R^1$ is absent, that is, hydrogen atoms are bonded to all the carbon constituting the benzene ring. Here, chemical formulas or compounds may be written described by omitting the indication of hydrogen bonded to carbon. In addition, one substituent $R^1$ is bonded to any carbon of the carbons forming the benzene ring when "a" is an integer of 1. Similarly, where "a" is an integer of 2 or 3, for example, as in the following formulas, substituents $R^1$s may be bonded to the carbon of the benzene ring. Also, where "a" is an integer of 4 to 6, substituents $R^1$s are bonded to the carbon of the benzene ring in a similar manner. Further, where "a" is an integer of 2 or more, $R^1$s may be the same or different from each other.

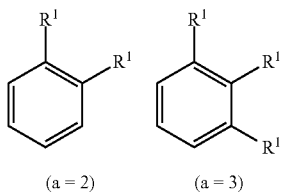

(a = 2)   (a = 3)

In addition, unless otherwise specified in the present specification, the ring formed by bonding between adjacent groups may be selected from the group consisting of a $C_6$-$C_{60}$ aromatic ring group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring of a $C_3$-$C_{60}$ aliphatic ring with a $C_6$-$C_{60}$ aromatic ring group and a combination thereof.

Hereinafter, a laminated structure of the organic electric element comprising the compound of the present invention will be described with reference to FIG. 1.

In the following description of the present invention, a detailed description of known configurations and functions incorporated herein will be omitted when it may make the subject matter of the present invention rather unclear.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

FIG. 1 illustrates an example of an organic electric element according to an embodiment of the present invention.

Referring to the FIG. 1, an organic electric element 100 according to an embodiment of the present invention includes a first electrode 120 formed on a substrate 110, a second electrode 180, and an organic material layer formed between the first electrode 120 and the second electrode 180 and comprising the compound of the present invention. Here, the first electrode 120 may be an anode (positive electrode), and the second electrode 180 may be a cathode (negative electrode). In the case of an inverted organic electroluminescent element, the first electrode may be a cathode, and the second electrode may be an anode.

The organic material layer may include a hole injection layer 130, a hole transport layer 140, a light emitting layer 150, an electron transport layer 160, and an electron injection layer 170 stacked in sequence on the first electrode 120. Here, at least one layer of the organic material layer may be omitted, or a hole blocking layer, an electron blocking layer, an emission-auxiliary layer 151, an electron transport-auxiliary layer, a buffer layer 141, etc. may be further included in the organic material layer, and the electron transport layer 160 or the like may serve as a hole blocking layer.

In addition, although not shown, the organic electric element according to an embodiment of the present invention may further include a protective layer or a layer for improving luminous efficiency. The layer for improving luminous efficiency may be formed on one side of sides of the first electrode or one side of sides of the second electrode, wherein the one side is not facing the organic material layer.

The inventive compound employed in the organic material layer may be used as a material of a hole injection layer 130, a hole transport layer 140, an emission-auxiliary layer 151, an electron transport-auxiliary layer, an electron transport layer 160 or an electron injection layer 170, as host or dopant of a light emitting layer 150, or as a material of a layer for improving luminous efficiency. Preferably, compound of Formula 1 of the present invention can be used as material of an emission-auxiliary layer 151.

On the other hand, even if the core is same or similar, the band gap, the electrical characteristics, the interface characteristics and the like may be different depending on which substituent is bonded at which position. Therefore, there is a need to study the selection of the core and the combination of the core and the sub-substituent bonded to the core. In particular, long life span and high efficiency can be simultaneously achieved when the optimal combination of energy levels and $T_1$ values, inherent material properties (mobility, interfacial properties, etc.) and the like among the respective layers of an organic material layer is achieved.

Therefore, the energy level and $T_1$ value between the respective layers of the organic material layer, inherent material properties (mobility, interfacial properties, etc.) and the like can be optimized by using compound of Formula 1 as material of an emission-auxiliary layer 151.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or alloy on the substrate to form the anode 120, forming the organic material layer including the hole injection layer 130, the hole transport layer 140, the light emitting layer 150, the electron transport layer 160, and the electron injection layer 170 thereon, and then depositing a material which can be used as the cathode 180, thereon. In addition, an emitting auxiliary layer 151 may be formed between a hole transport layer 140 and a light emitting layer 150, and an electron transport-auxiliary layer may be formed between a light emitting layer 150 and an electron transport layer 160.

In addition, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

In addition, the organic electric element according to the present invention may be selected from group consisting of an organic electroluminescent element, an organic solar cell, an organic photo conductor, an organic transistor, an element for monochromatic illumination and an element quantum dot display.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electric dictionary, a point-to-multipoint (PMP), a remote controller, a navigation unit, a game player, various kinds of TVs, various kinds of computers and so on.

Hereinafter, compound according to an aspect of the present invention will be described.

The compound according to an aspect of the present invention is represented by Formula 1 below.

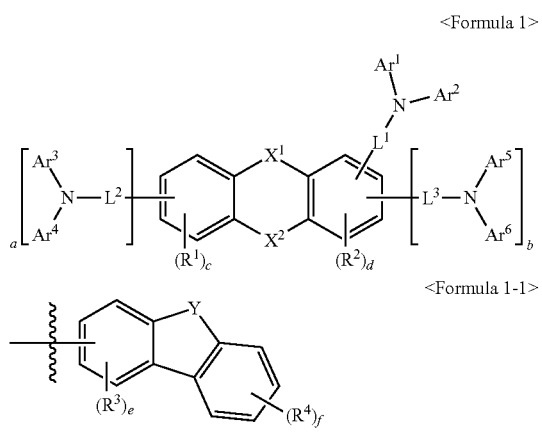

<Formula 1>

<Formula 1-1>

In Formula 1, each of symbols may be defined as follows.

$X^1$ and $X^2$ are each independently O or S.

a and b are each an integer of 0 or 1 and at least one of a and b is 1.

$Ar^1$ to $Ar^6$ are each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a $C_1$-$C_{60}$ alkyl group, a $C_2$-$C_{20}$ alkenyl group, a $C_2$-$C_{20}$ alkynyl group, a $C_1$-$C_{30}$ alkoxyl group and a $C_6$-$C_{30}$ aryloxy group, with the proviso that at least one of $Ar^1$ to $Ar^6$ is Formula 1-1. As defined below, in Formula 1-1, Y is C(R')(R"), N(R'), O or S, so that at least one of $Ar^1$ to $Ar^6$ is a fluorenyl group or a heterocyclic group. That is, Formula 1 comprises at least one fluorenyl group, or a heterocyclic group comprising N, O or S.

Where $Ar^1$ to $Ar^6$ are each an aryl group, the aryl group may be preferably a $C_6$-$C_{30}$ aryl group, more preferably a $C_6$-$C_{18}$ aryl group, for example, phenyl, biphenyl, naphthyl, terphenyl, phenanthrene, pyrene and the like.

Where $Ar^1$ to $Ar^6$ are each a heterocyclic group, the heterocyclic group may be preferably a $C_2$-$C_{30}$ heterocyclic group, more preferably a $C_2$-$C_{22}$ heterocyclic group, for example, pyridine, dibenzothiophene, benzonaphthothiophene, dibenzofuran, benzonaphthofuran, carbazole, phenylcarbazole, benzocarbazole, benzophenylcarbazole, quinazoline, indolopyridine, naphthylcarbazole, thianthrene, phenothiazine and the like.

Where $Ar^1$ to $Ar^6$ are each a fluorenyl group, the fluorenyl group may be 9,9-dimethyl-9H-fluorene, 9,9-diphenyl-9H-fluorene, 9,9'-spirobifluorene and the like.

$L^1$ to $L^3$ are each independently selected from the group consisting of a single bond, a $C_6$-$C_{60}$ arylene group, a fluorenylene group, a $C_3$-$C_{60}$ aliphatic ring, a $C_2$-$C_{60}$ heterocyclic group comprising at least one heteroatom selected from the group consisting of O, N, S, Si and P, and a combination thereof.

Where $L^1$ to $L^3$ are each an arylene group, the arylene group may be preferably a $C_6$-$C_{30}$ arylene group, more preferably a $C_6$-$C_{14}$ arylene group, for example, phenylene, biphenyl, naphthalene, phenanthrene and the like.

Where $L^1$ to $L^3$ are each a heterocyclic group, the heterocyclic group may be preferably a $C_2$-$C_{30}$ heterocyclic group, more preferably a $C_2$-$C_{18}$ heterocyclic group, for example, pyridine, quinazoline, quinoline, carbazole, phenylcarbazole, dibenzothiophene, dibenzofuran and the like.

$R^1$ to $R^4$ are each independently selected from the group consisting of hydrogen, deuterium, tritium, halogen, a cyano group, a nitro group, a $C_6$-$C_{60}$ aryl group, a fluorenyl group, a $C_2$-$C_{60}$ heterocyclic group comprising at least one heteroatom selected from the group consisting of O, N, S, Si and P, a fused ring of a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-030 alkoxyl group, a $C_6$-$C_{30}$ aryloxy group and -L'-N($R_a$)($R_b$), and adjacent groups may be bonded to each other to form a ring.

c is an integer from 0-4, d is an integer from 0-3, e is an integer of 0-3, f is an integer of 0-4, and when each of these is an integer of 2 or more, each of a plurality of $R^1$, each of a plurality of $R^2$, each of a plurality of $R^3$ and each of a plurality of $R^4$ are the same as or different from each other.

Where $R^1$ to $R^4$ are each an aryl group, the aryl group may be preferably a $C_6$-$C_{30}$ aryl group, more preferably a $C_6$-$C_{18}$ aryl group, for example, phenyl, biphenyl, naphthyl, terphenyl, and the like.

The ring formed by bonding between neighboring $R^1$s, neighboring Res, neighboring $R^3$s, or neighboring $R^4$s may be a $C_6$-$C_{60}$ aromatic ring group, a fluorenyl group, a $C_2$-$C_{60}$ heterocyclic group containing at least one heteroatom of O, N, S, Si and P, a $C_3$-$C_{60}$ aliphatic ring or a fused ring of a $C_3$-$C_{60}$ aliphatic ring with a $C_6$-$C_{60}$ aromatic ring and the like. Where an aromatic ring is formed by bonding between neighboring groups, the aromatic ring may be preferably a $C_6$-$C_{30}$ aromatic ring group, more preferably, a $C_6$-$C_{14}$ aromatic ring group, for example, benzene, naphthalene, phenanthrene or the like.

In Formula 1-1, Y is C(R')(R"), N(R'), O or S, wherein R' and R" are each independently selected from the group consisting of hydrogen, a $C_6$-$C_{60}$ aryl group, a fluorenyl group, a $C_3$-$C_{60}$ heterocyclic group, a $C_1$-$C_{50}$ alkyl group, a $C_2$-$C_{60}$ alkenyl group, and a $C_6$-$C_{60}$ aryloxy group, and R' and R" may be bonded to each other to form a ring, with the proviso that the alkyl group is excluded from R' and R" where a is 1 and Y is C(R')(R").

L' is selected from the group consisting of a single bond, a $C_6$-$C_{60}$ arylene group, a fluorenylene group, a $C_3$-$C_{60}$ aliphatic ring, a $C_2$-$C_{60}$ heterocyclic group comprising at least one heteroatom selected from the group consisting of O, N, S, Si and P, and a combination thereof.

$R_a$ and $R_b$ are each independently selected from the group consisting of a $C_6$-$C_{60}$ aryl group, a fluorenyl group, a $C_3$-$C_{60}$ aliphatic ring, and a $C_2$-$C_{60}$ heterocyclic group comprising at least one heteroatom selected from the group consisting of O, N, S, Si and P.

The aryl group, arylene group, fluorenyl group, fluorenylene group, heterocyclic group, aliphatic ring group, fused ring group, alkyl group, alkenyl group, alkynyl group, alkoxyl group, or aryloxy group of $Ar^1$ to $Ar^6$, $L^1$ to $L^3$, $R^1$ to $R^4$, R', R", L', $R_a$, $R_b$, or the ring formed by adjacent groups of $R^1$ to $R^4$ or formed by R' and R" may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ aliphatic ring group, a $C_7$-$C_{20}$ arylalkyl group and $C_8$-$C_{20}$ arylalkenyl group.

Preferably, Formula 1 may be represented by one of Formulas 2 to 13.

<Formula 2>

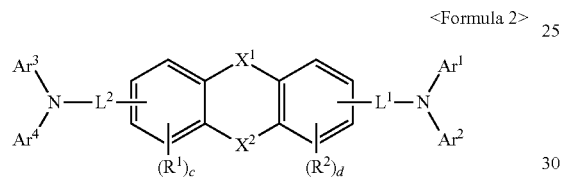

<Formula 3>

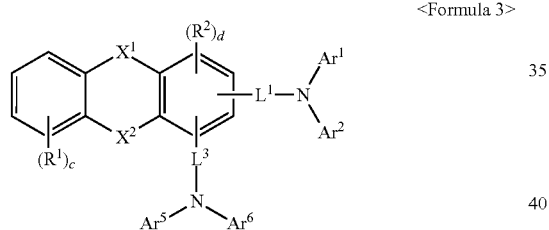

<Formula 4>

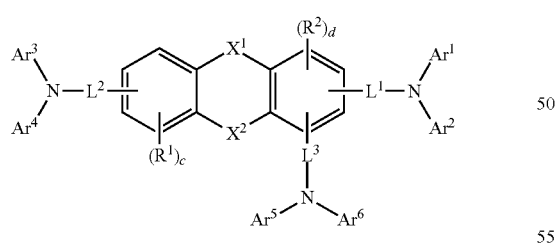

<Formula 5>

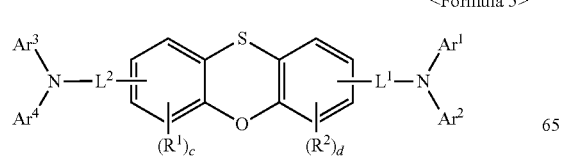

<Formula 6>

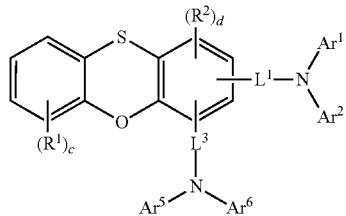

<Formula 7>

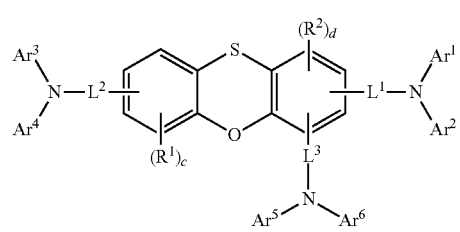

<Formula 8>

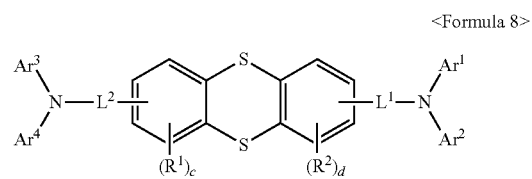

<Formula 9>

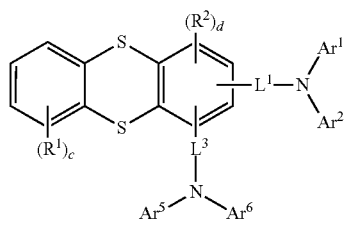

<Formula 10>

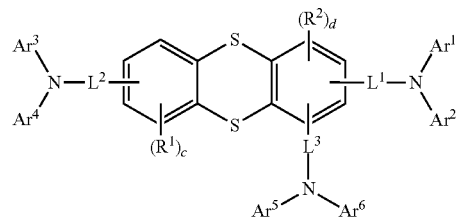

11
-continued
<Formula 11>
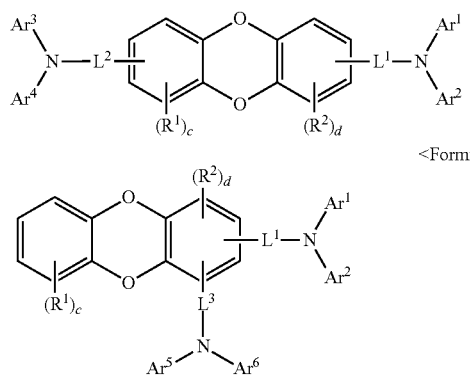
<Formula 12>
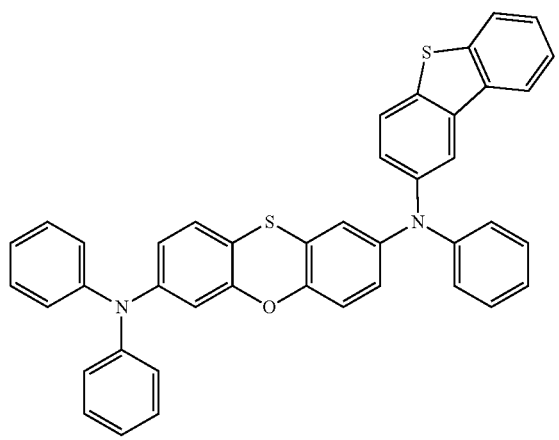
12
-continued
<Formula 13>
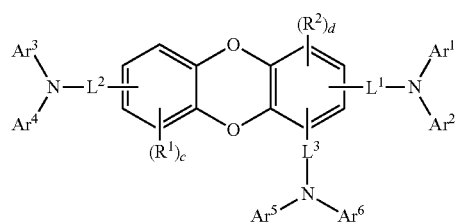
In Formulas 2 to 13, $X^1$, $X^2$, $R^1$, $R^2$, $L^1$ to $L^3$, $Ar^1$ to $Ar^6$, c and d are the same as defined for Formula 1.
Specifically, the compound represented by formula 1 may be one of the following compounds, but there is no limitation thereto.
P-1
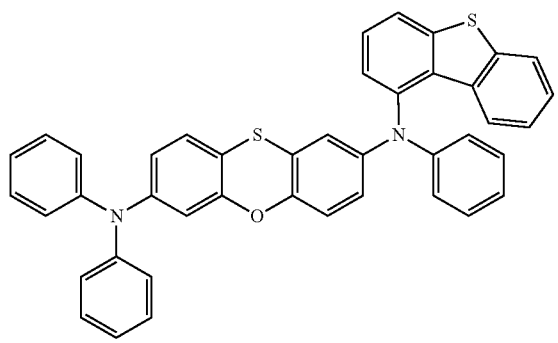
P-2
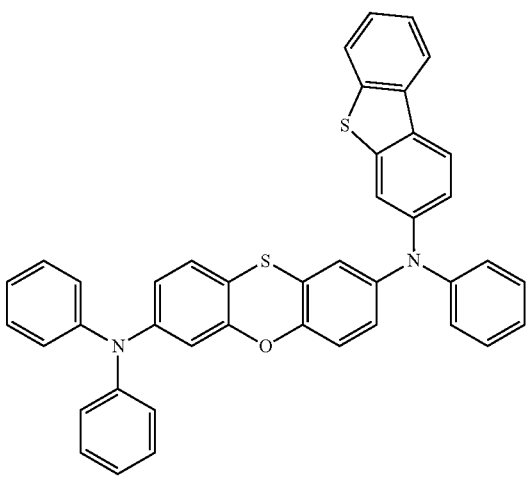
P-3
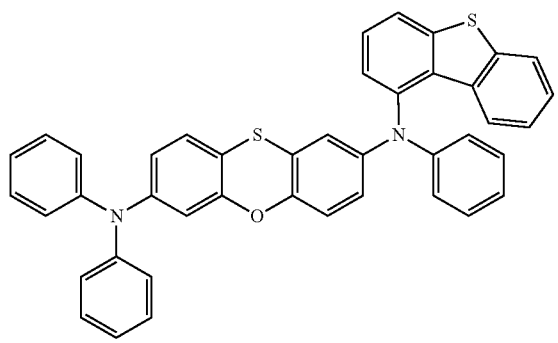
P-4
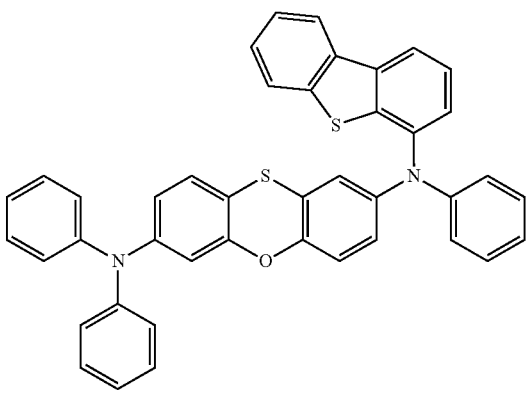

-continued
P-5
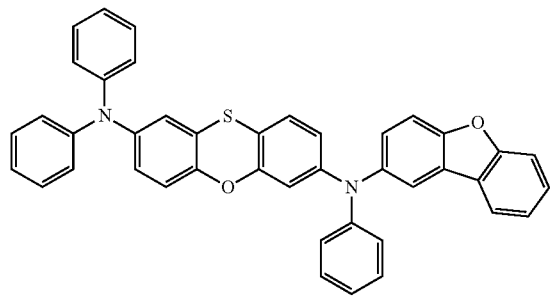
P-6
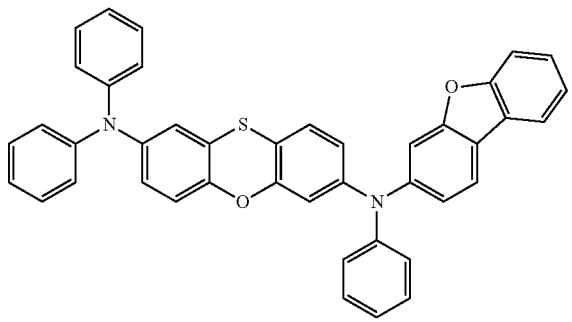
P-7
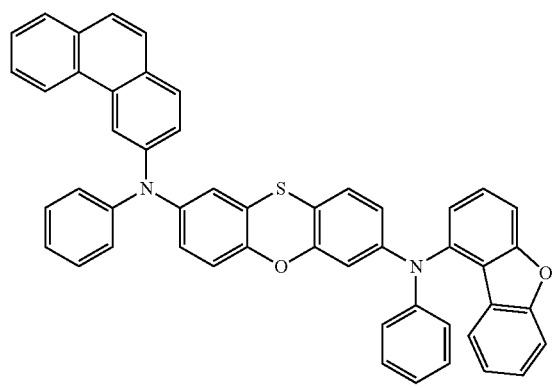
P-8
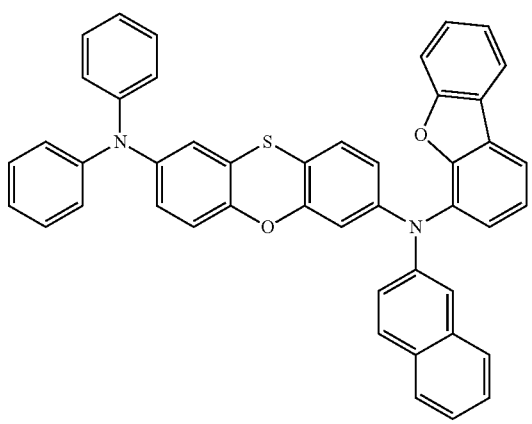
P-9
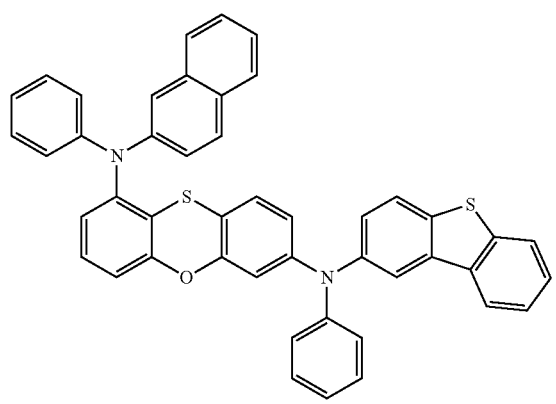
P-10
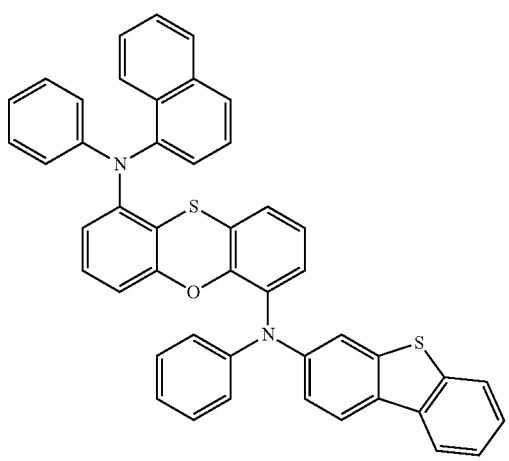

-continued
P-11
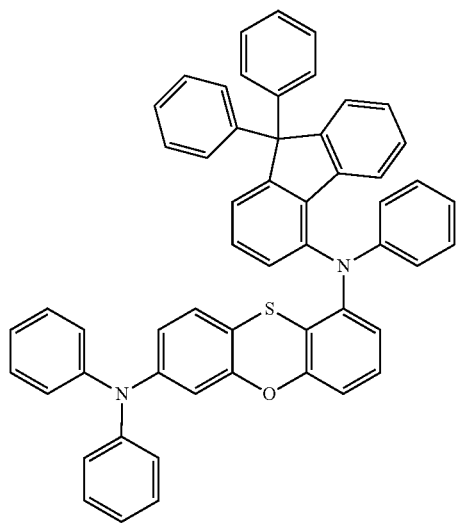
P-12
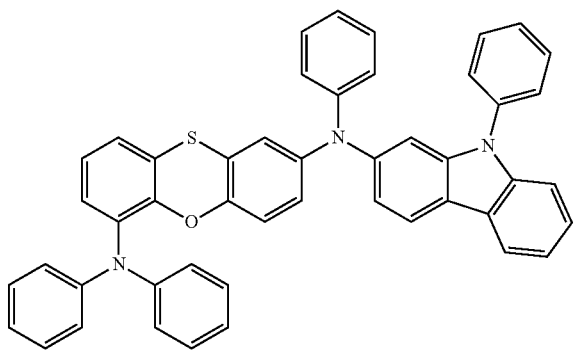
P-13
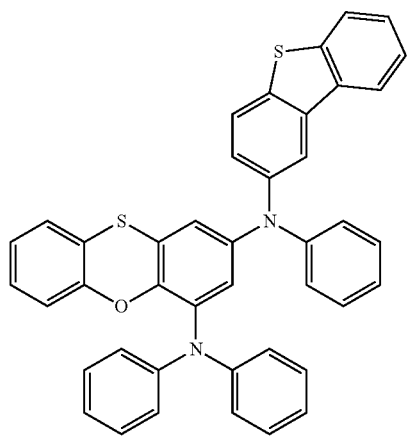
P-14
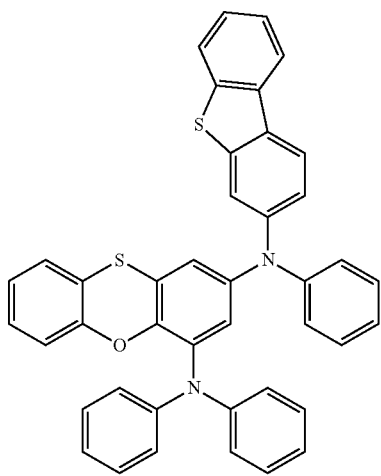
P-15
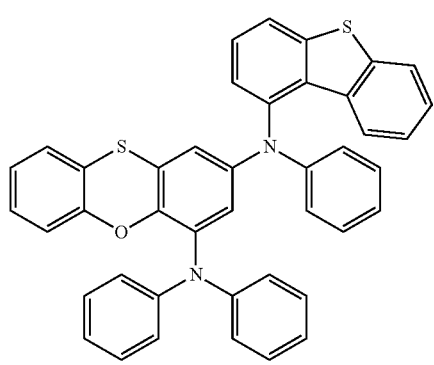
P-16
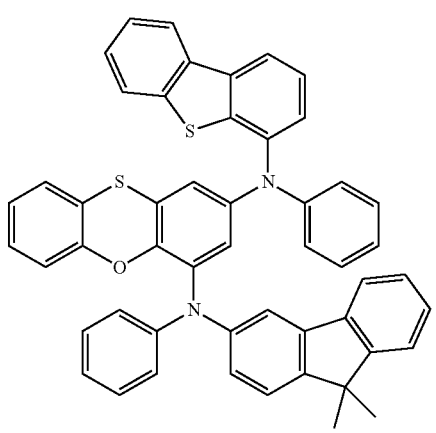

-continued
P-17
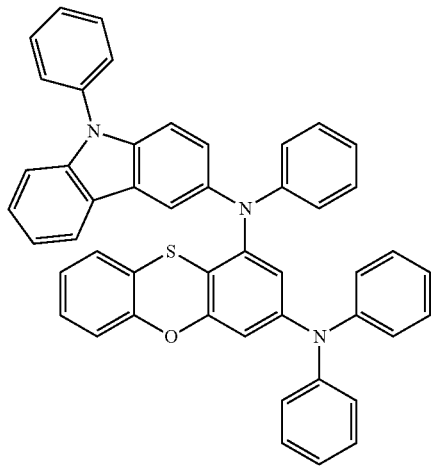
P-18
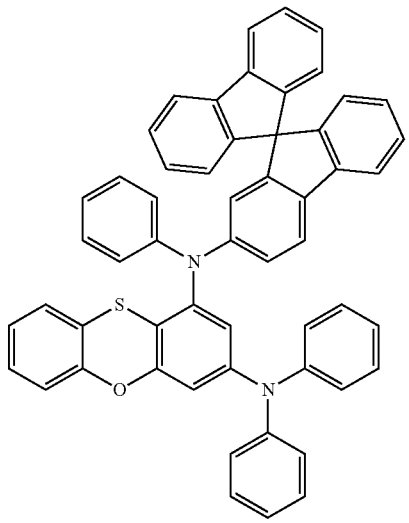
P-19
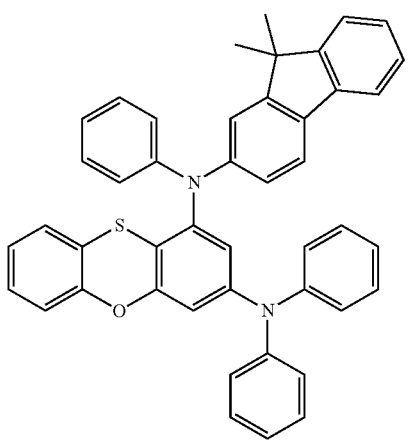
P-20
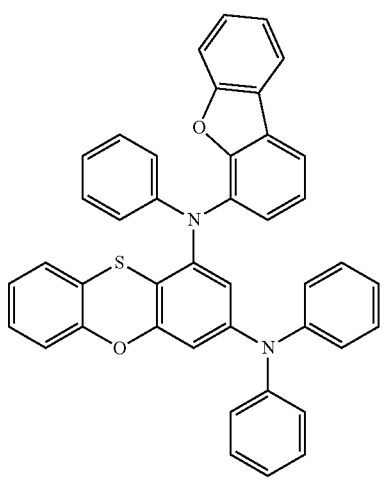
P-21
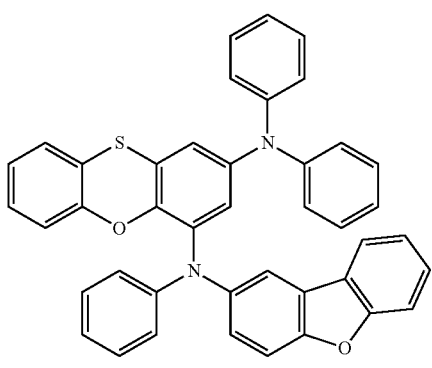
P-22
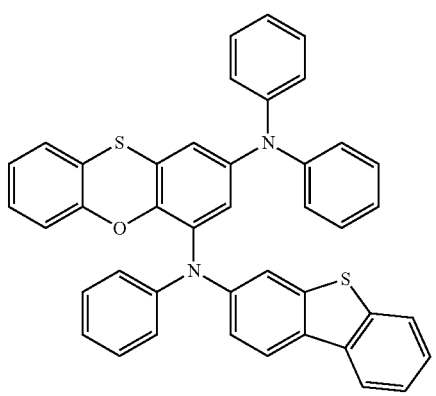

-continued
P-23 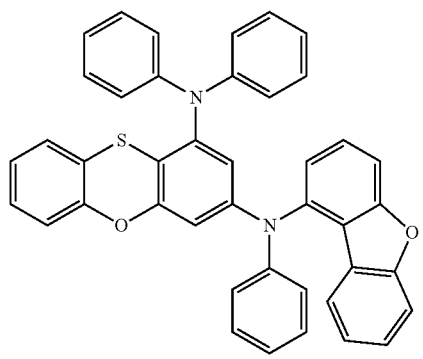
P-24 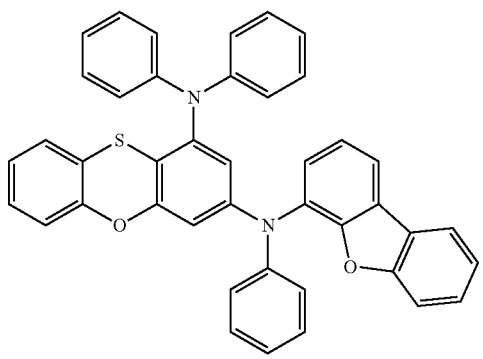
P-25 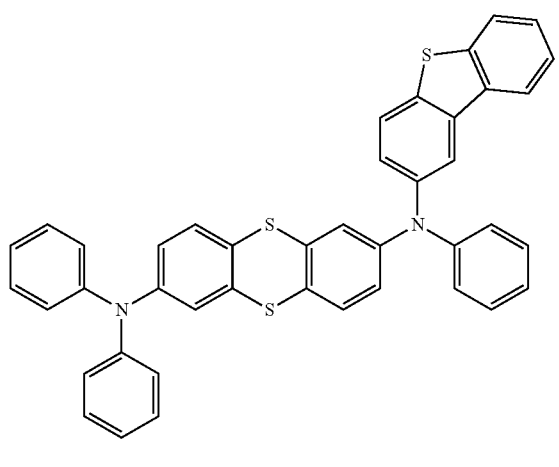
P-26 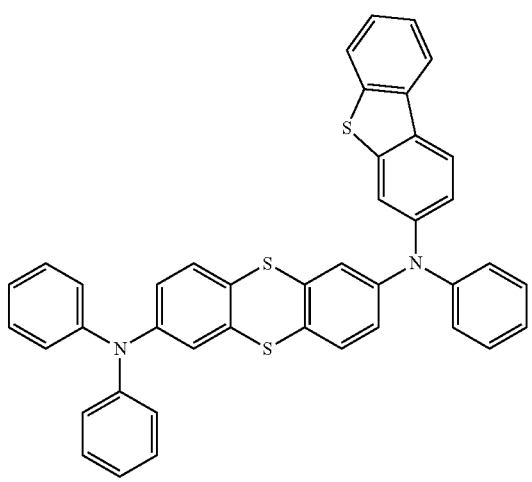
P-27 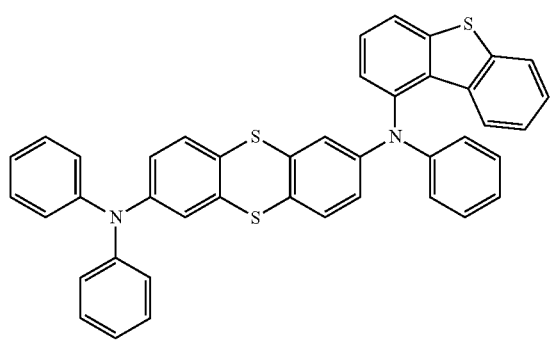
P-28 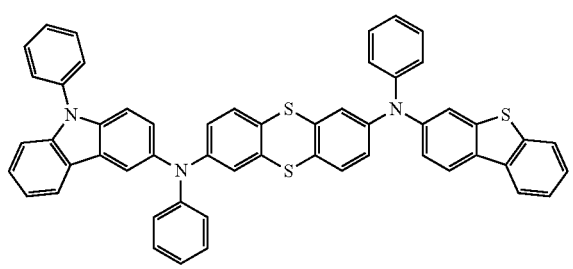
P-29 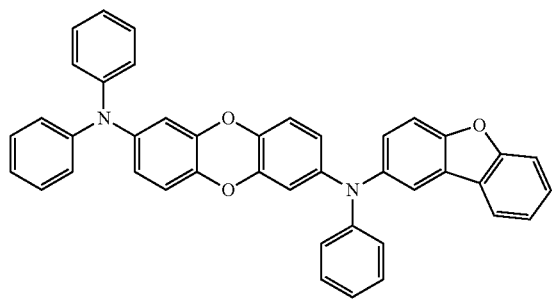
P-30 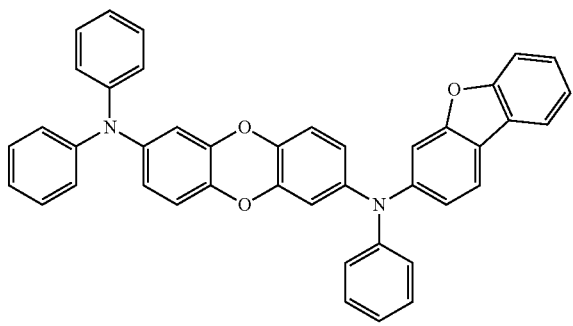

-continued
P-31
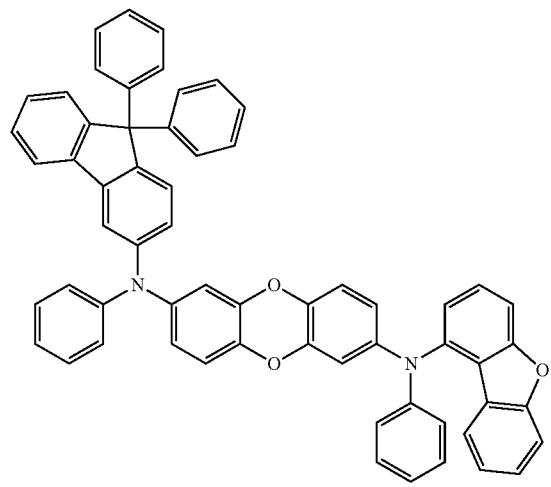
P-32
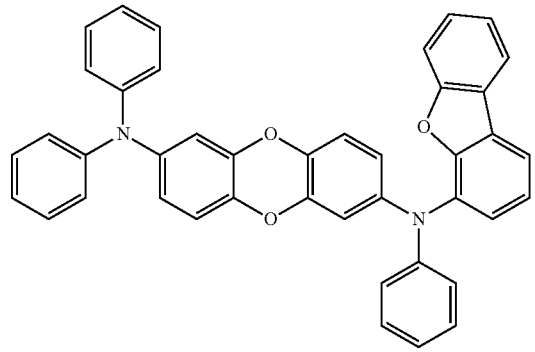
P-33
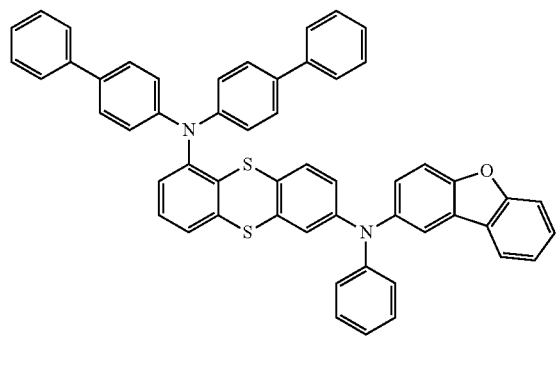
P-34
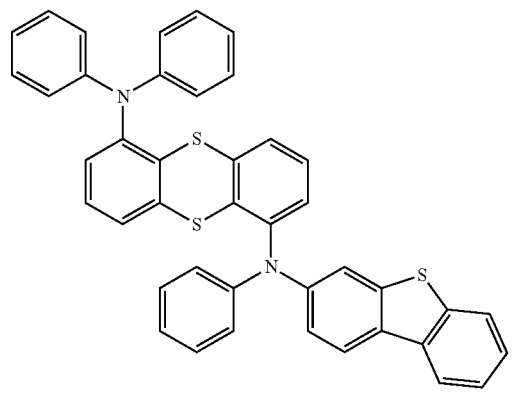
P-35
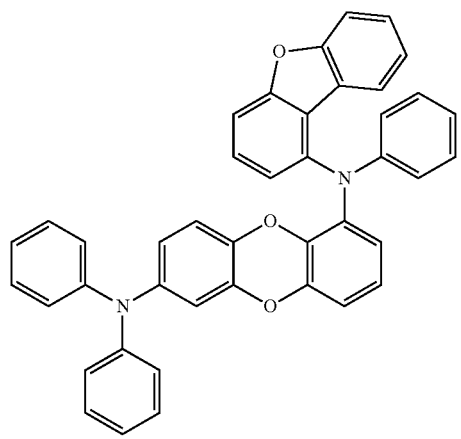
P-36
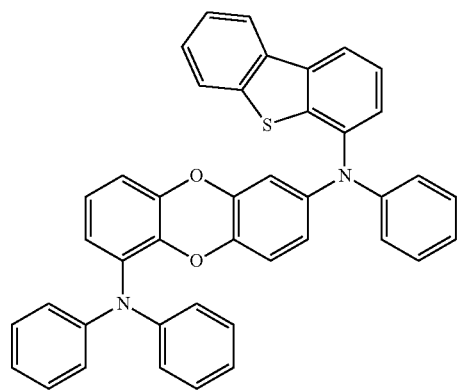

-continued
P-37
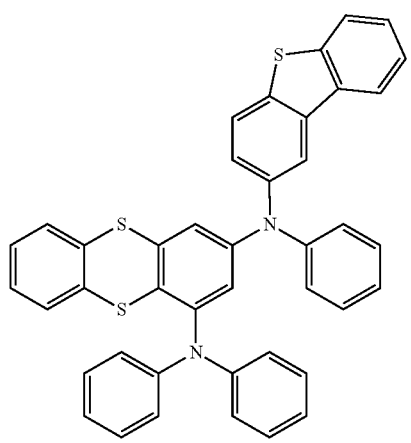
P-38
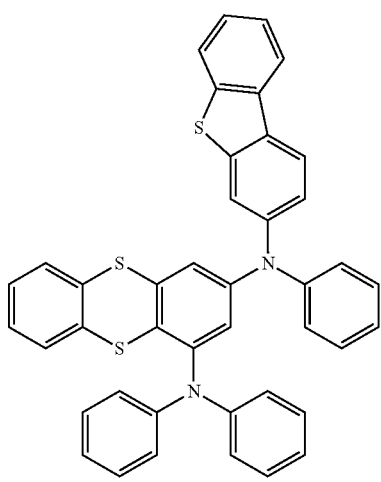
P-39
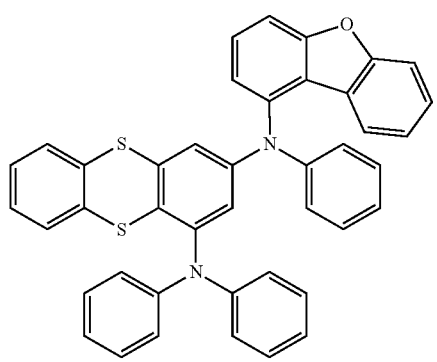
P-40
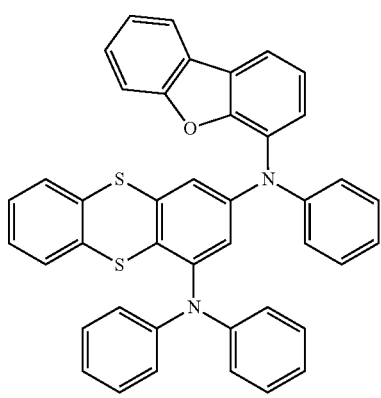
P-41
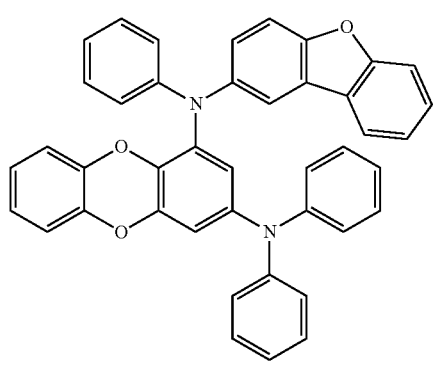
P-42
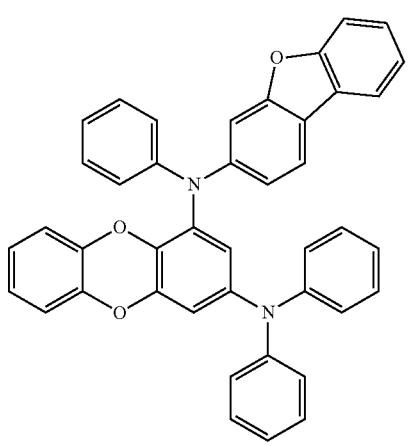

-continued
P-43
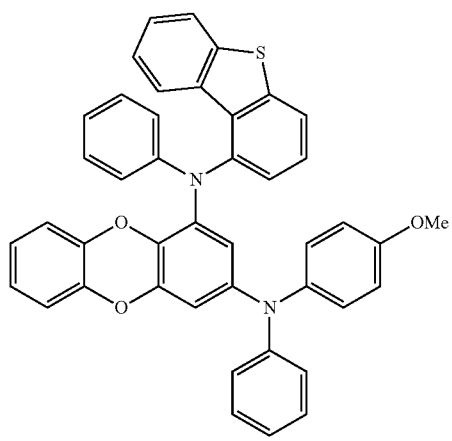
P-44
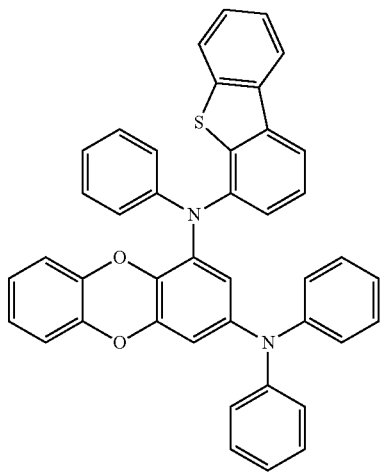
P-45
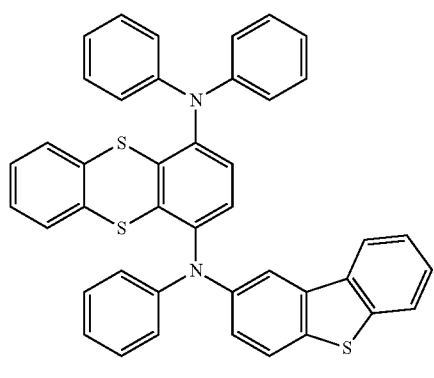
P-46
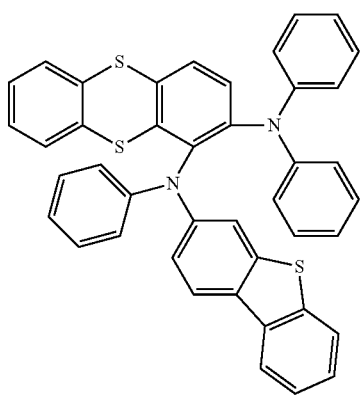
P-47
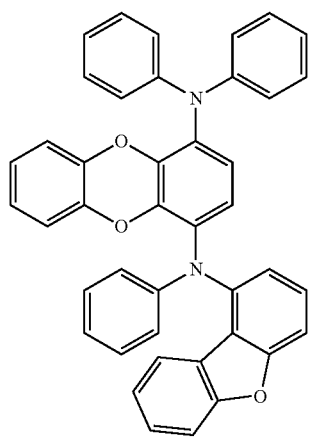
P-48
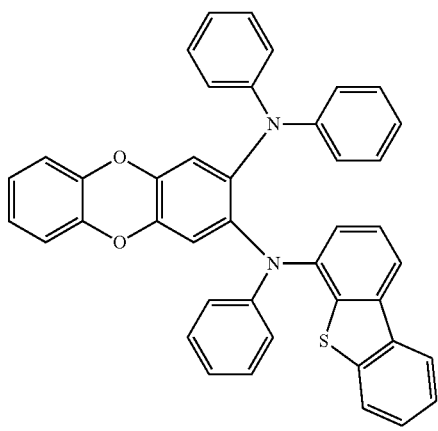

-continued
P-49
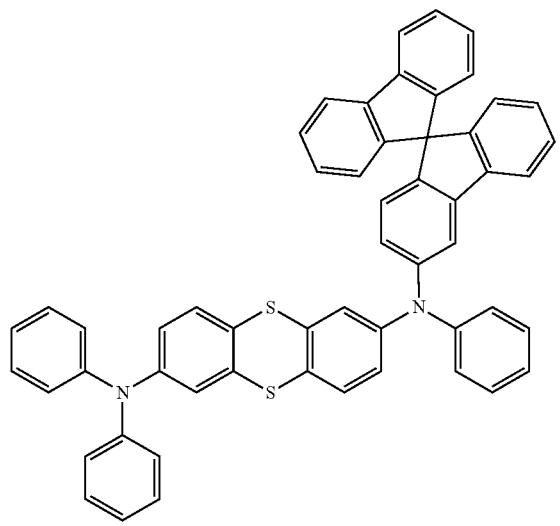
P-50
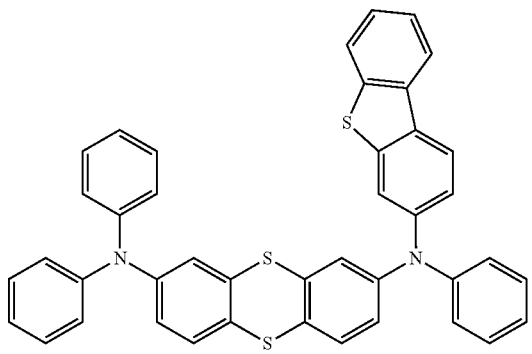
P-51
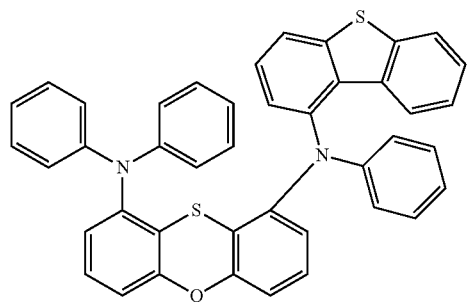
P-52
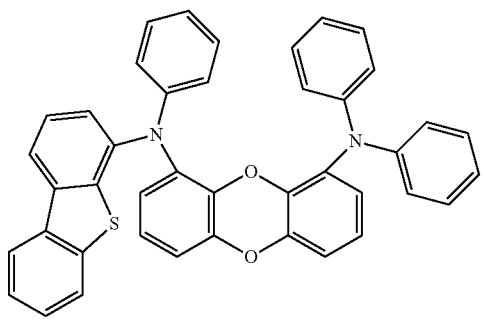
P-53
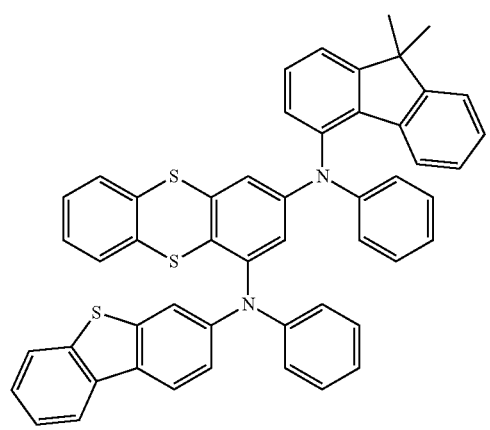
P-54
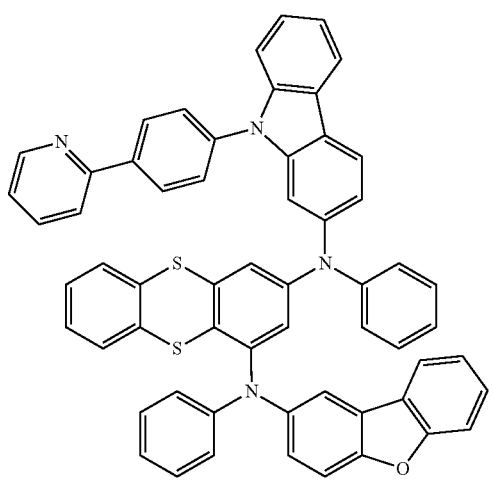

-continued
P-55
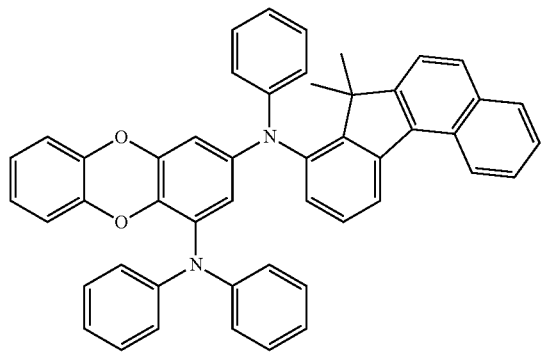
P-56
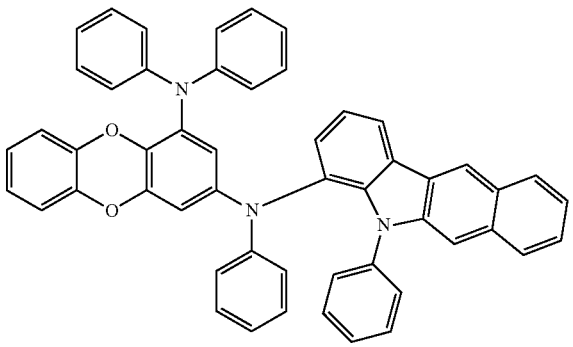
P-57
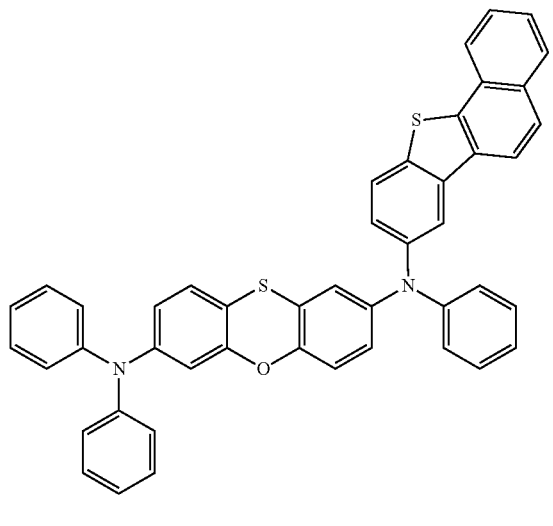
P-58
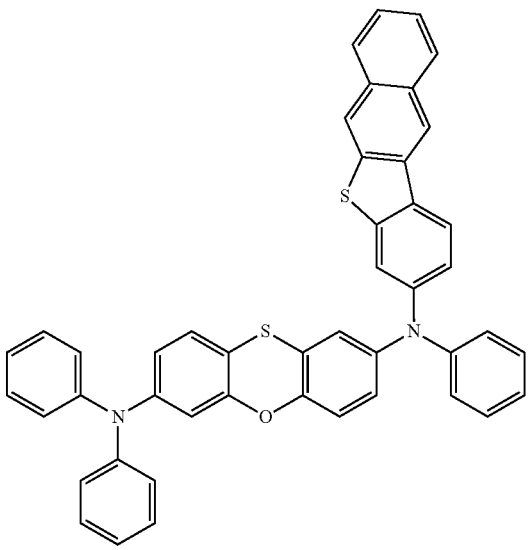
P-59
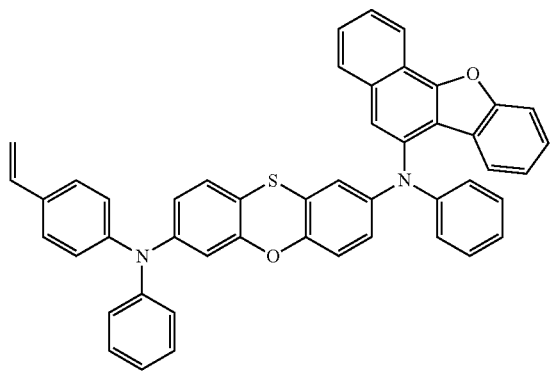
P-60
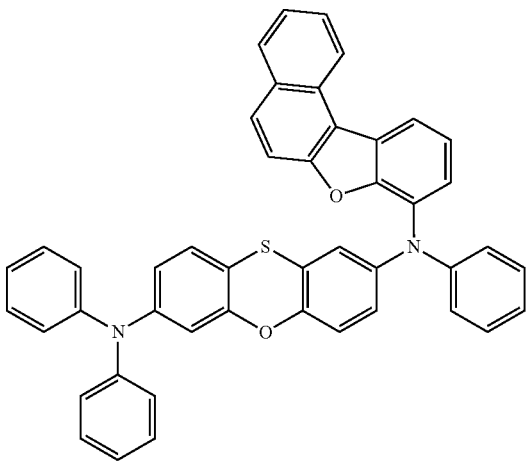

-continued
P-61
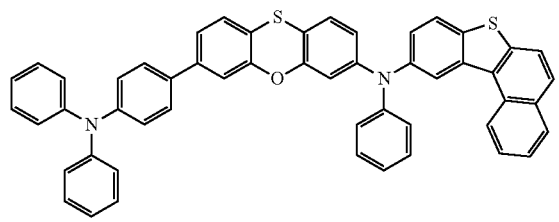
P-62
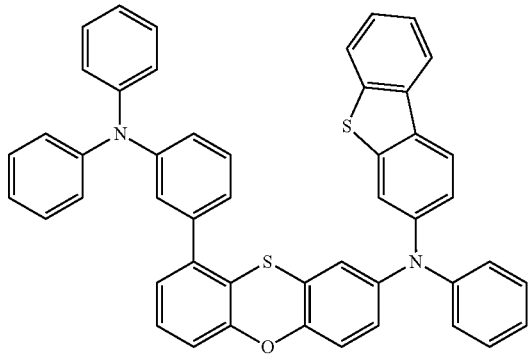
P-63
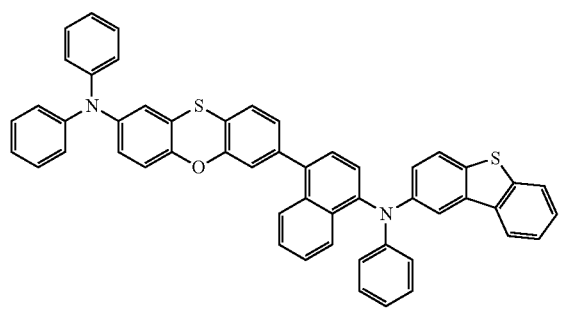
P-64
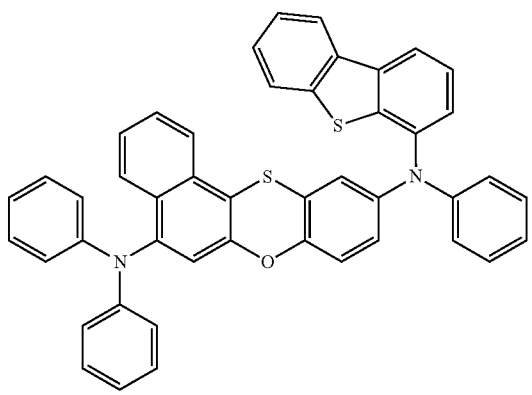
P-65
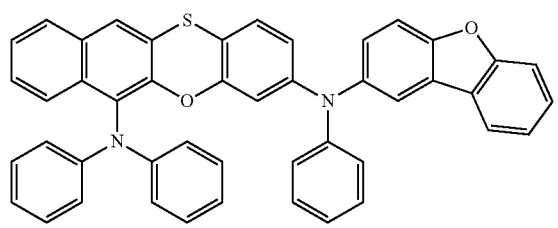
P-66
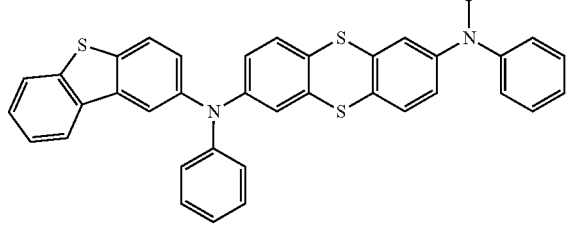

-continued
P-67
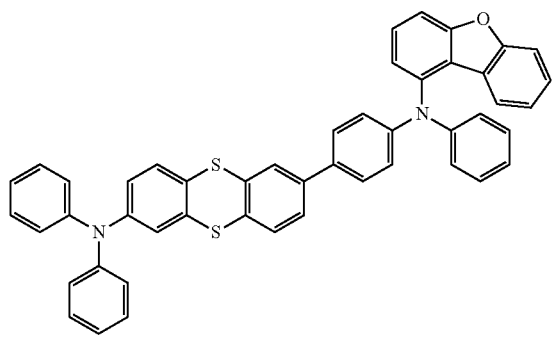
P-68
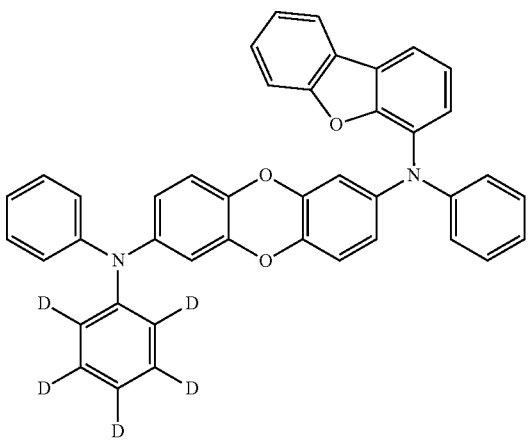
P-69
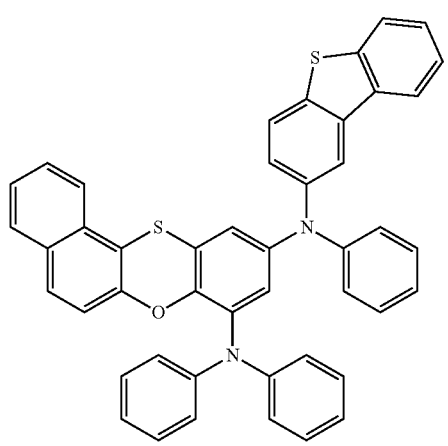
P-70
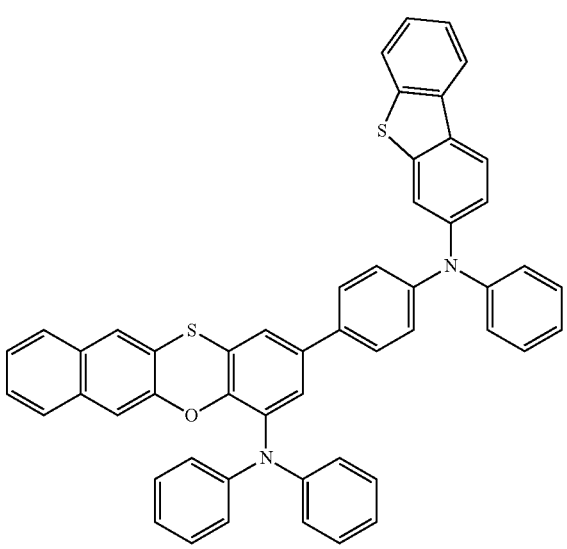
P-71
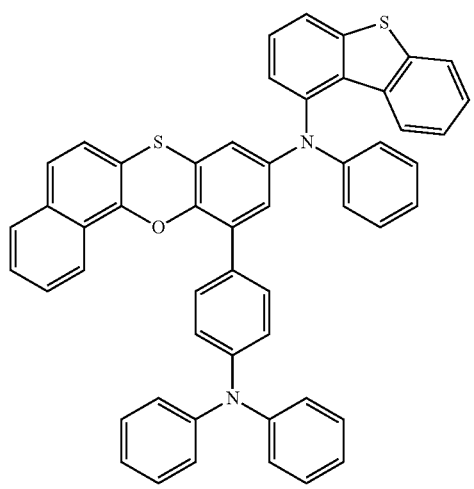
P-72
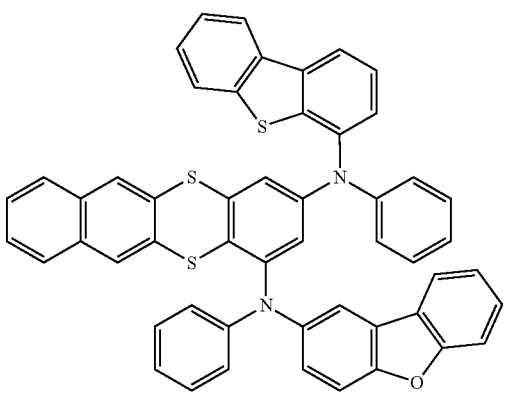

-continued
P-73
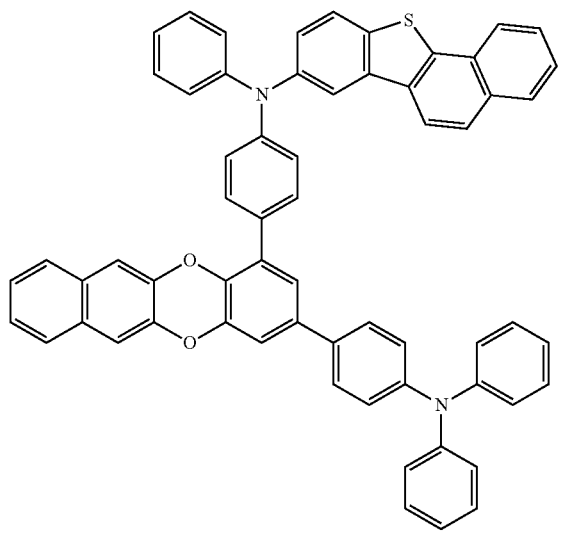
P-74
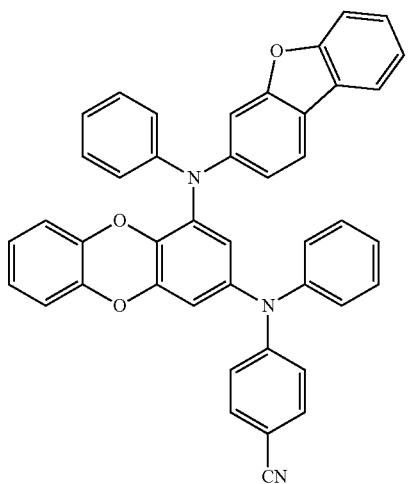
P-75
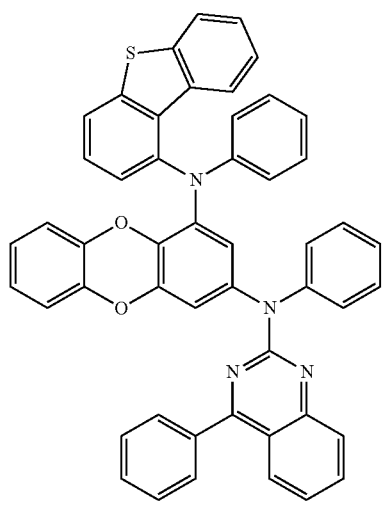
P-76
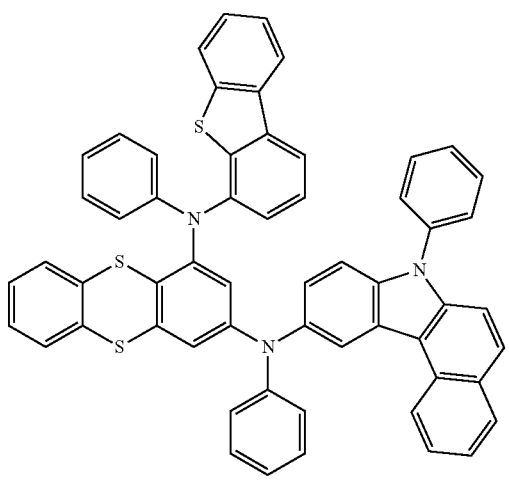
P-77
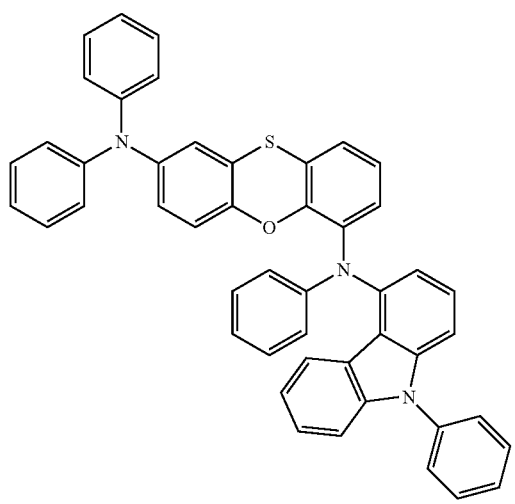
P-78
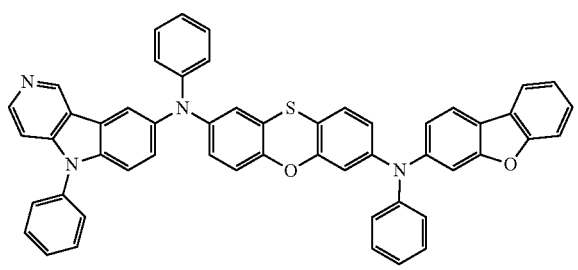

-continued
P-79
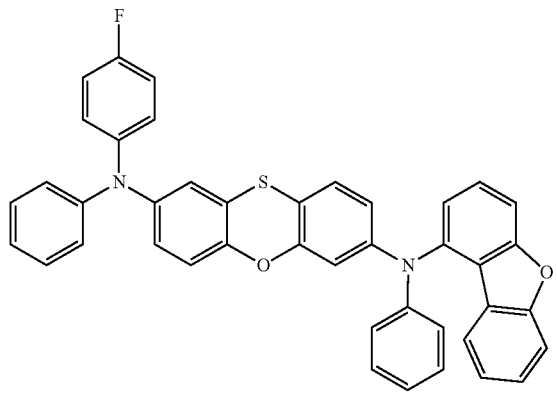
P-80
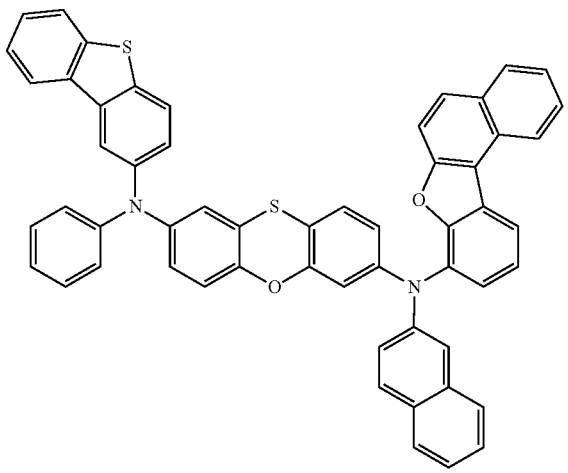
P-81
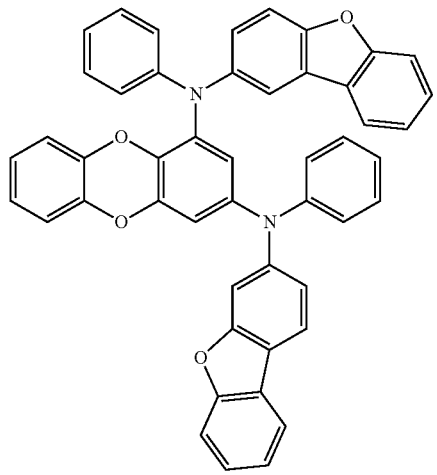
P-82
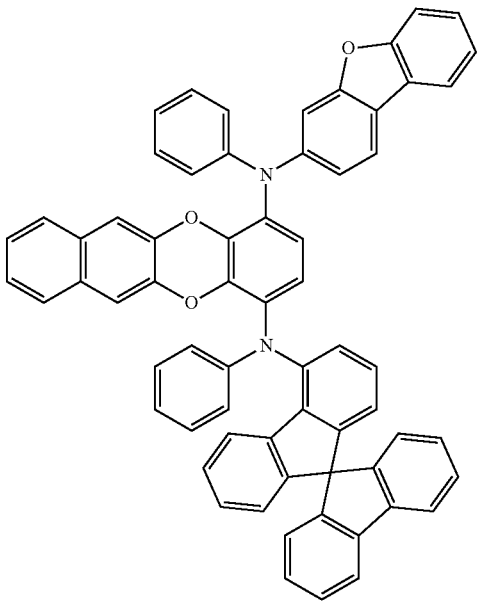
P-83
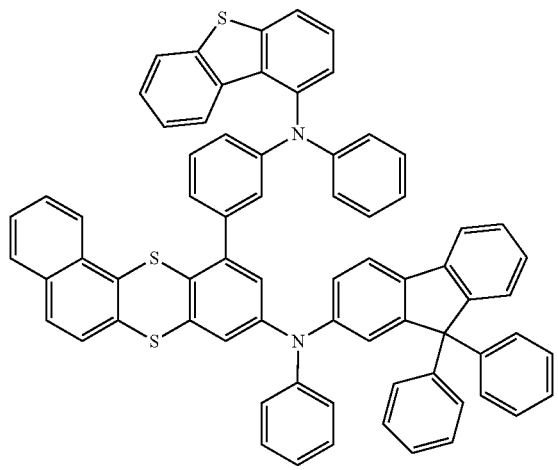
P-84
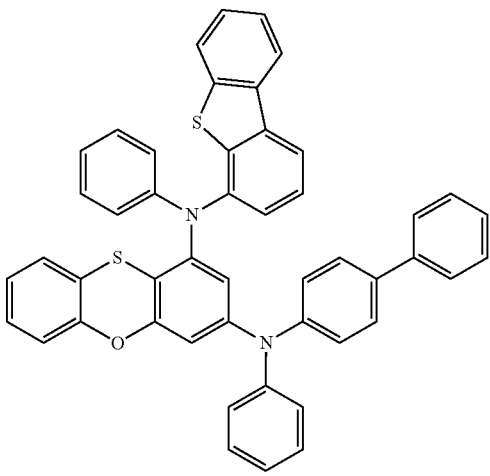

-continued
P-85
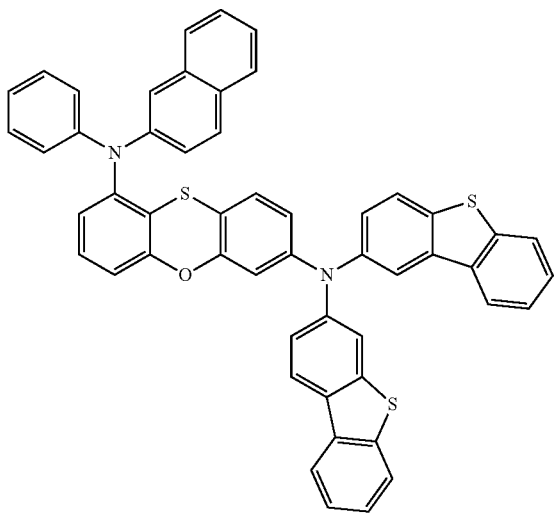
P-86
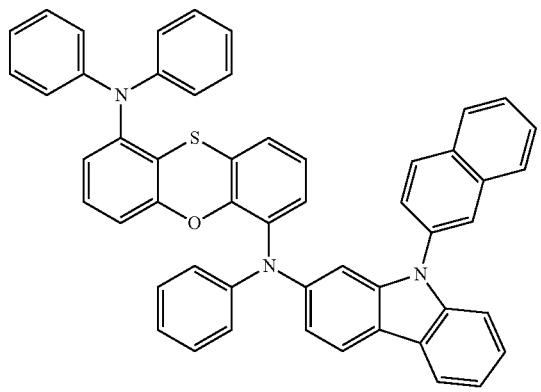
P-87
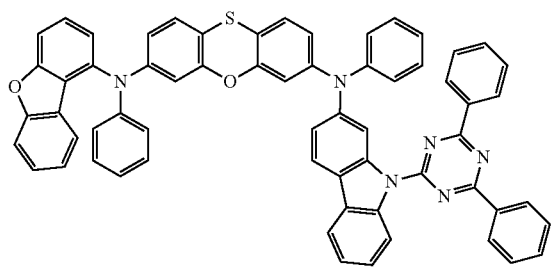
P-88
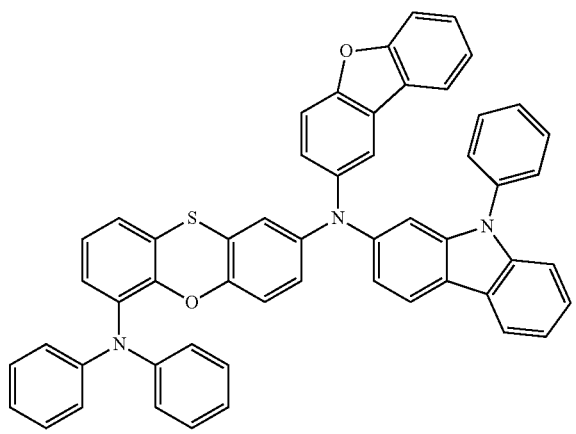
P-89
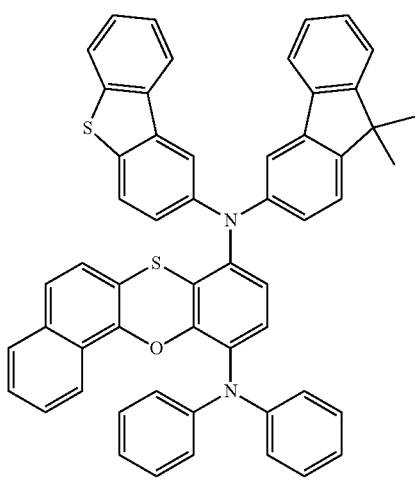
P-90
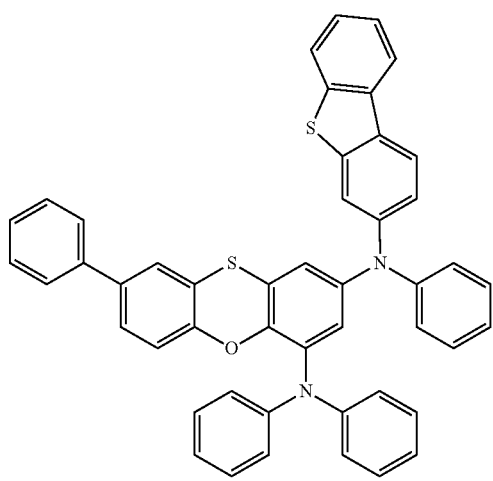

-continued
P-91
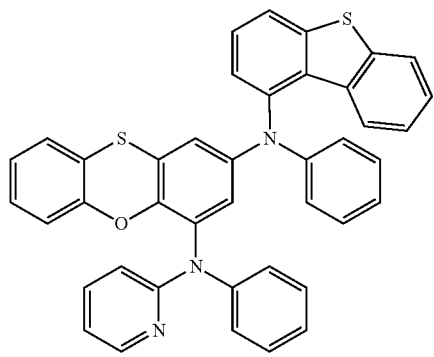
P-92
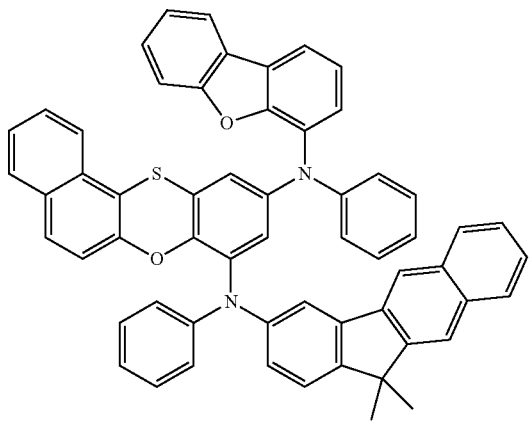
P-93
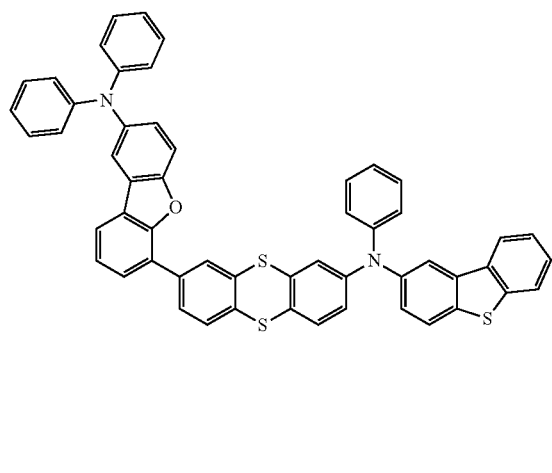
P-94
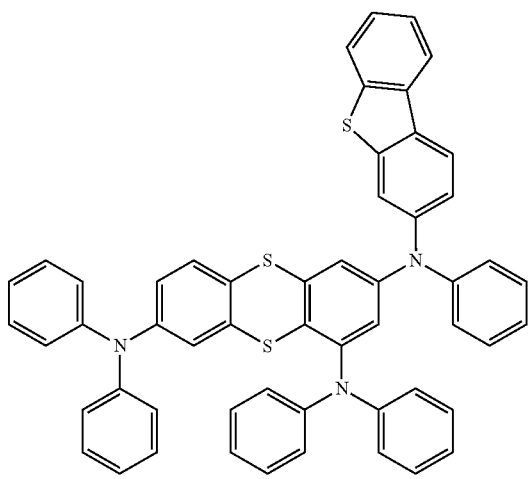
P-95
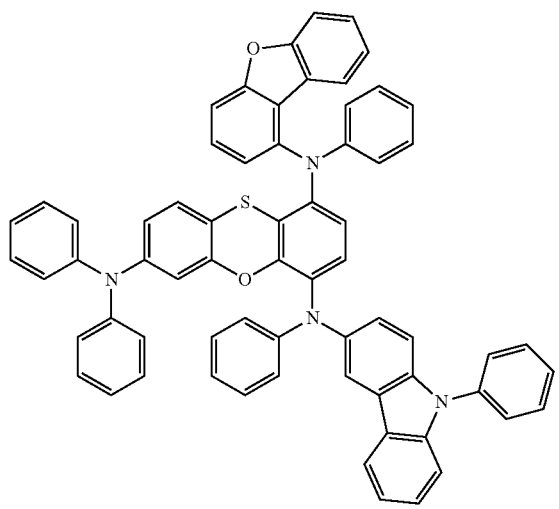
P-96
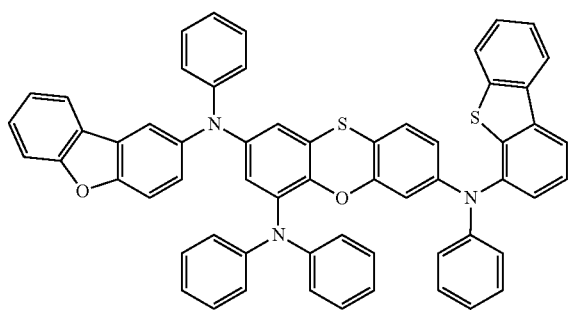

-continued
P-97
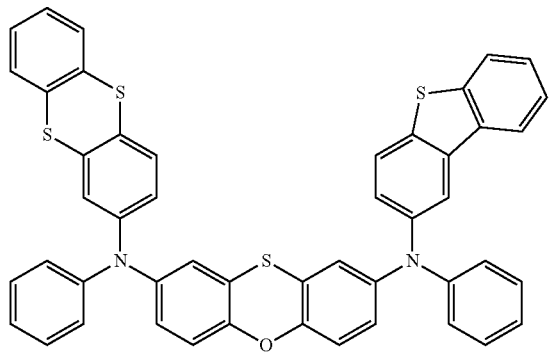
P-98
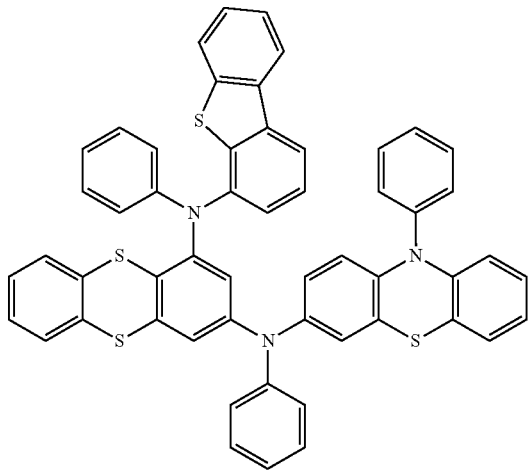
P-99
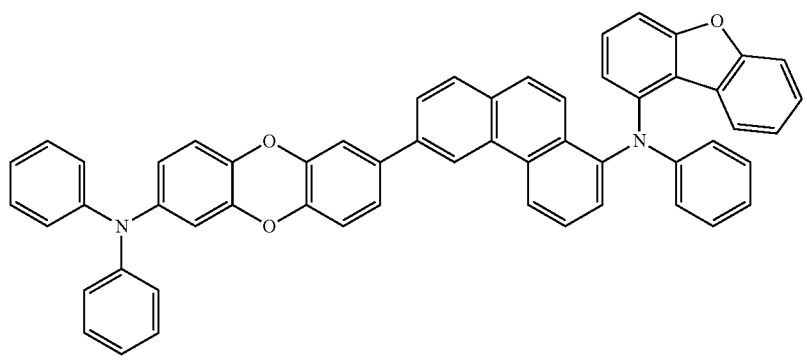
P-100
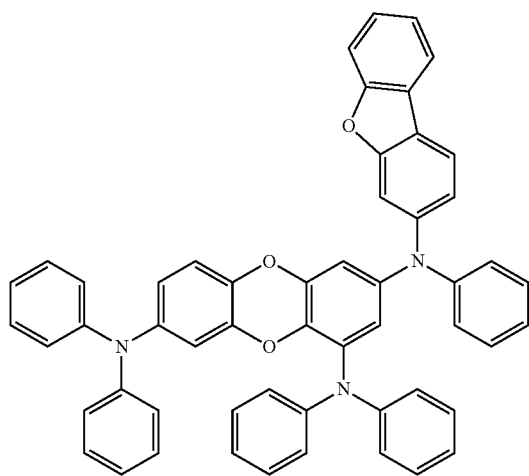
P-101
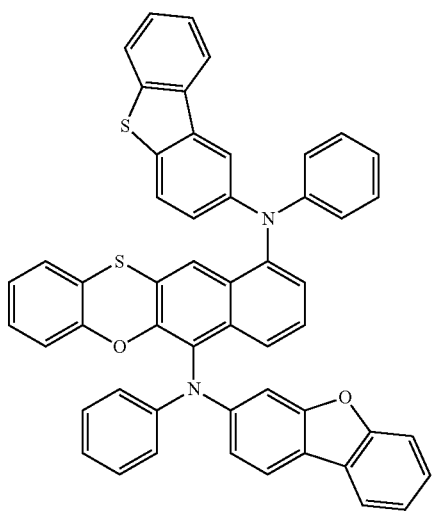

P-102

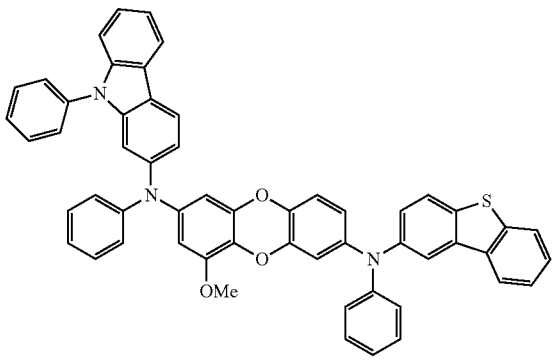

P-103

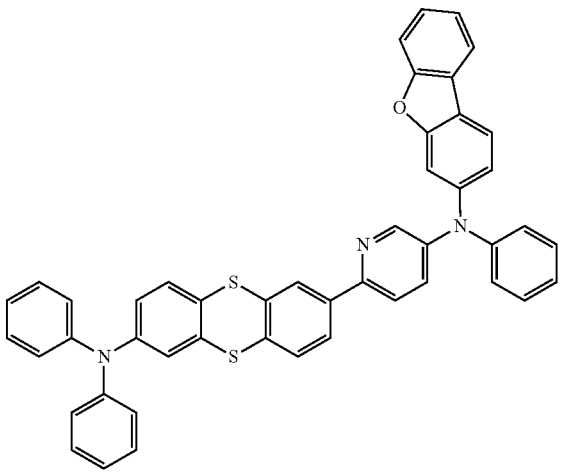

P-104

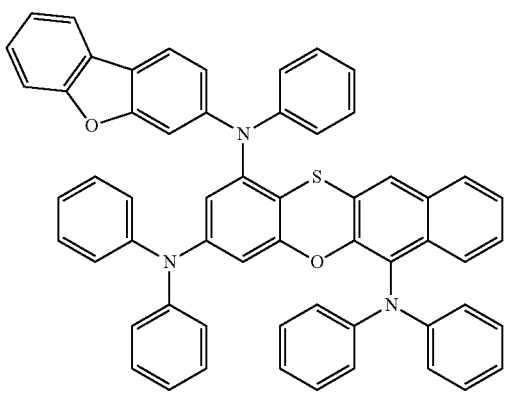

In another aspect of the present invention, the present invention provides an organic electric element comprising a first electrode, a second electrode, and an organic material layer formed between the first electrode and the second electrode, wherein the organic material layer comprises a single compound or two or more compounds represented by Formula 1.

The organic material layer comprises at least one of a hole injection layer, a hole transport layer, an emission-auxiliary layer, a light emitting layer, an electron transport-auxiliary layer, an electron transport layer and an electron injection layer, preferably, the compound may be comprised in the emission-auxiliary layer.

In another aspect of the present invention, the present invention provides an electronic device comprising a display device and a control unit for controlling the display device, wherein the display device comprises the organic electric element comprising compound represented by Formula 1.

Hereinafter, synthesis example of the compound represented by Formula 1 and preparation method of an organic electric element according to the present invention will be described in detail by way of examples. However, the present invention is not limited to the following examples.

SYNTHESIS EXAMPLE

The compound represented by Formula 1 according to the present invention can be synthesized by reacting Sub 1-A or Sub 1-B as shown in Reaction Scheme 1 or 2, but there is no limitation thereto.

<Reaction Scheme 1>

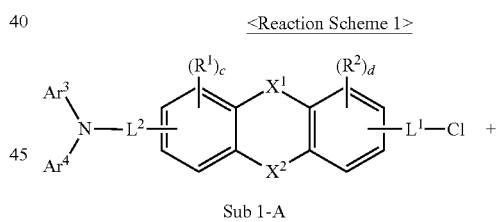

Sub 1-A

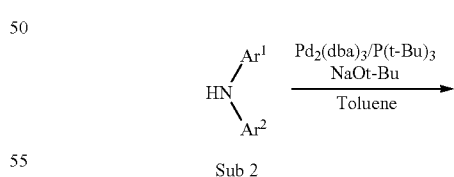

Sub 2

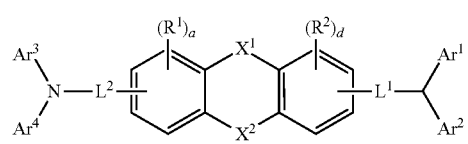

Final Product

<Reaction Scheme 2>
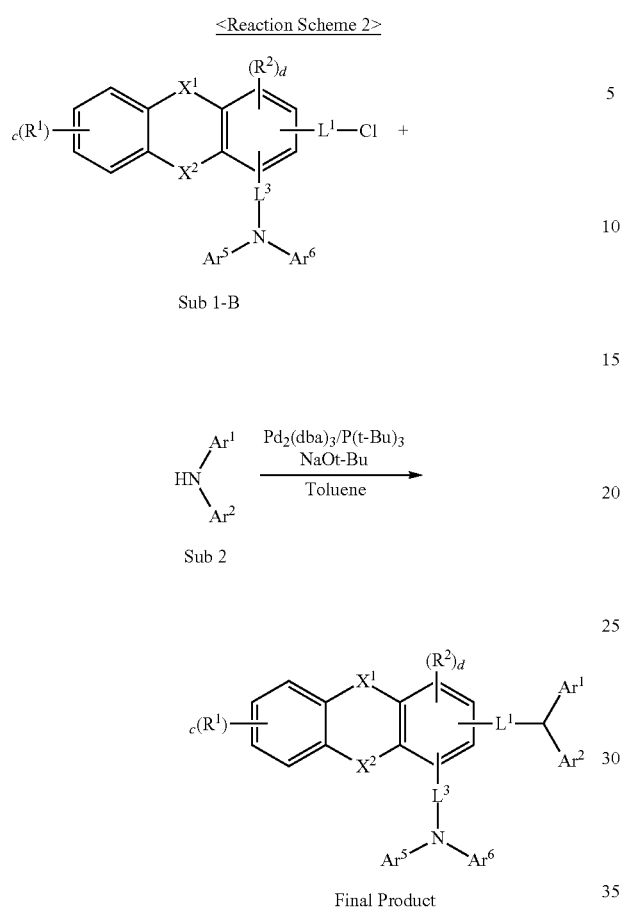
Sub 1-B
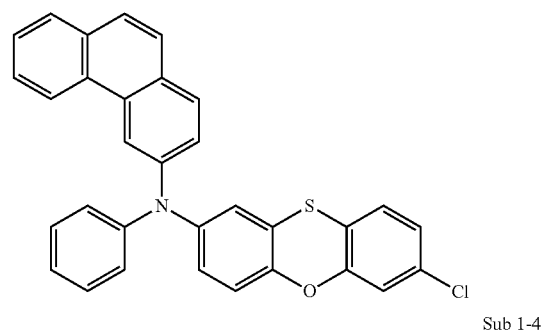
Sub 2
Final Product
I. Exemplary Compounds and Synthesis Examples of Sub 1-A and Sub 1-B
Compounds belong to Sub 1-A and Sub 1-B of Reaction Scheme 1 are as follows, but are not limited thereto.
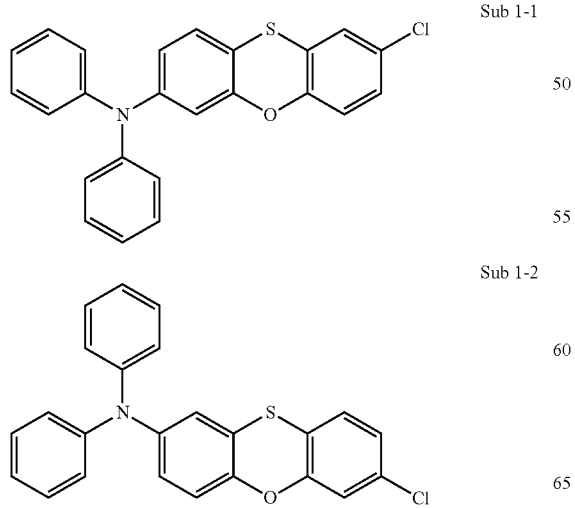

-continued
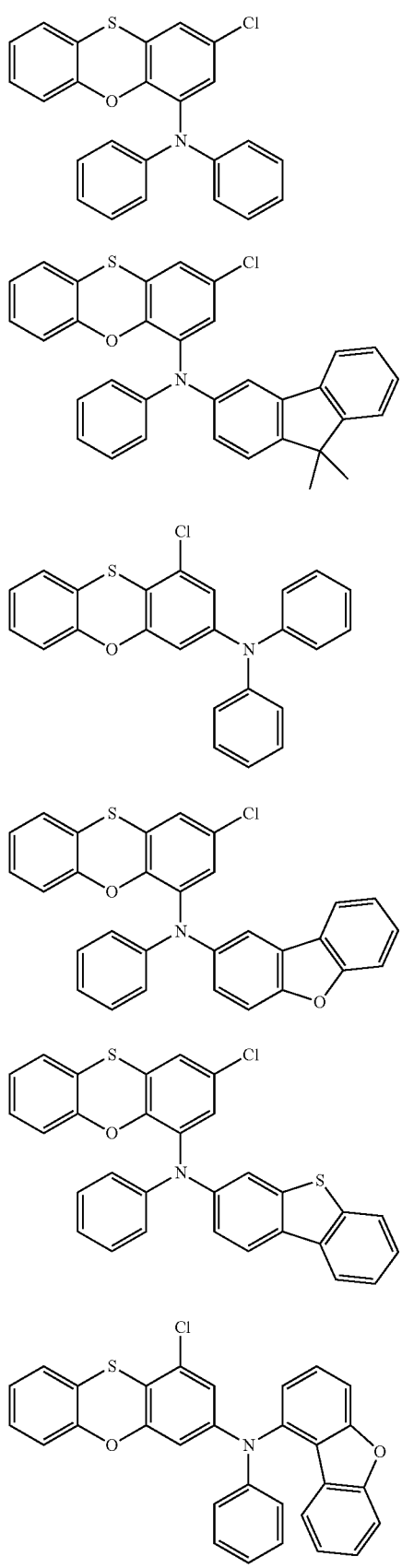
Sub 1-8
Sub 1-9
Sub 1-10
Sub 1-11
Sub 1-12
Sub 1-13
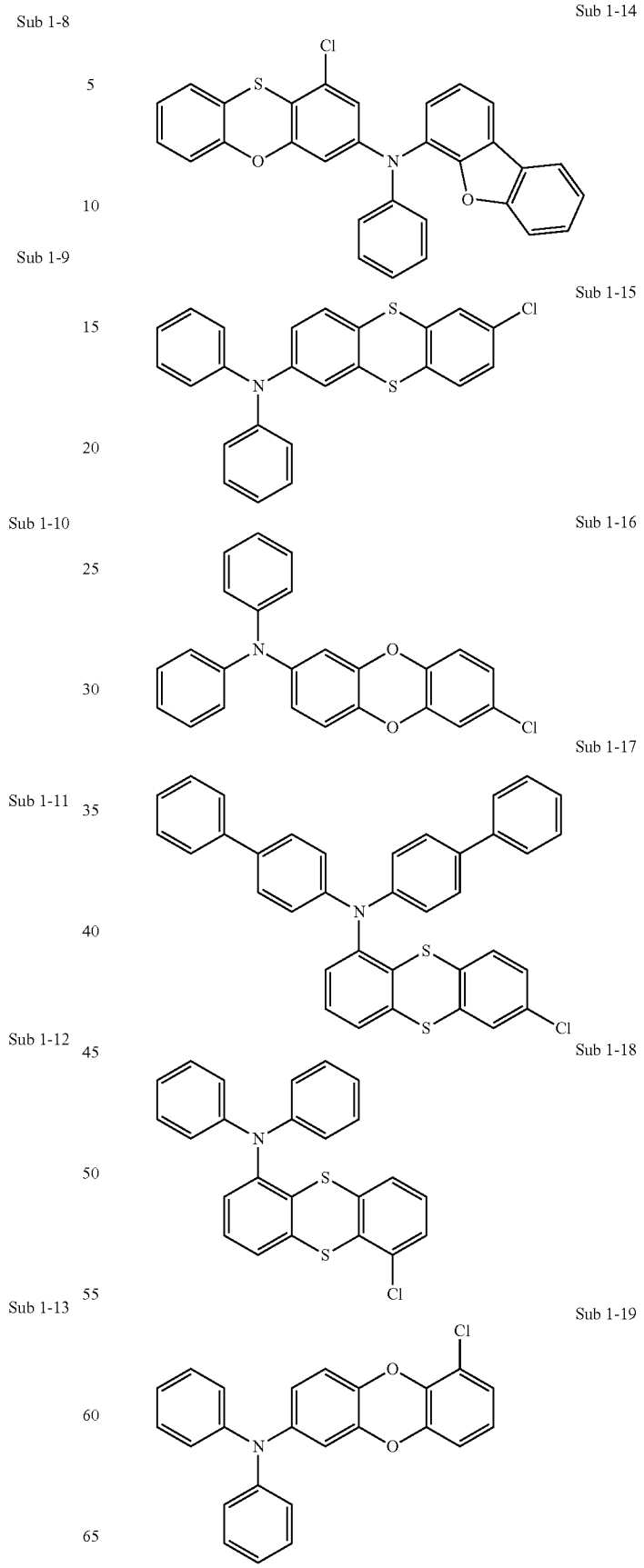
Sub 1-14
Sub 1-15
Sub 1-16
Sub 1-17
Sub 1-18
Sub 1-19

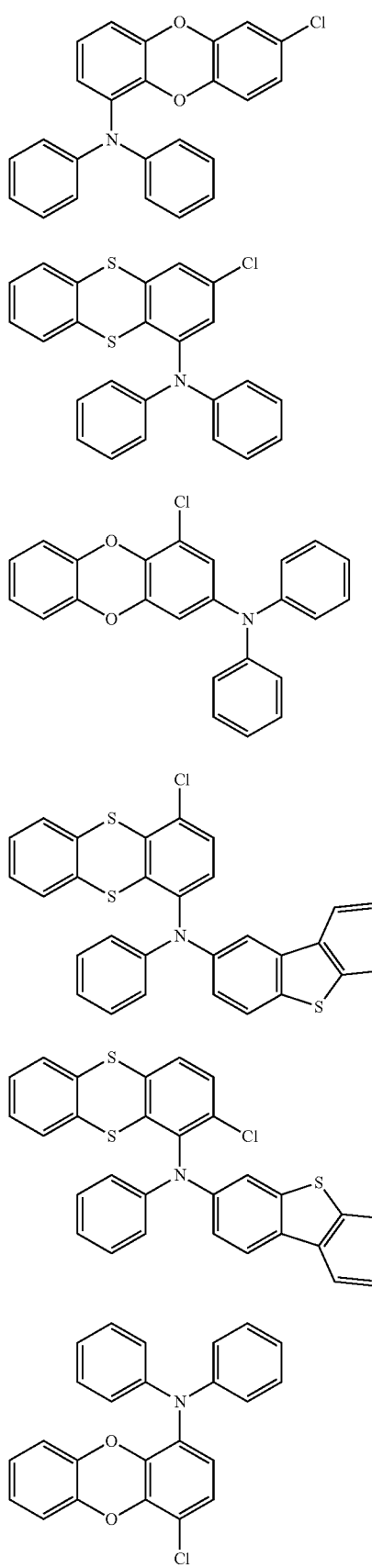
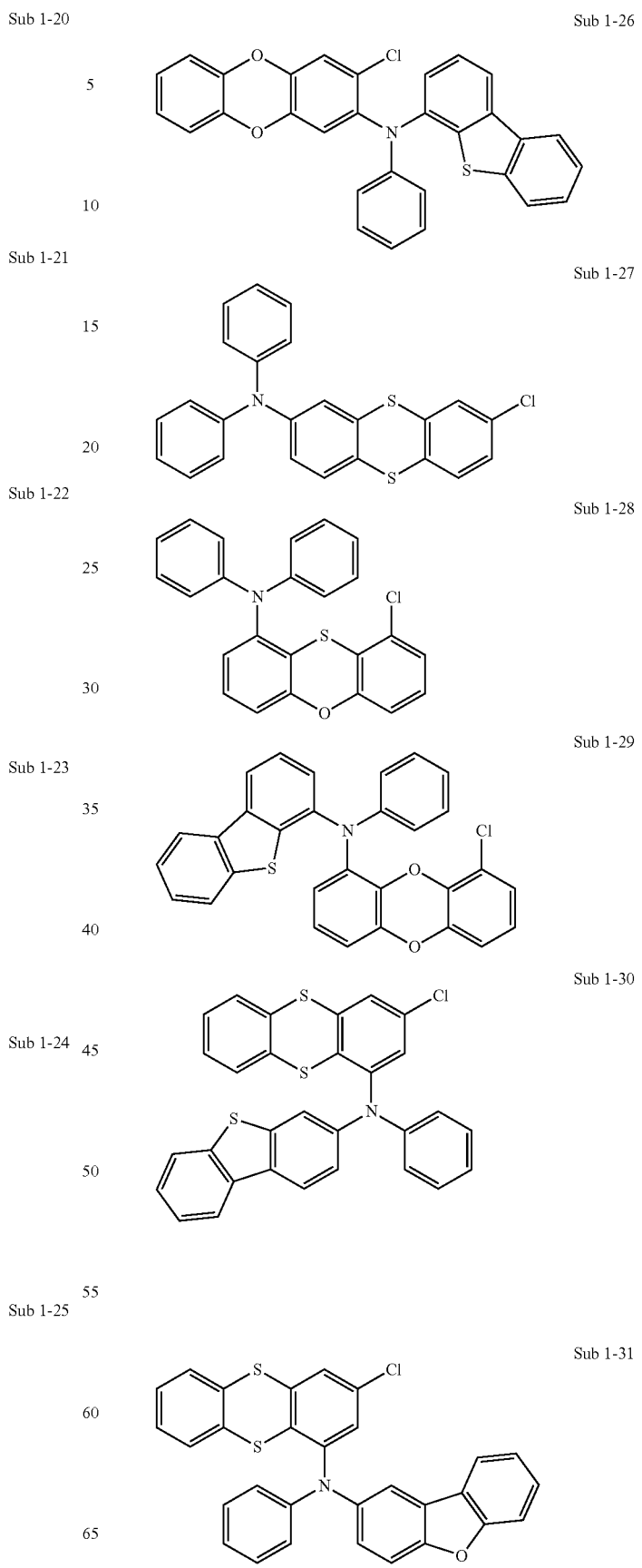

Sub 1-32
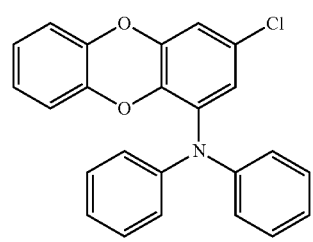
Sub 1-33
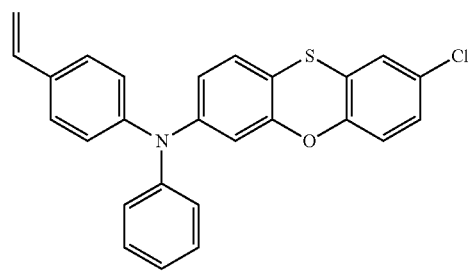
Sub 1-34
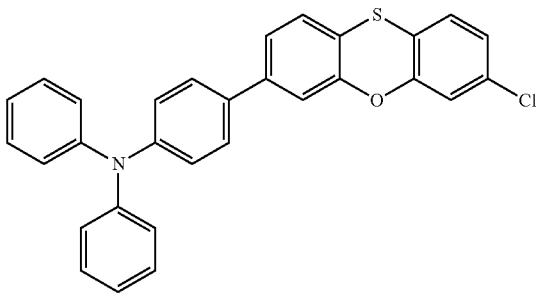
Sub 1-35
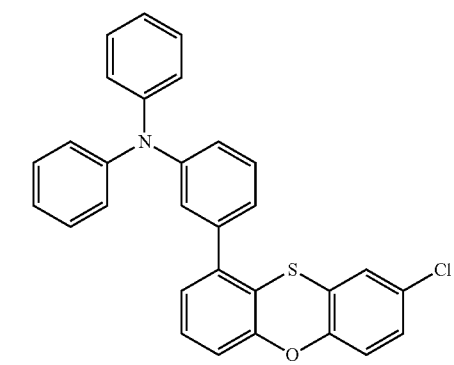
Sub 1-36
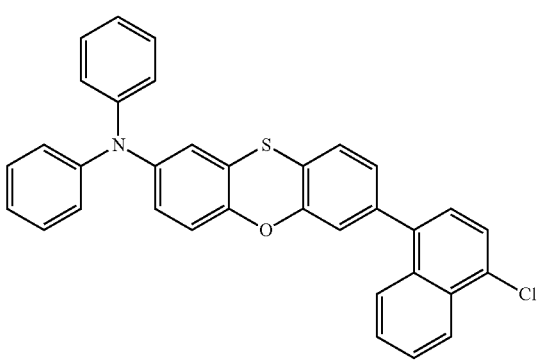
Sub 1-37
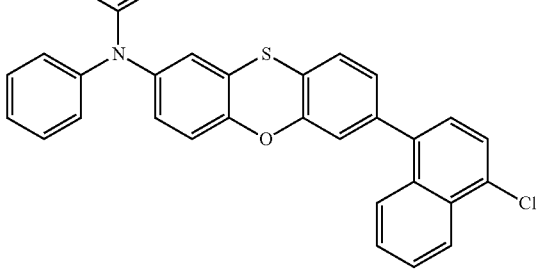
Sub 1-38
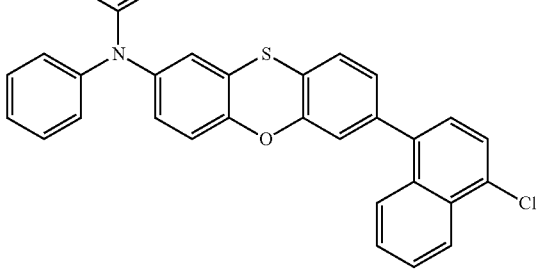
Sub 1-39
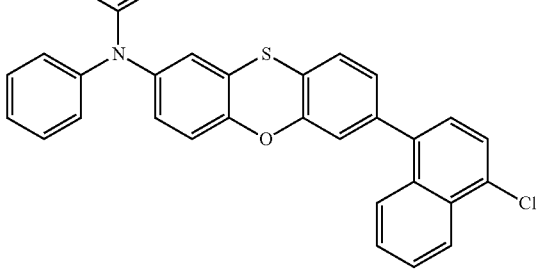
Sub 1-40
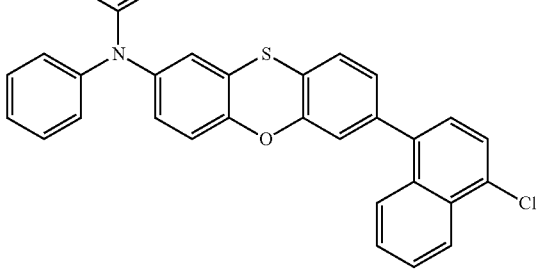
Sub 1-41
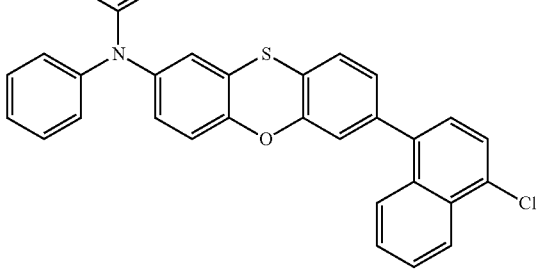

Sub 1-42
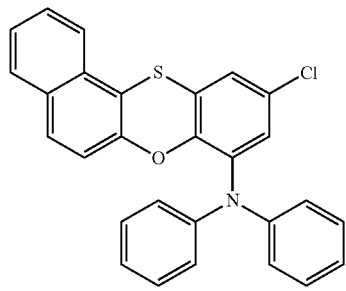
Sub 1-43
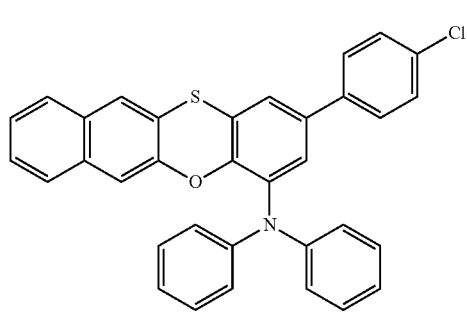
Sub 1-44
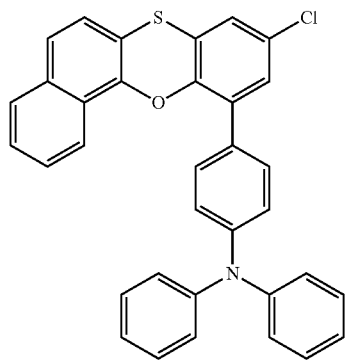
Sub 1-45
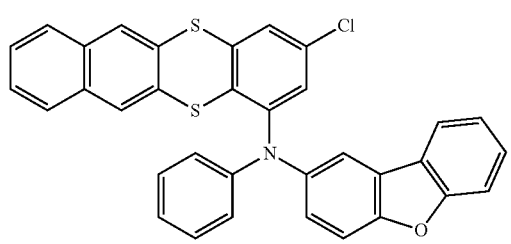
Sub 1-46
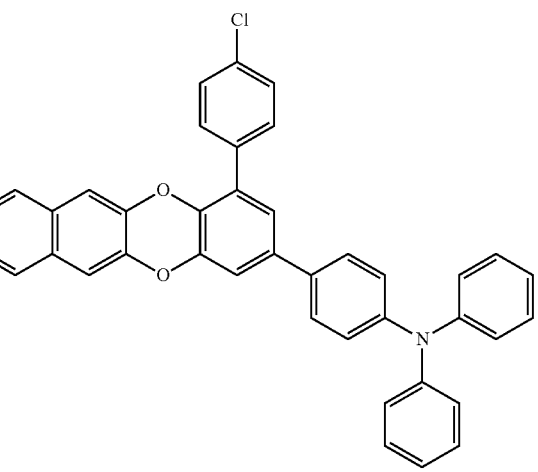
Sub 1-47
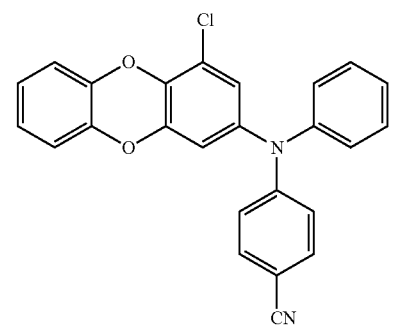
Sub 1-48
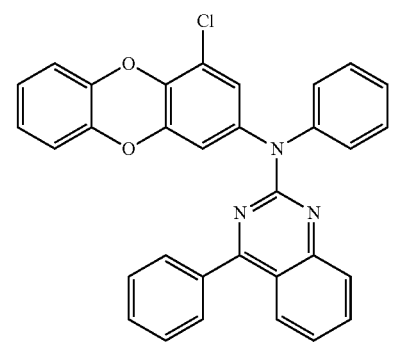
Sub 1-49
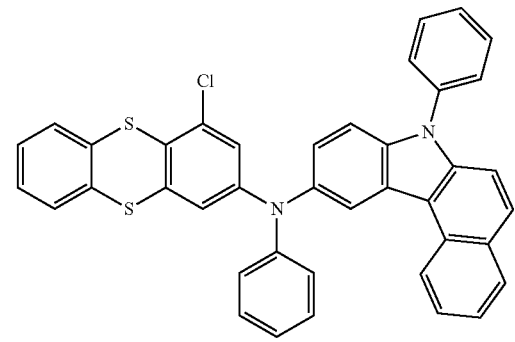

Sub 1-50
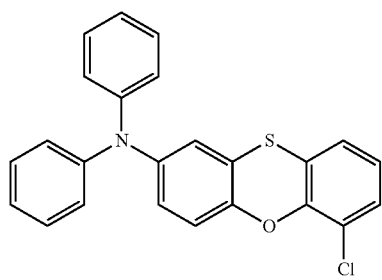
Sub 1-51
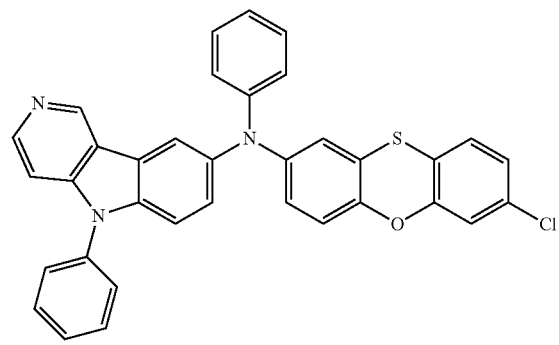
Sub 1-52
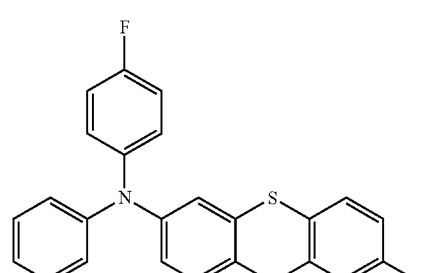
Sub 1-53
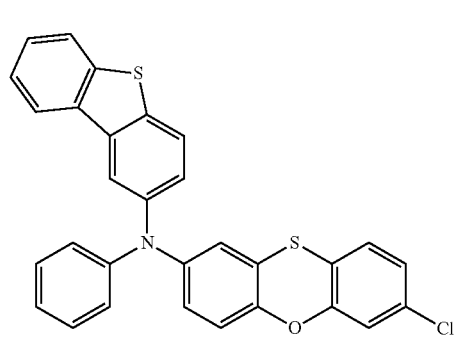
Sub 1-54
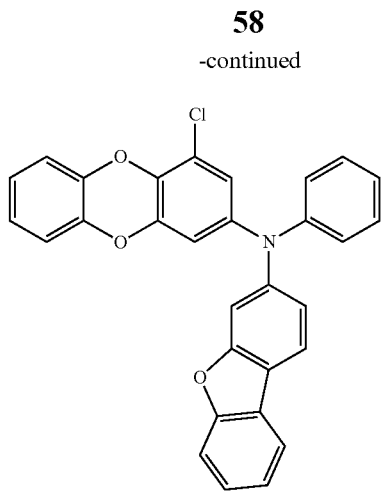
Sub 1-55
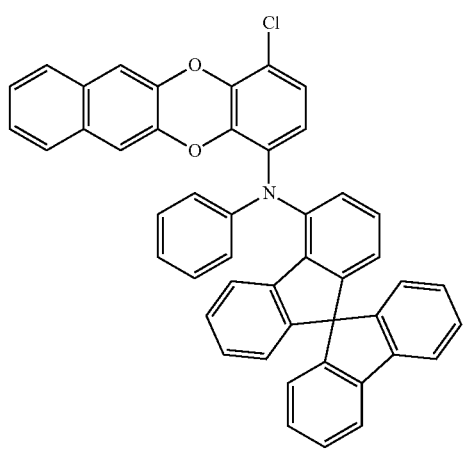
Sub 1-56
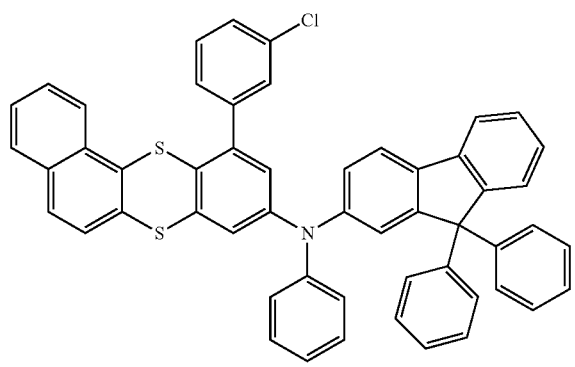
Sub 1-57
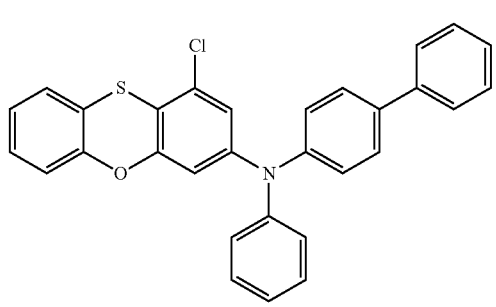

Sub 1-58
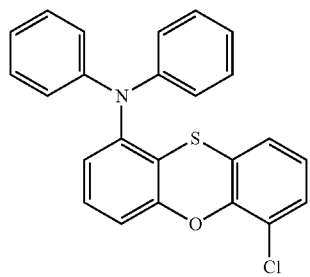
Sub 1-59
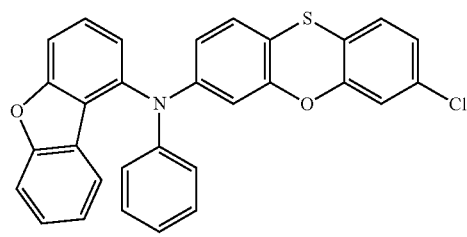
Sub 1-60
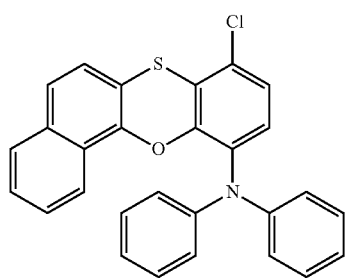
Sub 1-61
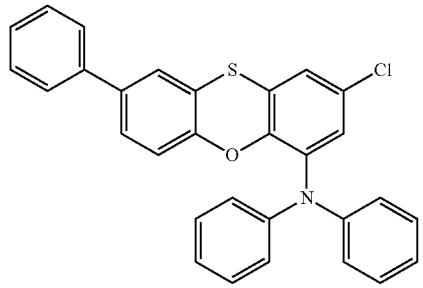
Sub 1-62
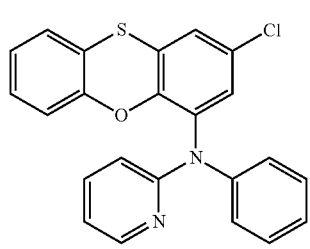
Sub 1-63
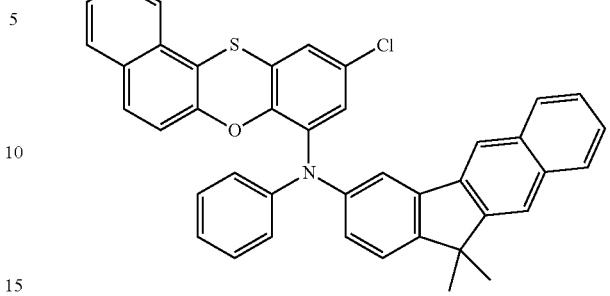
Sub 1-64
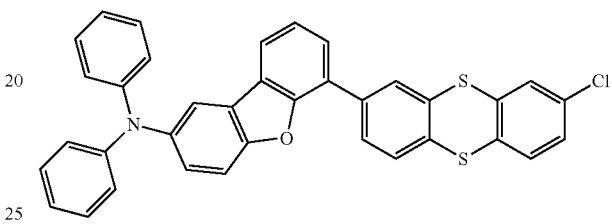
Sub 1-65
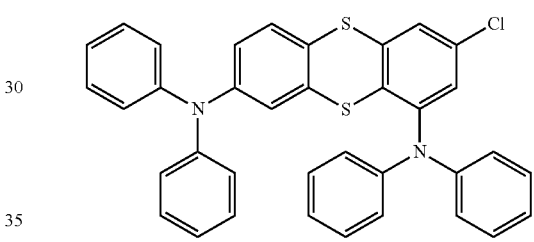
Sub 1-66
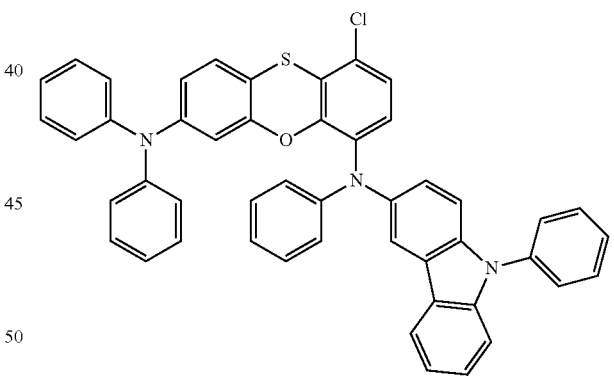
Sub 1-67
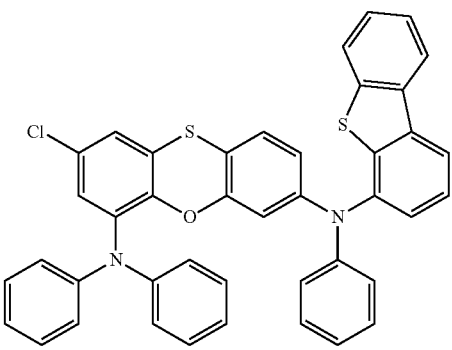

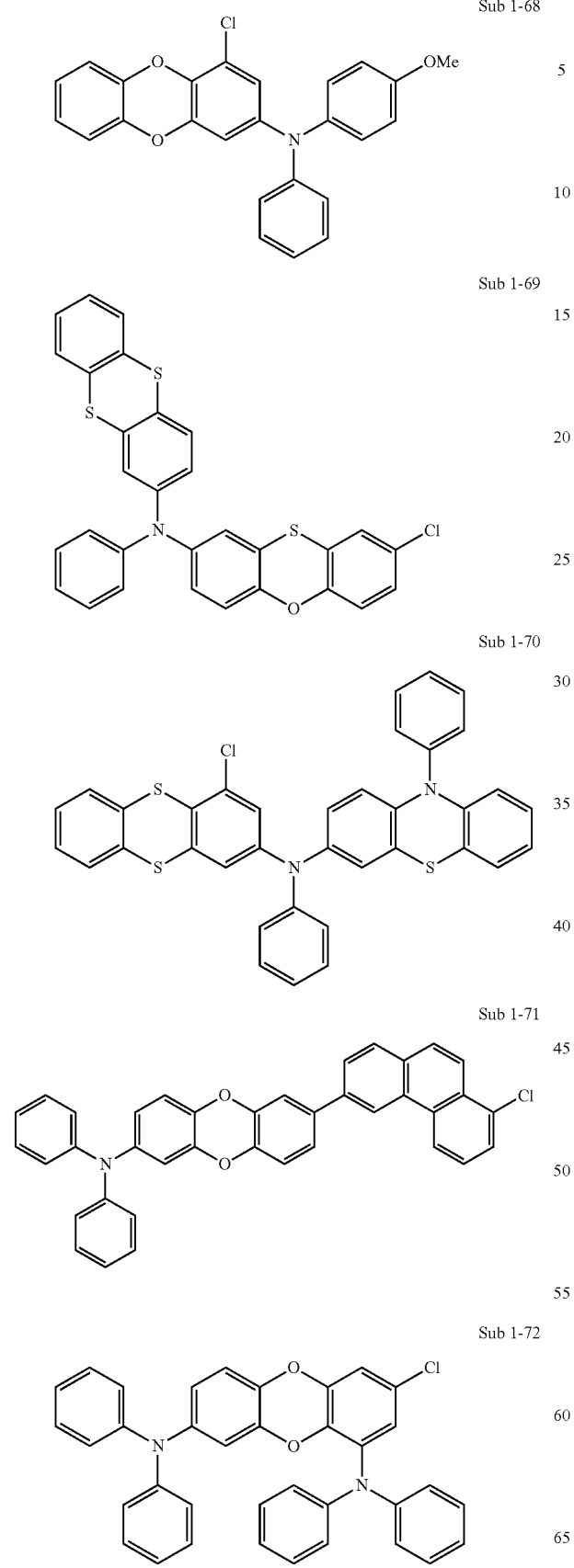
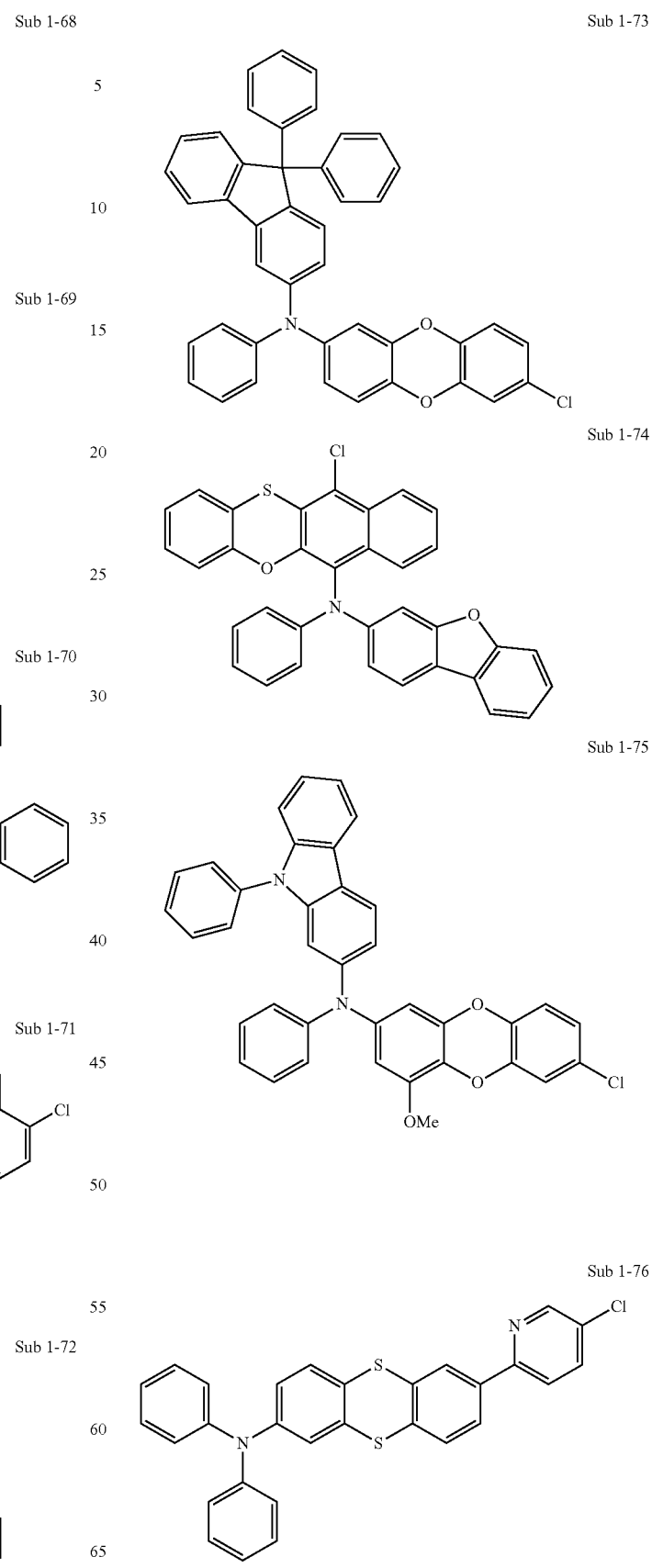

Sub 1-77

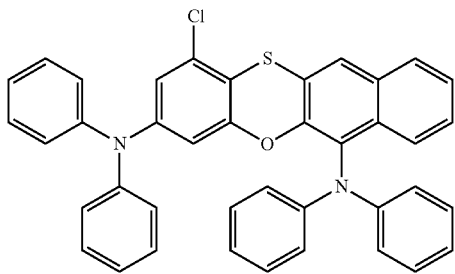

FD-MS (Field Desorption-Mass Spectrometry) values of compounds belong to Sub 1-A and Sub 1-B are shown in Table 1 below.

TABLE 1

| Compound | FD-MS |
| --- | --- |
| Sub 1-1 | m/z = 401.06 ($C_{24}H_{16}ClNOS$ = 401.91) |
| Sub 1-2 | m/z = 401.06 ($C_{24}H_{16}ClNOS$ = 401.91) |
| Sub 1-3 | m/z = 501.10 ($C_{32}H_{20}ClNOS$ = 502.03) |
| Sub 1-4 | m/z = 451.08 ($C_{28}H_{18}ClNOS$ = 451.97) |
| Sub 1-5 | m/z = 451.08 ($C_{28}H_{18}ClNOS$ = 451.97) |
| Sub 1-6 | m/z = 401.06 ($C_{24}H_{16}ClNOS$ = 401.91) |
| Sub 1-7 | m/z = 401.06 ($C_{24}H_{16}ClNOS$ = 401.91) |
| Sub 1-8 | m/z = 401.06 ($C_{24}H_{16}ClNOS$ = 401.91) |
| Sub 1-9 | m/z = 517.13 ($C_{33}H_{24}ClNOS$ = 518.07) |
| Sub 1-10 | m/z = 401.06 ($C_{24}H_{16}ClNOS$ = 401.91) |
| Sub 1-11 | m/z = 491.07 ($C_{30}H_{18}ClNOS$ = 491.99) |
| Sub 1-12 | m/z = 507.05 ($C_{30}H_{18}ClNOS_2$ = 508.05) |
| Sub 1-13 | m/z = 491.07 ($C_{30}H_{18}ClNO_2S$ = 491.99) |
| Sub 1-14 | m/z = 491.07 ($C_{30}H_{18}ClNO_2S$ = 491.99) |
| Sub 1-15 | m/z = 417.04 ($C_{24}H_{16}ClNS_2$ = 417.97) |
| Sub 1-16 | m/z = 385.09 ($C_{24}H_{16}ClNO_2$ = 385.85) |
| Sub 1-17 | m/z = 569.10 ($C_{36}H_{24}ClNS_2$ = 570.17) |
| Sub 1-18 | m/z = 417.04 ($C_{24}H_{16}ClNS_2$ = 417.97) |
| Sub 1-19 | m/z = 385.09 ($C_{24}H_{16}ClNO_2$ = 385.85) |
| Sub 1-20 | m/z = 385.09 ($C_{24}H_{16}ClNO_2$ = 385.85) |
| Sub 1-21 | m/z = 417.04 ($C_{24}H_{16}ClNS_2$ = 417.97) |
| Sub 1-22 | m/z = 385.09 ($C_{24}H_{16}ClNO_2$ = 385.85) |
| Sub 1-23 | m/z = 523.03 ($C_{30}H_{18}ClNS_3$ = 524.11) |
| Sub 1-24 | m/z = 523.03 ($C_{30}H_{18}ClNS_3$ = 524.11) |
| Sub 1-25 | m/z = 385.09 ($C_{24}H_{16}ClNO_2$ = 385.85) |
| Sub 1-26 | m/z = 491.07 ($C_{30}H_{18}ClNO_2S$ = 491.99) |
| Sub 1-27 | m/z = 417.04 ($C_{24}H_{16}ClNS_2$ = 417.97) |
| Sub 1-28 | m/z = 401.06 ($C_{24}H_{16}ClNOS$ = 401.91) |
| Sub 1-29 | m/z = 491.07 ($C_{30}H_{18}ClNO_2S$ = 491.99) |
| Sub 1-30 | m/z = 523.03 ($C_{30}H_{18}ClNS_3$ = 524.11) |
| Sub 1-31 | m/z = 507.05 ($C_{30}H_{18}ClNOS_2$ = 508.05) |
| Sub 1-32 | m/z = 385.09 ($C_{24}H_{16}ClNO_2$ = 385.85) |
| Sub 1-33 | m/z = 427.08 ($C_{26}H_{18}ClNOS$ = 427.95) |
| Sub 1-34 | m/z = 477.10 ($C_{30}H_{20}ClNOS$ = 478.01) |
| Sub 1-35 | m/z = 477.10 ($C_{30}H_{20}ClNOS$ = 478.01) |
| Sub 1-36 | m/z = 527.11 ($C_{34}H_{22}ClNOS$ = 528.07) |
| Sub 1-37 | m/z = 451.08 ($C_{28}H_{18}ClNOS$ = 451.97) |
| Sub 1-38 | m/z = 451.08 ($C_{28}H_{18}ClNOS$ = 451.97) |
| Sub 1-39 | m/z = 523.03 ($C_{30}H_{18}ClNS_3$ = 524.11) |
| Sub 1-40 | m/z = 493.07 ($C_{30}H_{20}ClNS_2$ = 494.07) |
| Sub 1-41 | m/z = 390.12 ($C_{24}H_{11}D_5ClNO_2$ = 390.88) |
| Sub 1-42 | m/z = 451.08 ($C_{28}H_{18}ClNOS$ = 451.97) |
| Sub 1-43 | m/z = 527.11 ($C_{34}H_{22}ClNOS$ = 528.07) |
| Sub 1-44 | m/z = 527.11 ($C_{34}H_{22}ClNOS$ = 528.07) |
| Sub 1-45 | m/z = 557.07 ($C_{34}H_{20}ClNOS_2$ = 558.11) |
| Sub 1-46 | m/z = 587.17 ($C_{40}H_{26}ClNO_2$ = 588.10) |
| Sub 1-47 | m/z = 410.08 ($C_{25}H_{15}ClN_2O_2$ = 410.86) |
| Sub 1-48 | m/z = 513.12 ($C_{32}H_{20}ClN_3O_2$ = 513.98) |
| Sub 1-49 | m/z = 632.11 ($C_{40}H_{25}ClN_2S_2$ = 633.22) |
| Sub 1-50 | m/z = 401.06 ($C_{24}H_{16}ClNOS$ = 401.91) |
| Sub 1-51 | m/z = 567.12 ($C_{35}H_{22}ClN_3OS$ = 568.09) |
| Sub 1-52 | m/z = 419.05 ($C_{24}H_{15}ClFNOS$ = 419.90) |
| Sub 1-53 | m/z = 507.05 ($C_{30}H_{18}ClNOS_2$ = 508.05) |
| Sub 1-54 | m/z = 475.10 ($C_{30}H_{18}ClNO_3$ = 475.93) |
| Sub 1-55 | m/z = 673.18 ($C_{47}H_{28}ClNO_2$ = 674.20) |

TABLE 1-continued

| Compound | FD-MS |
| --- | --- |
| Sub 1-56 | m/z = 783.18 ($C_{53}H_{34}ClNS_2$ = 784.43) |
| Sub 1-57 | m/z = 477.10 ($C_{30}H_{20}ClNOS$ = 478.01) |
| Sub 1-58 | m/z = 401.06 ($C_{24}H_{16}ClNOS$ = 401.91) |
| Sub 1-59 | m/z = 491.07 ($C_{30}H_{18}ClNO_2S$ = 491.99) |
| Sub 1-60 | m/z = 451.08 ($C_{28}H_{18}ClNOS$ = 451.97) |
| Sub 1-61 | m/z = 477.10 ($C_{30}H_{20}ClNOS$ = 478.01) |
| Sub 1-62 | m/z = 402.06 ($C_{23}H_{15}ClN_2OS$ = 402.90) |
| Sub 1-63 | m/z = 617.16 ($C_{41}H_{28}ClNOS$ = 618.19) |
| Sub 1-64 | m/z = 583.08 ($C_{36}H_{22}ClNOS_2$ = 584.15) |
| Sub 1-65 | m/z = 584.11 ($C_{36}H_{25}ClN_2S_2$ = 585.18) |
| Sub 1-66 | m/z = 733.20 ($C_{48}H_{32}ClN_3OS$ = 734.31) |
| Sub 1-67 | m/z = 674.13 ($C_{42}H_{27}ClN_2OS_2$ = 675.26) |
| Sub 1-68 | m/z = 415.10 ($C_{25}H_{18}ClNO_3$ = 415.87) |
| Sub 1-69 | m/z = 539.02 ($C_{30}H_{18}ClNOS_3$ = 540.11) |
| Sub 1-70 | m/z = 614.07 ($C_{36}H_{23}ClN_2S_3$ = 615.22) |
| Sub 1-71 | m/z = 561.15 ($C_{38}H_{24}ClNO_2$ = 562.07) |
| Sub 1-72 | m/z = 552.16 ($C_{36}H_{25}ClN_2O_2$ = 553.06) |
| Sub 1-73 | m/z = 625.18 ($C_{43}H_{28}ClNO_2$ = 626.15) |
| Sub 1-74 | m/z = 541.09 ($C_{34}H_{20}ClNO_2S$ = 542.05) |
| Sub 1-75 | m/z = 580.16 ($C_{37}H_{25}ClN_2O_3$ = 581.07) |
| Sub 1-76 | m/z = 494.07 ($C_{28}H_{19}ClN_2S_2$ = 495.06) |
| Sub 1-77 | m/z = 618.15 ($C_{40}H_{27}ClN_2OS$ = 619.18) |

Sub 1-A or Sub 1-B of Reaction Scheme 1 may be synthesized by the reaction route of the following Reaction Scheme 3 or 4, but are not limited thereto.

<Reaction Scheme 3>

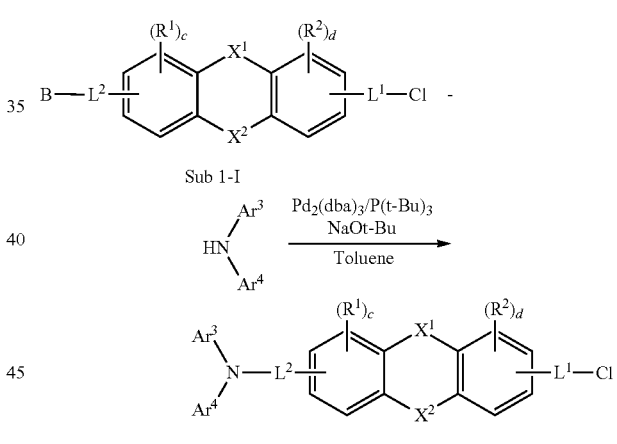

<Reaction Scheme 4>

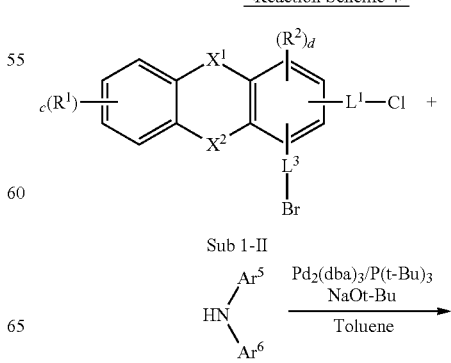

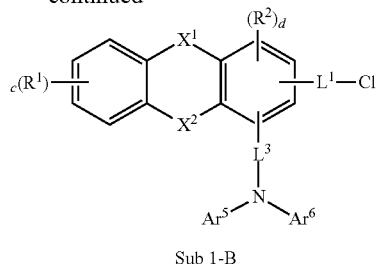

Sub 1-B

Synthesis Example of Sub 1-1

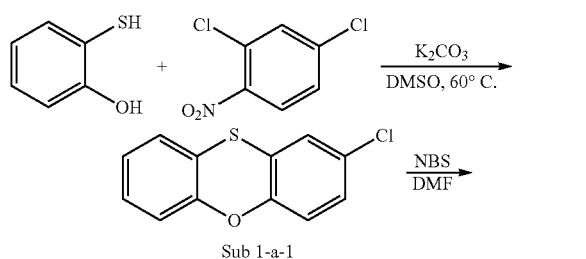

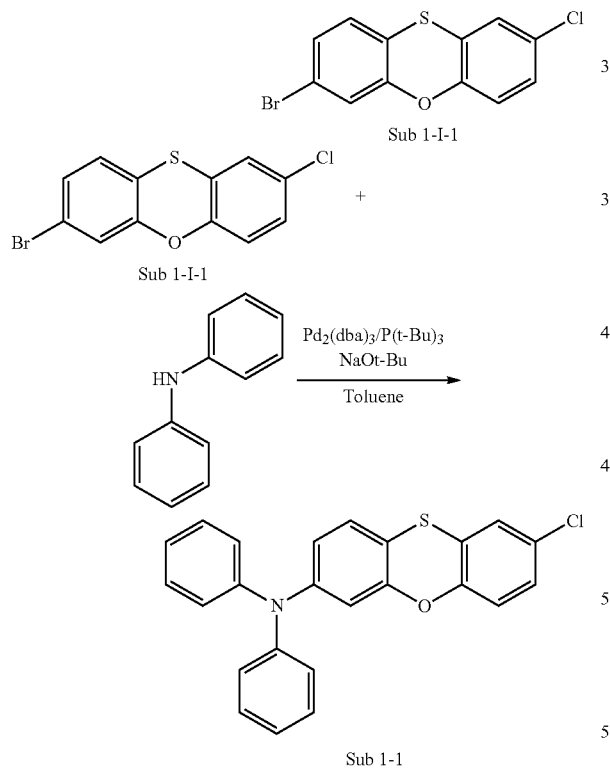

Sub 1-1

(1) Synthesis of Sub 1-a-1

DMSO (320 mL) was added to a mixture of 2,4-dichloro-1-nitrobenzene (15.80 g, 82.29 mmol), 2-sulfanylphenol (12.46 g, 98.75 mmol) and $K_2CO_3$ (28.43 g, 205.73 mmol) under a nitrogen stream. Then, the mixture was stirred at 60° C. for 3 hours. When the reaction is complete, the reaction product was cooled to room temperature and extracted with ethyl acetate and a saturated aqueous NaCl solution. An extracted organic layer was dried over $MgSO_4$ and concentrated. Then, the concentrate was separated by a silica gel column and recrystallized to obtain 13.52 g (yield: 70%) of Sub 1-a-1.

(2) Synthesis of Sub 1-I-1

A solution in which Sub 1-a-1 (13.52 g, 57.61 mmol) was dissolved in DMF (250 mL) was added portionwise to a solution in which NBS (10.77 g, 60.49 mmol) was dissolved in DMF and the mixture was heated and stirred at 60° C. for 5 hours. When the reaction is complete, the reaction product was cooled to room temperature, washed with water, extracted with ethyl acetate, and concentrated. Then, the concentrate was separated by a silica gel column and recrystallized to obtain 12.10 g (yield: 67%) of Sub 1-I-1.

(3) Synthesis of Sub 1-1

Sub 1-I-1 (12.10 g, 38.59 mmol) was dissolved in toluene (200 mL) in a round bottom flask, and diphenylamine (6.53 g, 38.59 mmol), $Pd_2(dba)_3$ (1.06 g, 1.16 mmol), $P(t-Bu)_3$ (50 wt % Sol.) (1.56 mL, 3.86 mmol) and NaOt-Bu (11.12 g, 115.76 mmol) were added to the solution. The mixture was stirred at 65° C. When the reaction is complete, the reaction product was extracted with $CH_2C_{12}$ and water. An organic layer was dried over $MgSO_4$ and concentrated. Then, the concentrate was separated by a silica gel column and recrystallized to obtain 11.48 g (yield: 74%) of Sub 1-1.

Synthesis Example of Sub 1-6

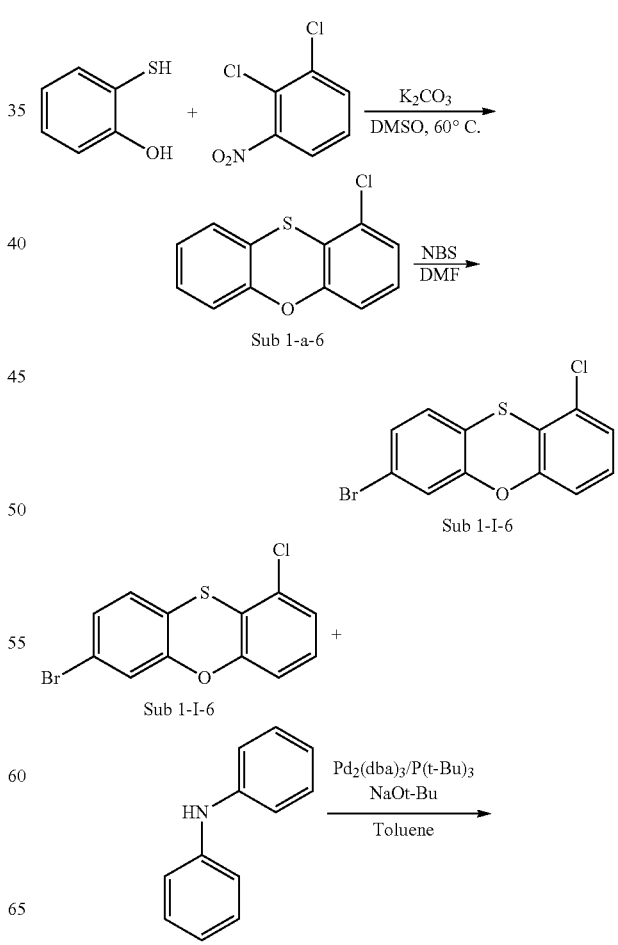

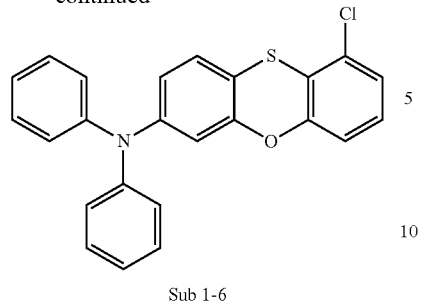

Sub 1-6

(1) Synthesis of Sub 1-a-6

DMSO (200 mL) was added to a mixture of 1,2-dichloro-3-nitrobenzene (10.00 g, 52.08 mmol), 2-sulfanylphenol (7.89 g, 62.50 mmol) and $K_2CO_3$ (18.0 g, 130.21 mmol) under a nitrogen stream. Then, the mixture was stirred at 60° C. for 3 hours. When the reaction is complete, the reaction product was cooled to room temperature and extracted with ethyl acetate and a saturated aqueous NaCl solution. An extracted organic layer was dried over $MgSO_4$ and concentrated. Then, the concentrate was separated by a silica gel column and recrystallized to obtain 6.48 g (yield: 53%) of Sub 1-a-6.

(2) Synthesis of Sub 1-I-6

A solution in which Sub 1-a-6 (6.40 g, 27.61 mmol) was dissolved in DMF (130 mL) was added portionwise to a solution in which NBS (5.16 g, 28.99 mmol) was dissolved in DMF and the mixture was heated and stirred at 60° C. for 5 hours. When the reaction is complete, the reaction product was cooled to room temperature, washed with water, extracted with ethyl acetate, and concentrated. Then, the concentrate was separated by a silica gel column and recrystallized to obtain 6.15 g (yield: 71%) of Sub 1-I-6.

(3) Synthesis of Sub 1-6

Sub 1-I-6 (6.15 g, 19.61 mmol) was dissolved in toluene (150 mL) in a round bottom flask, and diphenylamine (3.32 g, 19.61 mmol), $Pd_2(dba)_3$ (0.54 g, 0.59 mmol), $P(t-Bu)_3$ (50 wt % Sol.) (0.79 mL, 1.96 mmol) and NaOt-Bu (5.65 g, 58.83 mmol) were added to the solution. The mixture was stirred at 65° C. When the reaction is complete, the reaction product was extracted with $CH_2Cl_2$ and water. An organic layer was dried over $MgSO_4$ and concentrated. Then, the concentrate was separated by a silica gel column and recrystallized to obtain 4.97 g (yield: 63%) of Sub 1-6.

Synthesis Example of Sub 1-9

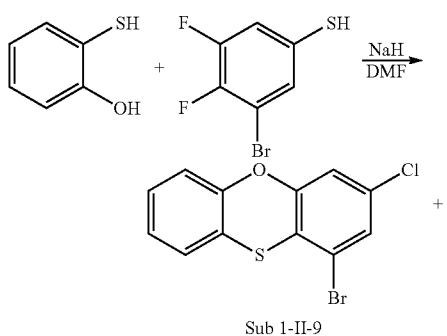

Sub 1-II-9

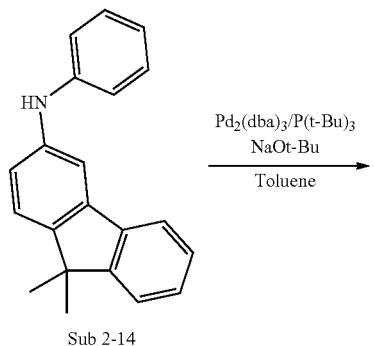

Sub 2-14

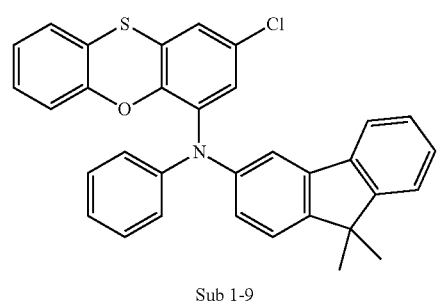

Sub 1-9

(1) Synthesis of Sub 1-II-9

2-sulfanylphenol (12.50 g, 99.07 mmol), 2-sulfanylphenol (12.46 g, 98.75 mmol), 1-bromo-5-chloro-2,3-difluorobenzene (22.53 g, 99.07 mmol), NaH (0.12 g, 4.95 mmol) and DMF 230 mL were mixed under a nitrogen stream. Then, the mixture was stirred at 100° C. for 12 hours. When the reaction is complete, the reaction product was extracted with ethyl acetate and water. An extracted organic layer was dried over $MgSO_4$ and concentrated. Then, the concentrate was separated by a silica gel column and recrystallized to obtain 15.84 g (yield: 51%) of Sub 1-II-9.

(2) Synthesis of Sub 1-9

Sub 1-II-9 (15.8 g, 50.38 mmol) was dissolved in toluene (250 mL) in a round bottom flask, and Sub 2-14 (14.38 g, 50.38 mmol), $Pd_2(dba)_3$ (1.38 g, 1.51 mmol), $P(t-Bu)_3$ (50 wt % Sol.) (2.04 mL, 5.04 mmol) and NaOt-Bu (14.53 g, 151.15 mmol) were added to the solution. The mixture was stirred at 65° C. When the reaction is complete, the reaction product was extracted with $CH_2Cl_2$ and water. An organic layer was dried over $MgSO_4$ and concentrated. Then, the concentrate was separated by a silica gel column and recrystallized to obtain 17.23 g (yield: 66%) of Sub 1-9.

Synthesis Example of Sub 1-25

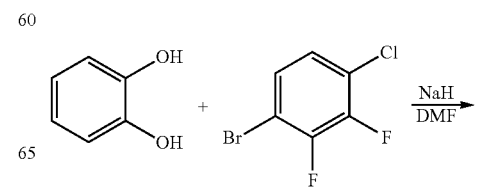

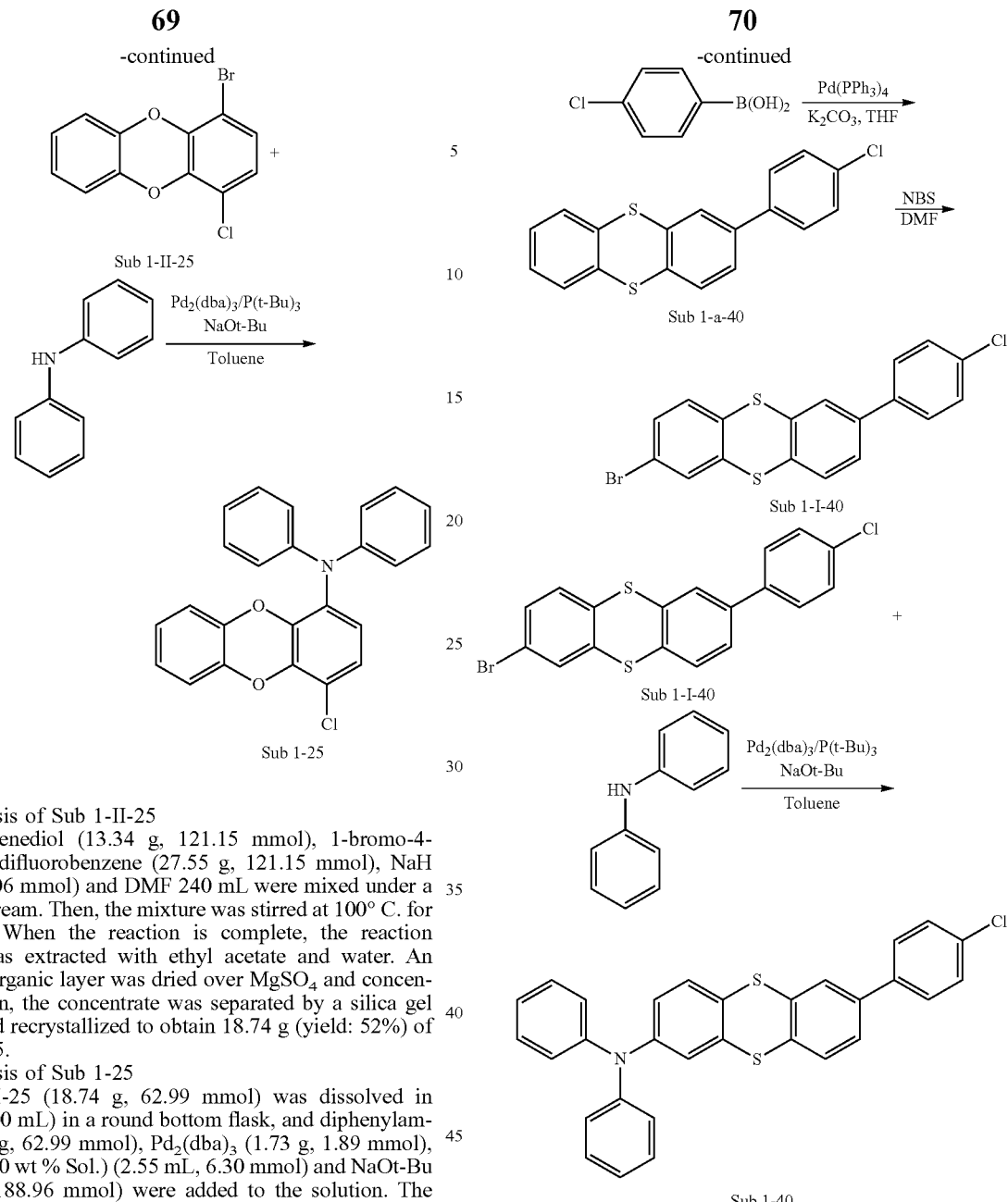

(1) Synthesis of Sub 1-II-25

1,2-benzenediol (13.34 g, 121.15 mmol), 1-bromo-4-chloro-2,3-difluorobenzene (27.55 g, 121.15 mmol), NaH (0.15 g, 6.06 mmol) and DMF 240 mL were mixed under a nitrogen stream. Then, the mixture was stirred at 100° C. for 12 hours. When the reaction is complete, the reaction product was extracted with ethyl acetate and water. An extracted organic layer was dried over $MgSO_4$ and concentrated. Then, the concentrate was separated by a silica gel column and recrystallized to obtain 18.74 g (yield: 52%) of Sub 1-II-25.

(2) Synthesis of Sub 1-25

Sub 1-II-25 (18.74 g, 62.99 mmol) was dissolved in toluene (300 mL) in a round bottom flask, and diphenylamine (10.66 g, 62.99 mmol), $Pd_2(dba)_3$ (1.73 g, 1.89 mmol), $P(t-Bu)_3$ (50 wt % Sol.) (2.55 mL, 6.30 mmol) and NaOt-Bu (18.16 g, 188.96 mmol) were added to the solution. The mixture was stirred at 65° C. When the reaction is complete, the reaction product was extracted with $CH_2C_{12}$ and water. An organic layer was dried over $MgSO_4$ and concentrated. Then, the concentrate was separated by a silica gel column and recrystallized to obtain 19.20 g (yield: 79%) of Sub 1-25.

Synthesis Example of Sub 1-40

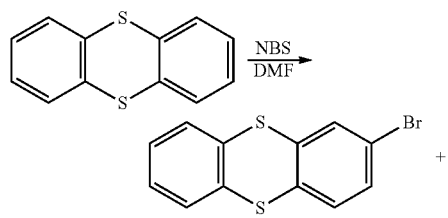

(1) Synthesis of Sub 1-a-40

A solution in which thianthrene (11.0 g, 50.85 mmol) was dissolved in DMF (200 mL) was added portionwise to a solution in which NBS (9.96 g, 55.94 mmol) was dissolved in DMF and the mixture was heated and stirred at 60° C. for 5 hours. When the reaction is complete, the reaction product was cooled to room temperature, washed with water, extracted with ethyl acetate, and concentrated. Then, the concentrate was separated by a silica gel column and recrystallized to obtain 10.51 g (yield: 70%) of 2-bromothianthrene.

Then, 4-chlorophenylboronic acid (5.57 g, 35.60 mmol) was added to 2-bromothianthrene (10.51 g, 35.60 mmol) under a nitrogen stream and the mixture was dissolved in THF (120 mL). Thereafter, $Pd(PPh_3)_4$ (2.26 g, 1.78 mmol) and $K_2CO_3$ (14.76 g, 106.81 mmol) were added to the solution, the mixture was refluxed for 24 hours. When the reaction is complete, the reaction product was cooled to room temperature and extracted with CH₂Cl₂ and water. An organic layer was dried over MgSO₄ and concentrated. Then, the concentrate was separated by a silica gel column and recrystallized to obtain 8.73 g (yield: 75%) of Sub 1-a-40.

(2) Synthesis of Sub 1-I-40

A solution in which Sub 1-a-40 (8.73 g, 26.71 mmol) was dissolved in DMF (150 mL) was added portionwise to a solution in which NBS (4.99 g, 28.04 mmol) was dissolved in DMF and the mixture was heated and stirred at 60° C. for 5 hours. When the reaction is complete, the reaction product was cooled to room temperature, washed with water, extracted with ethyl acetate, and concentrated. Then, the concentrate was separated by a silica gel column and recrystallized to obtain 6.72 g (yield: 62%) of Sub 1-I-40.

(3) Synthesis of Sub 1-40

Sub 1-I-40 (6.72 g, 16.56 mmol) was dissolved in toluene (150 mL) in a round bottom flask, and diphenylamine (2.80 g, 16.56 mmol), Pd₂(dba)₃ (0.45 g, 0.50 mmol), P(t-Bu)₃ (50 wt % Sol.) (0.67 mL, 1.66 mmol) and NaOt-Bu (4.77 g, 49.69 mmol) were added to the solution. The mixture was stirred at 65° C. When the reaction is complete, the reaction product was extracted with CH₂C₁₂ and water. An organic layer was dried over MgSO₄ and concentrated. Then, the concentrate was separated by a silica gel column and recrystallized to obtain 4.75 g (yield: 58%) of Sub 1-40.

Synthesis Example of Sub 1-45

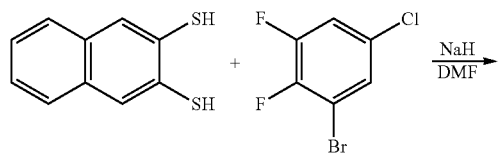

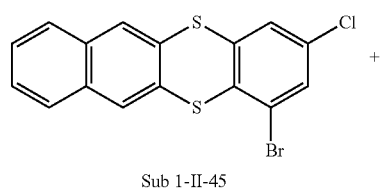

Sub 1-II-45

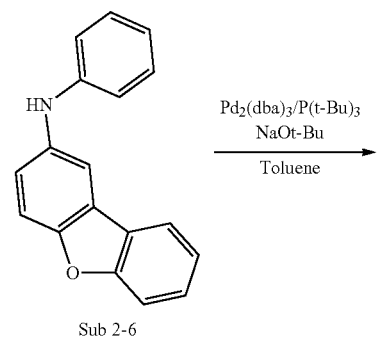

Sub 2-6

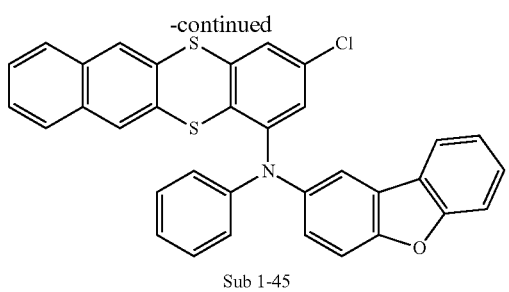

Sub 1-45

(1) Synthesis of Sub 1-II-45

2,3-Naphthalenedithiol (9.65 g, 50.18 mmol), 1-bromo-5-chloro-2,3-difluorobenzene (11.41 g, 50.18 mmol), NaH (0.06 g, 2.51 mmol) and DMF 120 mL were mixed under a nitrogen stream. Then, the mixture was stirred at 100° C. for 12 hours. When the reaction is complete, the reaction product was extracted with ethyl acetate and water. An organic layer was dried over MgSO₄ and concentrated. Then, the concentrate was separated by a silica gel column and recrystallized to obtain 11.05 g (yield: 58%) of Sub 1-II-45.

(2) Synthesis of Sub 1-45

Sub 1-II-45 (11.05 g, 29.10 mmol) was dissolved in toluene (200 mL) in a round bottom flask, and Sub 2-6 (7.55 g, 29.10 mmol), Pd₂(dba)₃ (0.80 g, 0.87 mmol), P(t-Bu)₃ (50 wt % Sol.) (1.18 mL, 2.91 mmol) and NaOt-Bu (8.39 g, 87.30 mmol) were added to the solution. The mixture was stirred at 65° C. When the reaction is complete, the reaction product was extracted with CH₂C₁₂ and water. An organic layer was dried over MgSO₄ and concentrated. Then, the concentrate was separated by a silica gel column and recrystallized to obtain 11.37 g (yield: 70%) of Sub 1-45.

2. Exemplary Compounds and Synthesis Examples of Sub 2

Compounds belong to Sub 2 of Reaction Scheme 1 are as follows, but are not limited thereto.

Sub 2-1

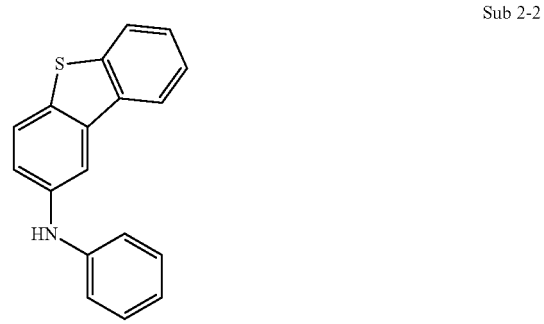

Sub 2-2

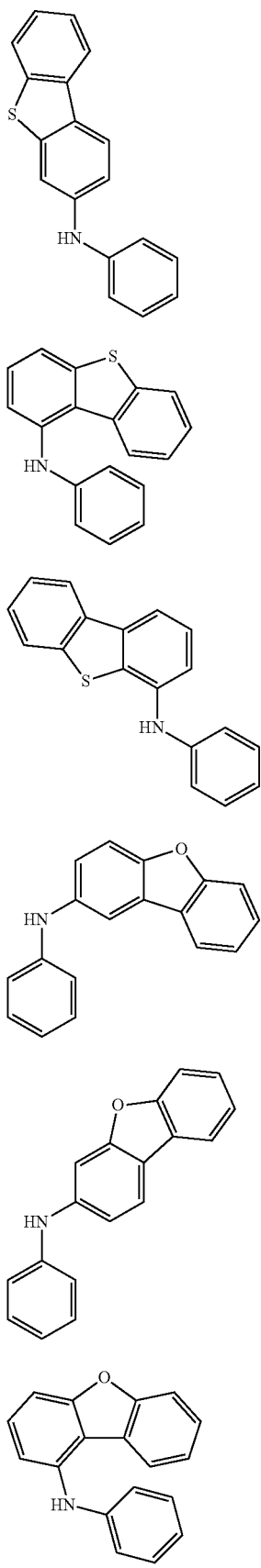
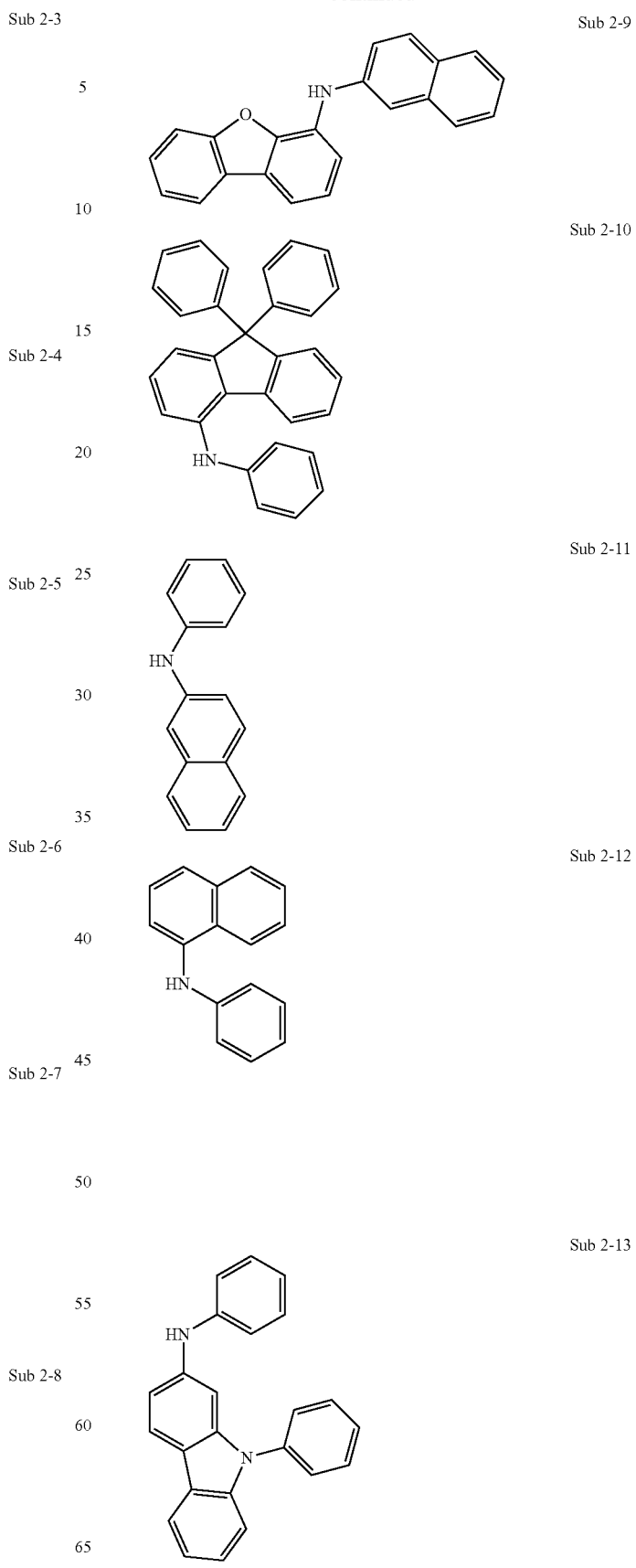

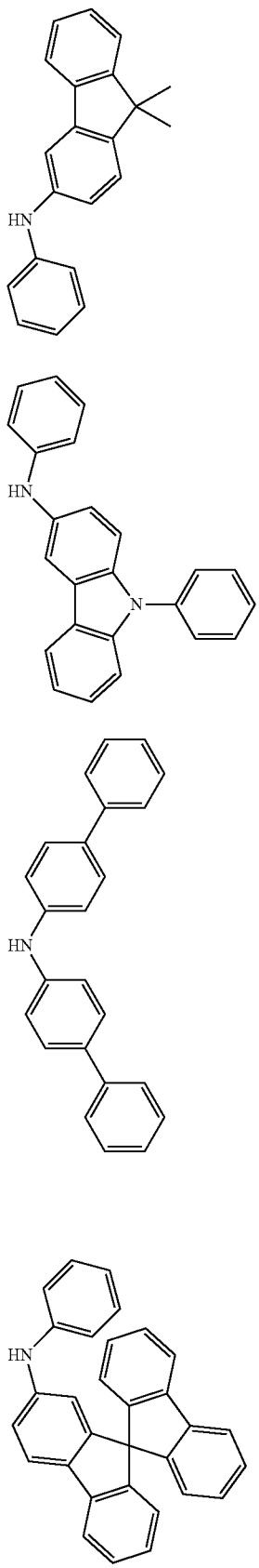
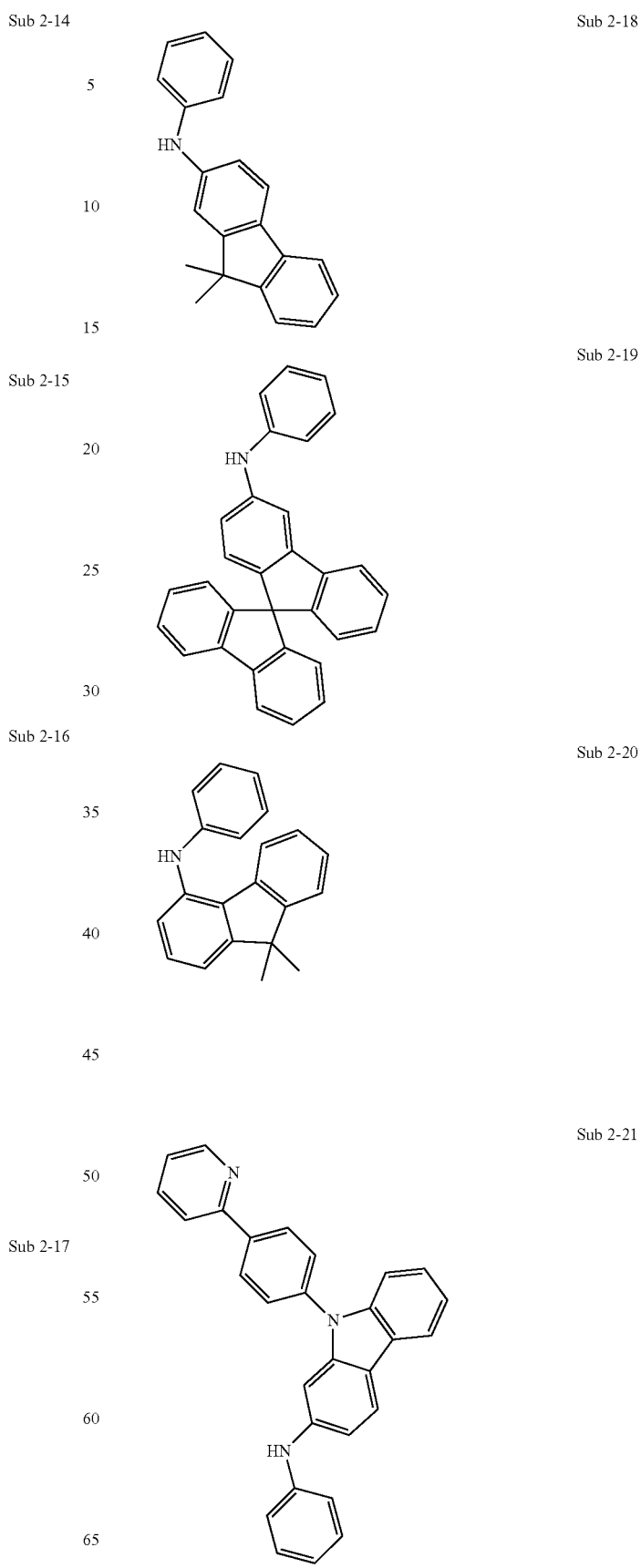

Sub 2-22
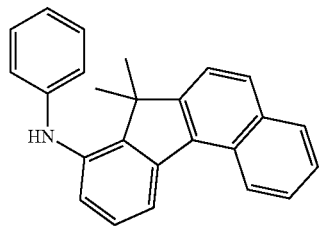
Sub 2-23
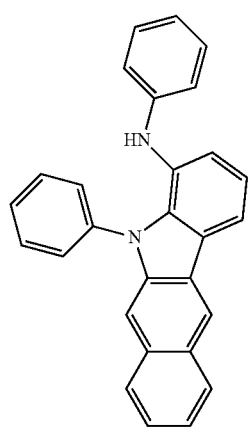
Sub 2-24
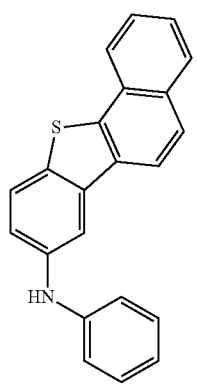
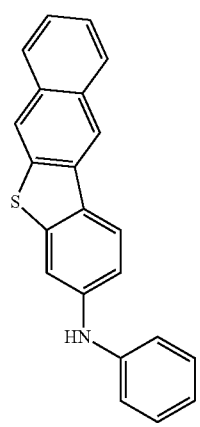
Sub 2-26
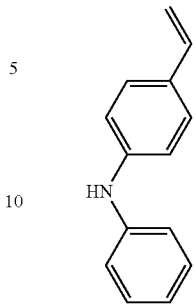
Sub 2-27
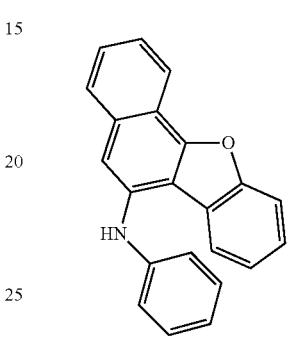
Sub 2-28
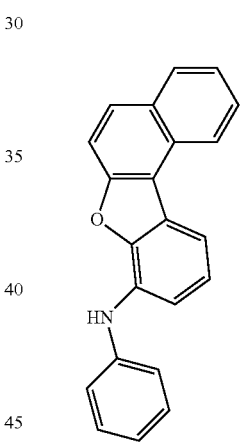
Sub 2-25
Sub 2-29
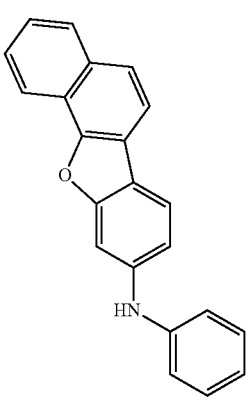

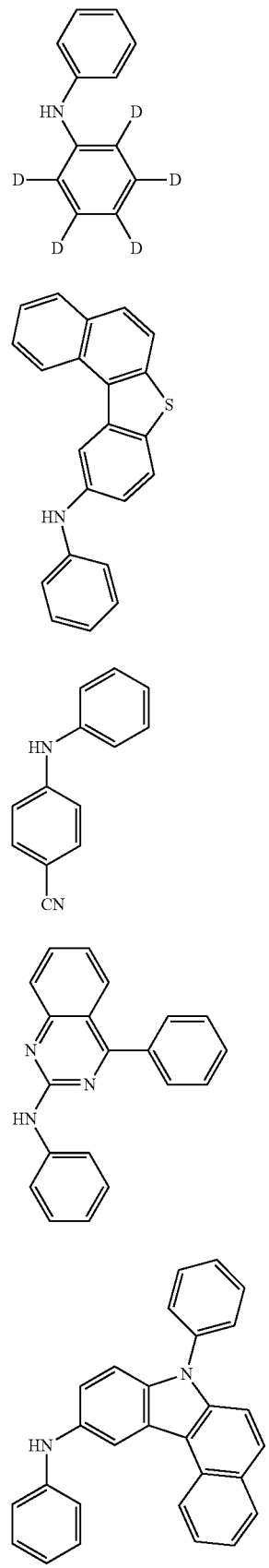
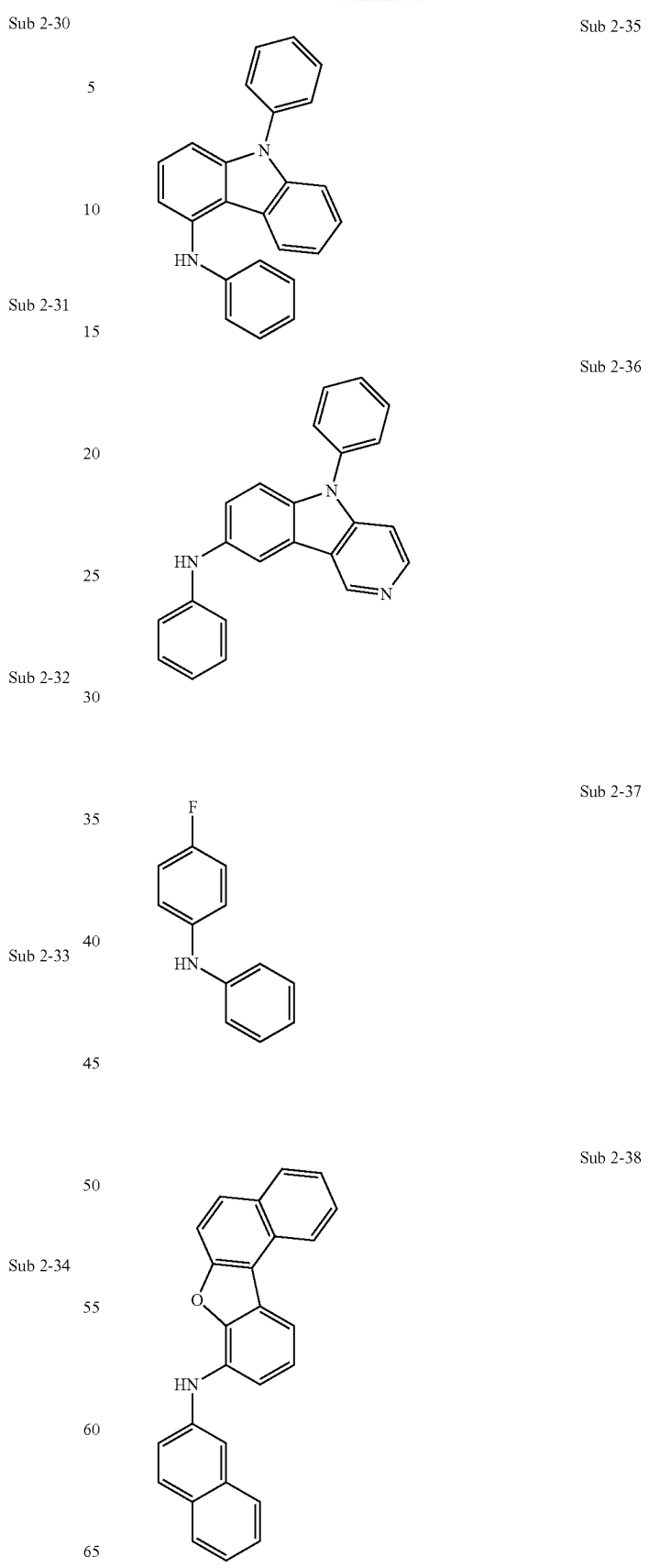

-continued
Sub 2-39 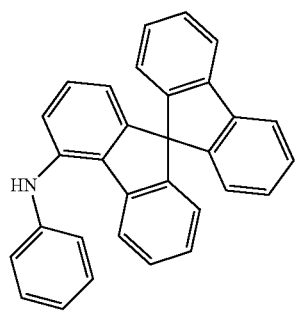
Sub 2-40 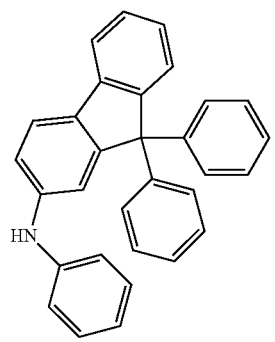
Sub 2-41 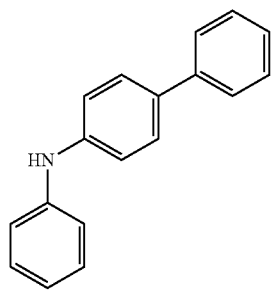
Sub 2-42 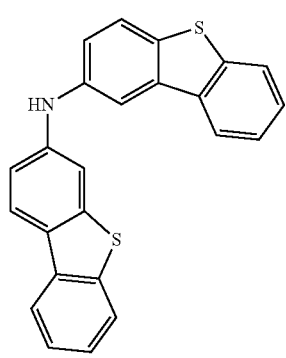
-continued
Sub 2-43 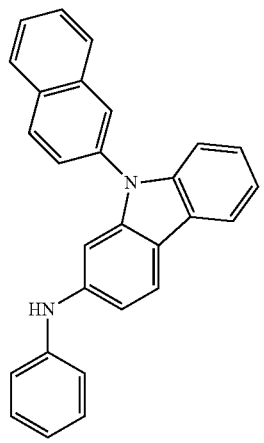
Sub 2-44 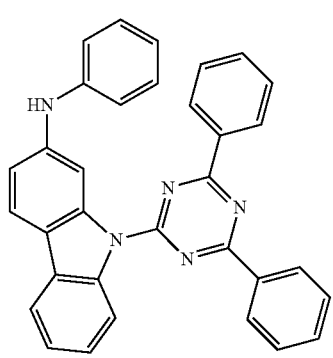
Sub 2-45 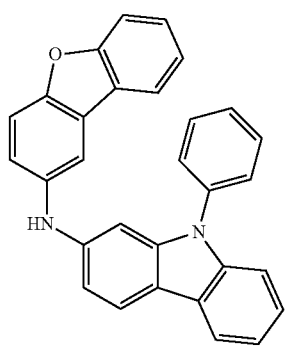
Sub 2-46 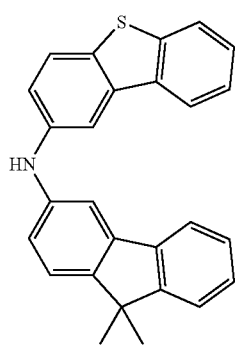

-continued

Sub 2-47
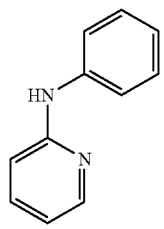

Sub 2-48
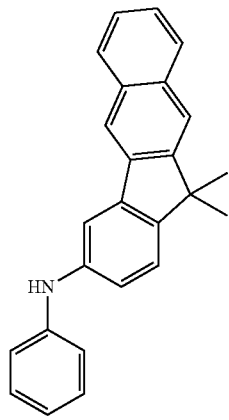

Sub 2-49
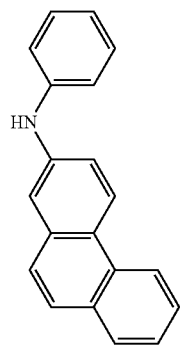

Sub 2-50
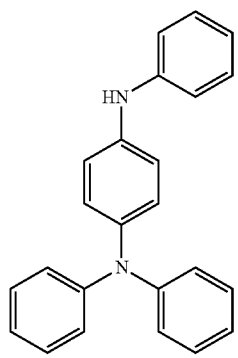

Sub 2-51
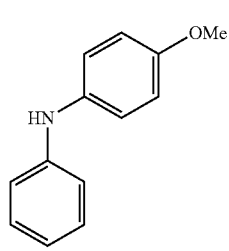

-continued

Sub 2-52
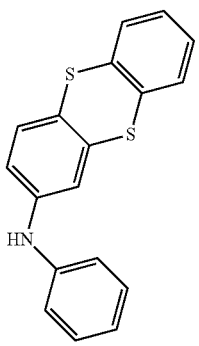

Sub 2-53
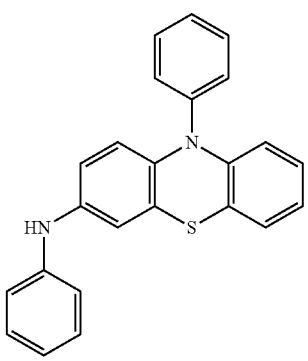

Sub 2-54
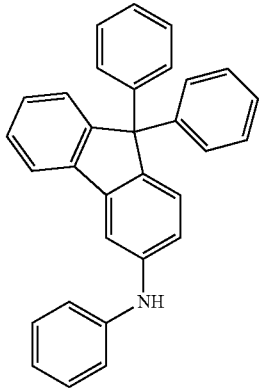

FD-MS values of compounds belong to Sub 2 are shown in Table 2 below.

TABLE 2

| Compound | FD-MS |
| --- | --- |
| Sub 2-1 | m/z = 169.09 ($C_{12}H_{11}N$ = 169.23) |
| Sub 2-2 | m/z = 275.08 ($C_{18}H_{13}NS$ = 275.37) |
| Sub 2-3 | m/z = 275.08 ($C_{18}H_{13}NS$ = 275.37) |
| Sub 2-4 | m/z = 275.08 ($C_{18}H_{13}NS$ = 275.37) |
| Sub 2-5 | m/z = 275.08 ($C_{18}H_{13}NS$ = 275.37) |
| Sub 2-6 | m/z = 259.10 ($C_{18}H_{13}NO$ = 259.31) |
| Sub 2-7 | m/z = 259.10 ($C_{18}H_{13}NO$ = 259.31) |
| Sub 2-8 | m/z = 259.10 ($C_{18}H_{13}NO$ = 259.31) |
| Sub 2-9 | m/z = 309.12 ($C_{22}H_{15}NO$ = 309.37) |
| Sub 2-10 | m/z = 409.18 ($C_{31}H_{23}N$ = 409.53) |
| Sub 2-11 | m/z = 219.10 ($C_{16}H_{13}N$ = 219.29) |
| Sub 2-12 | m/z = 219.10 ($C_{16}H_{13}N$ = 219.29) |
| Sub 2-13 | m/z = 334.15 ($C_{24}H_{18}N$ = 334.42) |
| Sub 2-14 | m/z = 285.15 ($C_{21}H_{19}N$ = 285.39) |
| Sub 2-15 | m/z = 334.15 ($C_{24}H_{18}N$ = 334.42) |
| Sub 2-16 | m/z = 321.15 ($C_{24}H_{19}N$ = 321.42) |
| Sub 2-17 | m/z = 407.17 ($C_{31}H_{21}N$ = 407.52) |

TABLE 2-continued

| Compound | FD-MS |
|---|---|
| Sub 2-18 | m/z = 285.15 ($C_{21}H_{19}N$ = 285.39) |
| Sub 2-19 | m/z = 407.17 ($C_{31}H_{21}N$ = 407.52) |
| Sub 2-20 | m/z = 285.15 ($C_{21}H_{19}N$ = 285.39) |
| Sub 2-21 | m/z = 411.17 ($C_{29}H_{21}N_3$ = 411.51) |
| Sub 2-22 | m/z = 335.17 ($C_{25}H_{21}N$ = 335.45) |
| Sub 2-23 | m/z = 384.16 ($C_{28}H_{20}N$ = 384.48) |
| Sub 2-24 | m/z = 325.09 ($C_{22}H_{15}NS$ = 325.43) |
| Sub 2-25 | m/z = 325.09 ($C_{22}H_{15}NS$ = 325.43) |
| Sub 2-26 | m/z = 195.10 ($C_{14}H_{13}N$ = 195.27) |
| Sub 2-27 | m/z = 309.12 ($C_{22}H_{15}NO$ = 309.37) |
| Sub 2-28 | m/z = 309.12 ($C_{22}H_{15}NO$ = 309.37) |
| Sub 2-29 | m/z = 309.12 ($C_{22}H_{15}NO$ = 309.37) |
| Sub 2-30 | m/z = 174.12 ($C_{12}H_6D_5N$ = 174.26) |
| Sub 2-31 | m/z = 325.09 ($C_{22}H_{15}NS$ = 325.43) |
| Sub 2-32 | m/z = 194.08 ($C_{13}H_{10}N$ = 194.24) |
| Sub 2-33 | m/z = 297.13 ($C_{20}H_{15}N_3$ = 297.36) |
| Sub 2-34 | m/z = 384.16 ($C_{28}H_{20}N$ = 384.48) |
| Sub 2-35 | m/z = 334.15 ($C_{24}H_{18}N$ = 334.42) |
| Sub 2-36 | m/z = 335.14 ($C_{23}H_{17}N_3$ = 335.41) |
| Sub 2-37 | m/z = 187.08 ($C_{12}H_{10}FN$ = 187.22) |
| Sub 2-38 | m/z = 359.13 ($C_{26}H_{17}NO$ = 359.43) |
| Sub 2-39 | m/z = 407.17 ($C_{31}H_{21}N$ = 407.52) |
| Sub 2-40 | m/z = 409.18 ($C_{31}H_{23}N$ = 409.53) |
| Sub 2-41 | m/z = 245.12 ($C_{18}H_{15}N$ = 245.33) |
| Sub 2-42 | m/z = 381.06 ($C_{24}H_{15}NS_2$ = 381.51) |
| Sub 2-43 | m/z = 384.16 ($C_{28}H_{20}N$ = 384.48) |
| Sub 2-44 | m/z = 489.20 ($C_{33}H_{23}NS$ = 489.58) |
| Sub 2-45 | m/z = 424.16 ($C_{30}H_{20}NO$ = 424.50) |
| Sub 2-46 | m/z = 391.14 ($C_{27}H_{21}NS$ = 391.53) |
| Sub 2-47 | m/z = 170.08 ($C_{11}H_{10}N$ = 170.22) |
| Sub 2-48 | m/z = 335.17 ($C_{25}H_{21}N$ = 335.45) |
| Sub 2-49 | m/z = 269.12 ($C_{20}H_{15}N$ = 269.35) |
| Sub 2-50 | m/z = 336.16 ($C_{24}H_{20}N$ = 336.44) |
| Sub 2-51 | m/z = 199.10 ($C_{13}H_{13}NO$ = 199.25) |
| Sub 2-52 | m/z = 307.05 ($C_{18}H_{13}NS_2$ = 307.43) |
| Sub 2-53 | m/z = 366.12 ($C_{24}H_{18}NS$ = 366.48) |
| Sub 2-54 | m/z = 409.18 ($C_{31}H_{23}N$ = 409.53) |

Sub 2 of Reaction Scheme 1 may be synthesized by the reaction route of the following Reaction Scheme 5, but are not limited thereto.

<Reaction Scheme 5>

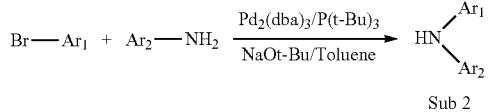

Synthesis Example of Sub 2-2

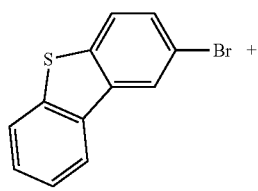

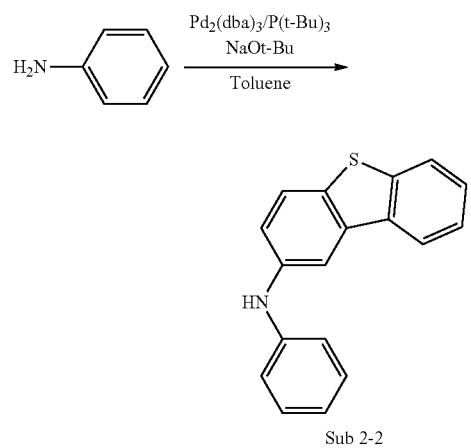

2-bromodibenzo[b,d]thiophene (32.50 g, 123.50 mmol) was putted in a round bottom flask and aniline (12.65 g, 135.85 mmol), $Pd_2(dba)_3$ (3.39 g, 3.71 mmol), $P(t-Bu)_3$ (50 wt % Sol.) (5.0 mL, 12.35 mmol), NaOt-Bu (35.61 g, 370.51 mmol) and toluene 700 mL were added thereto. The mixture was stirred at 80° C. When the reaction was completed, the reaction product was extracted with $CH_2C_{12}$ and water. An organic layer was dried over $MgSO_4$ and concentrated. Then, the concentrate was separated by a silica gel column to obtain 26.53 g (yield: 78%) of the product Sub 2-2.

Synthesis Example of Sub 2-41

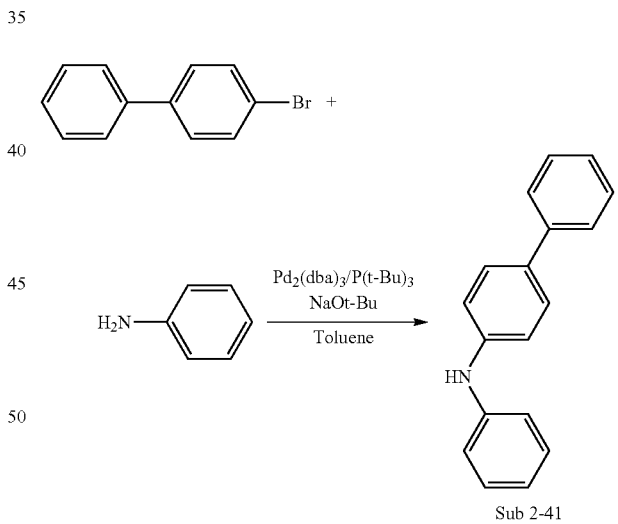

4-bromo-1,1'-biphenyl (25.70 g, 110.25 mmol) was putted in a round bottom flask and aniline (11.29 g, 121.27 mmol), $Pd_2(dba)_3$ (3.03 g, 3.31 mmol), $P(t-Bu)_3$ (50 wt % Sol.) (4.46 mL, 11.02 mmol), NaOt-Bu (31.78 g, 330.75 mmol) and toluene (500 mL) were added thereto. The mixture was stirred at 80° C. When the reaction was completed, the reaction product was extracted with $CH_2C_{12}$ and water. An organic layer was dried over $MgSO_4$ and concentrated. Then, the concentrate was separated by a silica gel column to obtain 22.45 g (yield: 83%) of the product Sub 2-41.

3. Synthesis Example of Final Compound

Synthesis Example of P-1

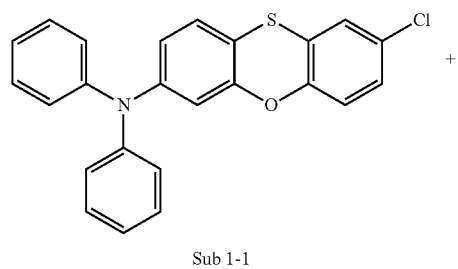

Sub 1-1

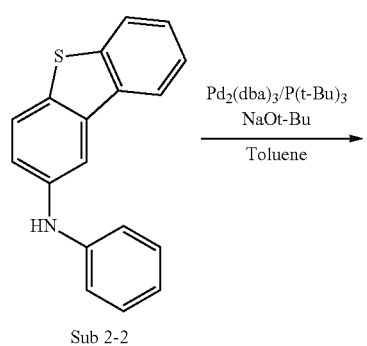

Sub 2-2

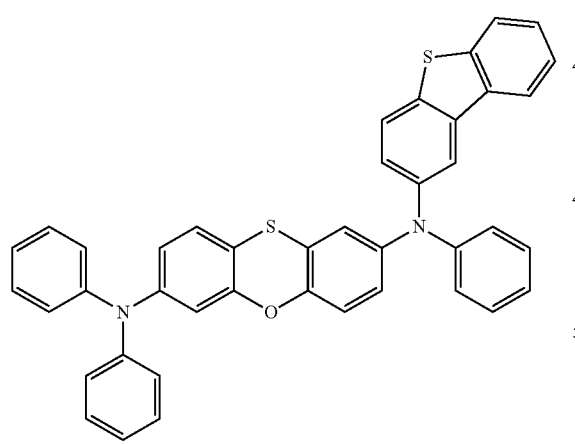

P-1

Sub 1-1 (7.50 g, 18.66 mmol) was dissolved in toluene 120 mL in a round bottom flask and Sub 2-2 (5.15 g, 18.66 mmol), Pd₂(dba)₃ (0.51 g, 0.56 mmol), P(t-Bu)₃ (50 wt % Sol.) (0.76 mL, 1.87 mmol) and NaOt-Bu (5.38 g, 55.98 mmol) were added thereto. The mixture was stirred at 110° C. When the reaction was completed, the reaction product was extracted with CH₂Cl₂ and water. An organic layer was dried over MgSO₄ and concentrated. Then, the concentrate was separated by a silica gel column and sublimated and purified to obtain 8.61 g (yield: 72%) of the product P-1.

Synthesis Example of P-9

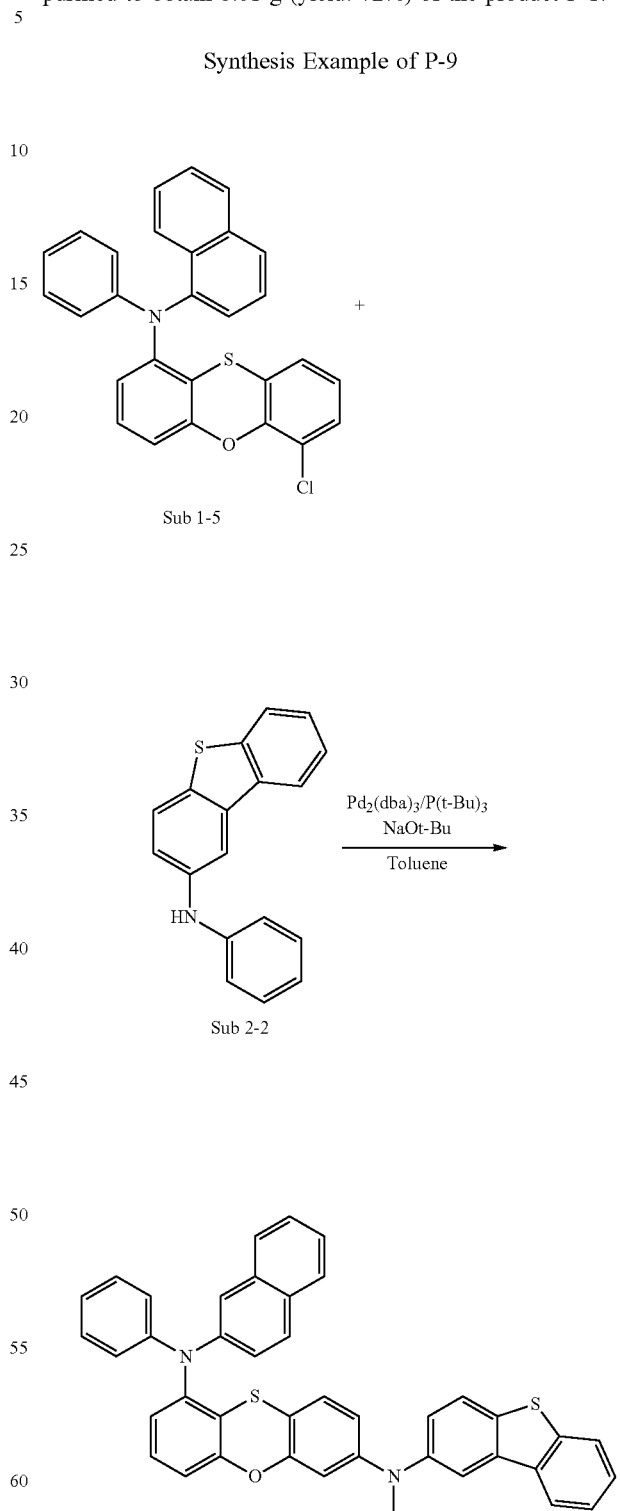

Sub 1-5 (5.83 g, 12.90 mmol) was dissolved in toluene (100 mL), and Sub 2-2 (3.56 g, 12.90 mmol), Pd$_2$(dba)$_3$ (0.35 g, 0.39 mmol), P(t-Bu)$_3$ (50 wt % Sol.) (0.52 mL, 1.29 mmol) and NaOt-Bu (3.72 g, 38.71 mmol) were added to the solution. Then, the reaction was carried out in the same manner as in the synthesis method of P-1 to obtain 6.15 g (yield: 69%) of the product P-9.

Synthesis Example of P-24

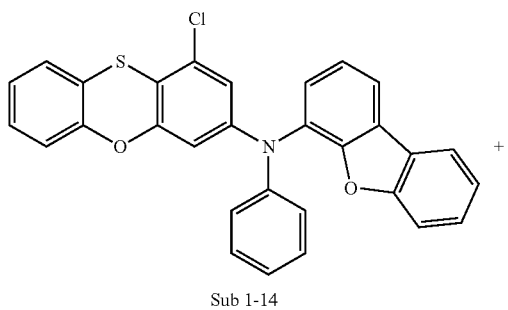

Sub 1-14

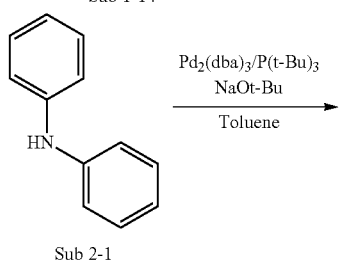

Sub 2-1

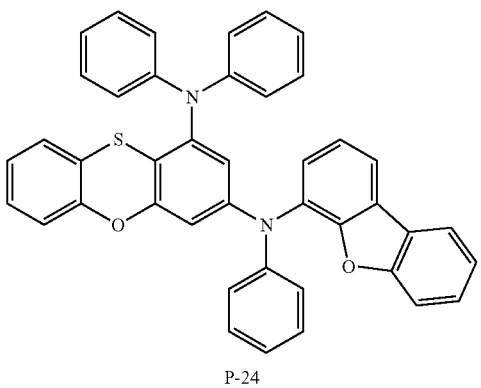

P-24

Sub 1-14 (6.95 g, 14.13 mmol) was dissolved in toluene (110 mL), and Sub 2-1 (2.39 g, 14.13 mmol), Pd$_2$(dba)$_3$ (0.39 g, 0.42 mmol), P(t-Bu)$_3$ (50 wt % Sol.) (0.57 mL, 1.41 mmol) and NaOt-Bu (4.07 g, 42.38 mmol) were added to the solution. Then, the reaction was carried out in the same manner as in the synthesis method of P-1 to obtain 7.06 g (yield: 80%) of the product P-24.

Synthesis Example of P-61

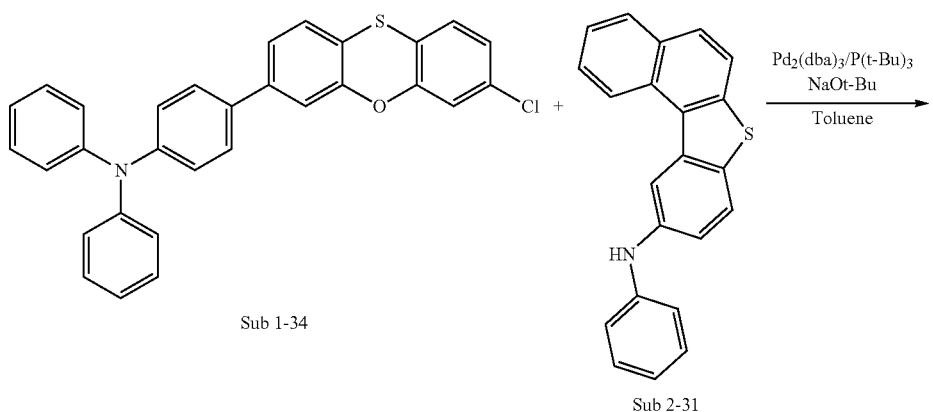

Sub 1-34            Sub 2-31

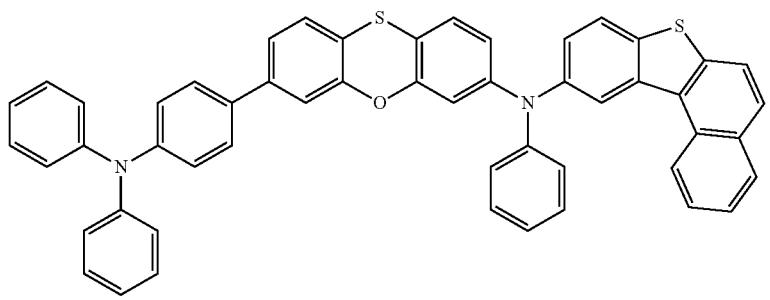

P-61

Sub 1-34 (5.70 g, 11.92 mmol) was dissolved in toluene (100 mL), and Sub 2-31 (3.88 g, 11.92 mmol), Pd$_2$(dba)$_3$ (0.33 g, 0.36 mmol), P(t-Bu)$_3$ (50 wt % Sol.) (0.48 mL, 1.19 mmol) and NaOt-Bu (3.44 g, 35.77 mmol) were added to the solution. Then, the reaction was carried out in the same manner as in the synthesis method of P-1 to obtain 5.58 g (yield: 61%) of the product P-61.

Synthesis Example of P-82

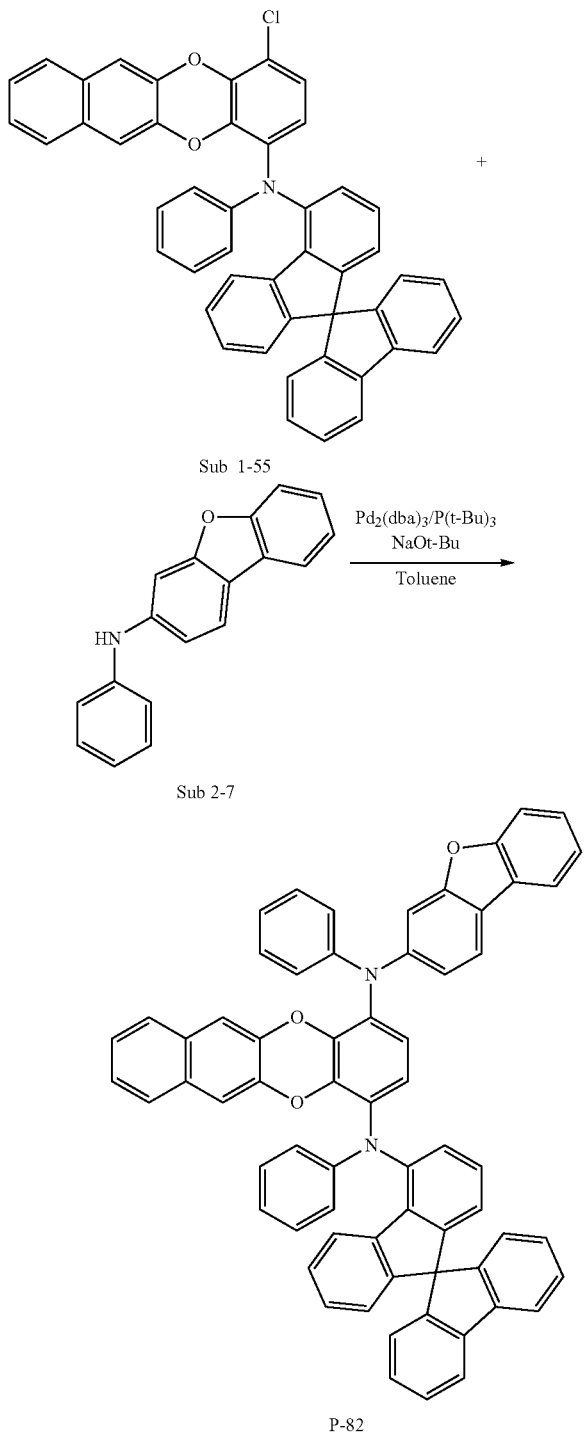

Sub 1-55 (8.25 g, 12.24 mmol) was dissolved in toluene (120 mL), and Sub 2-7 (3.17 g, 12.24 mmol), Pd$_2$(dba)$_3$ (0.34 g, 0.37 mmol), P(t-Bu)$_3$ (50 wt % Sol.) (0.50 mL, 1.22 mmol) and NaOt-Bu (3.53 g, 36.71 mmol) were added to the solution. Then, the reaction was carried out in the same manner as in the synthesis method of P-1 to obtain 8.34 g (yield: 76%) of the product P-82.

Synthesis Example of P-96

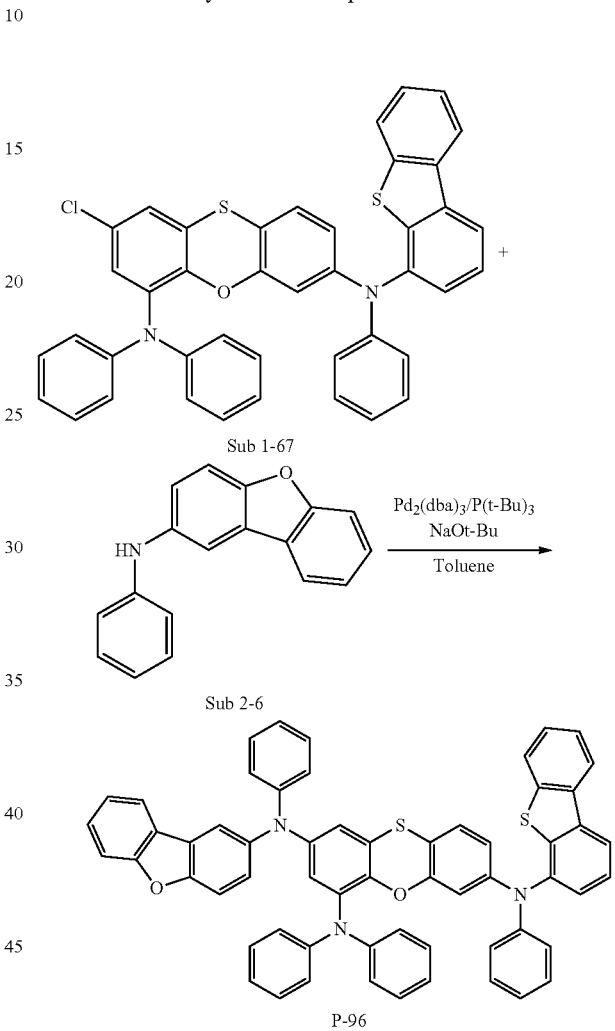

Sub 1-67 (7.63 g, 11.30 mmol) was dissolved in toluene (120 mL), and Sub 2-6 (2.93 g, 11.30 mmol), Pd$_2$(dba)$_3$ (0.31 g, 0.34 mmol), P(t-Bu)$_3$ (50 wt % Sol.) (0.46 mL, 1.13 mmol) and NaOt-Bu (3.26 g, 33.90 mmol) were added to the solution. Then, the reaction was carried out in the same manner as in the synthesis method of P-1 to obtain 8.02 g (yield: 79%) of the product P-96.

The FD-MS values of compounds 1-1 to 1-104 of the present invention synthesized by the same method as in Synthesis Example are shown in Table 3 below.

TABLE 3

| Compound | FD-MS |
| --- | --- |
| P-1 | m/z = 640.16 (C$_{42}$H$_{28}$N$_2$OS$_2$ = 640.82) |
| P-2 | m/z = 640.16 (C$_{42}$H$_{28}$N$_2$OS$_2$ = 640.82) |
| P-3 | m/z = 640.16 (C$_{42}$H$_{28}$N$_2$OS$_2$ = 640.82) |

TABLE 3-continued

| Compound | FD-MS |
|---|---|
| P-4 | m/z = 640.16 ($C_{42}H_{28}N_2OS_2$ = 640.82) |
| P-5 | m/z = 624.19 ($C_{42}H_{28}N_2O_2S$ = 624.76) |
| P-6 | m/z = 624.19 ($C_{42}H_{28}N_2O_2S$ = 624.76) |
| P-7 | m/z = 724.22 ($C_{50}H_{32}N_2O_2S$ = 724.88) |
| P-8 | m/z = 674.20 ($C_{46}H_{30}N_2O_2S$ = 674.82) |
| P-9 | m/z = 690.18 ($C_{48}H_{38}N_2OS_2$ = 690.88) |
| P-10 | m/z = 690.18 ($C_{46}H_{30}N_2O_2S_2$ = 690.88) |
| P-11 | m/z = 774.27 ($C_{55}H_{38}N_2OS$ = 774.98) |
| P-12 | m/z = 699.23 ($C_{48}H_{33}N_3OS$ = 699.87) |
| P-13 | m/z = 640.16 ($C_{42}H_{28}N_2OS_2$ = 640.82) |
| P-14 | m/z = 640.16 ($C_{42}H_{28}N_2OS_2$ = 640.82) |
| P-15 | m/z = 640.16 ($C_{42}H_{28}N_2OS_2$ = 640.82) |
| P-16 | m/z = 756.23 ($C_{51}H_{36}N_2OS_2$ = 756.98) |
| P-17 | m/z = 699.23 ($C_{48}H_{33}N_3OS$ = 699.87) |
| P-18 | m/z = 772.25 ($C_{55}H_{36}N_2OS$ = 772.97) |
| P-19 | m/z = 650.24 ($C_{45}H_{34}N_3OS$ = 650.84) |
| P-20 | m/z = 624.19 ($C_{42}H_{28}N_2O_2S$ = 624.76) |
| P-21 | m/z = 624.19 ($C_{42}H_{28}N_2O_2S$ = 624.76) |
| P-22 | m/z = 640.16 ($C_{42}H_{28}N_2OS_2$ = 640.82) |
| P-23 | m/z = 624.19 ($C_{42}H_{28}N_2O_2S$ = 624.76) |
| P-24 | m/z = 624.19 ($C_{42}H_{28}N_2O_2S$ = 624.76) |
| P-25 | m/z = 656.14 ($C_{42}H_{28}N_2S_3$ = 656.88) |
| P-26 | m/z = 656.14 ($C_{42}H_{28}N_2S_3$ = 656.88) |
| P-27 | m/z = 656.14 ($C_{42}H_{28}N_2S_3$ = 656.88) |
| P-28 | m/z = 821.20 ($C_{54}H_{35}N_3S_3$ = 822.08) |
| P-29 | m/z = 608.21 ($C_{42}H_{28}N_2O_3$ = 608.70) |
| P-30 | m/z = 608.21 ($C_{42}H_{28}N_2O_3$ = 608.70) |
| P-31 | m/z = 848.30 ($C_{61}H_{40}N_2O_3$ = 849.00) |
| P-32 | m/z = 608.21 ($C_{42}H_{28}N_2O_3$ = 608.70) |
| P-33 | m/z = 792.23 ($C_{54}H_{36}N_2OS_2$ = 793.02) |
| P-34 | m/z = 656.14 ($C_{42}H_{28}N_2S_3$ = 656.88) |
| P-35 | m/z = 608.21 ($C_{42}H_{28}N_2O_3$ = 608.70) |
| P-36 | m/z = 624.19 ($C_{42}H_{28}N_2O_2S$ = 624.76) |
| P-37 | m/z = 656.14 ($C_{42}H_{28}N_2S_3$ = 656.88) |
| P-38 | m/z = 656.14 ($C_{42}H_{28}N_2S_3$ = 656.88) |
| P-39 | m/z = 640.16 ($C_{42}H_{28}N_2OS_2$ = 640.82) |
| P-40 | m/z = 640.16 ($C_{42}H_{28}N_2OS_2$ = 640.82) |
| P-41 | m/z = 608.21 ($C_{42}H_{28}N_2O_3$ = 608.70) |
| P-42 | m/z = 608.21 ($C_{42}H_{28}N_2O_3$ = 608.70) |
| P-43 | m/z = 654.20 ($C_{43}H_{30}N_2O_3S$ = 654.78) |
| P-44 | m/z = 624.19 ($C_{42}H_{28}N_2O_2S$ = 624.76) |
| P-45 | m/z = 656.14 ($C_{42}H_{28}N_2S_3$ = 656.88) |
| P-46 | m/z = 656.14 ($C_{42}H_{28}N_2S_3$ = 656.88) |
| P-47 | m/z = 608.21 ($C_{42}H_{28}N_2O_3$ = 608.70) |
| P-48 | m/z = 624.19 ($C_{42}H_{28}N_2O_2S$ = 624.76) |
| P-49 | m/z = 788.23 ($C_{55}H_{36}N_2S_2$ = 789.03) |
| P-50 | m/z = 656.14 ($C_{42}H_{28}N_2S_3$ = 656.88) |
| P-51 | m/z = 640.16 ($C_{42}H_{28}N_2OS_2$ = 640.82) |
| P-52 | m/z = 624.19 ($C_{42}H_{28}N_2O_2S$ = 624.76) |
| P-53 | m/z = 772.20 ($C_{51}H_{36}N_2S_3$ = 773.04) |
| P-54 | m/z = 882.25 ($C_{59}H_{38}N_4OS_2$ = 883.10) |
| P-55 | m/z = 684.28 ($C_{49}H_{36}N_2O_2$ = 684.84) |
| P-56 | m/z = 733.27 ($C_{52}H_{35}N_3O_2$ = 733.87) |
| P-57 | m/z = 690.18 ($C_{46}H_{30}N_2OS_2$ = 690.88) |
| P-58 | m/z = 690.18 ($C_{46}H_{30}N_2OS_2$ = 690.88) |
| P-59 | m/z = 700.22 ($C_{48}H_{32}N_2O_2S$ = 700.86) |
| P-60 | m/z = 674.20 ($C_{46}H_{30}N_2O_2S$ = 674.82) |
| P-61 | m/z = 766.21 ($C_{52}H_{34}N_2OS_2$ = 766.98) |
| P-62 | m/z = 716.20 ($C_{48}H_{32}N_2OS_2$ = 716.92) |
| P-63 | m/z = 766.21 ($C_{52}H_{34}N_2OS_2$ = 766.98) |
| P-64 | m/z = 690.18 ($C_{45}H_{30}N_2OS_2$ = 690.88) |
| P-65 | m/z = 674.20 ($C_{45}H_{30}N_2O_2S$ = 674.82) |
| P-66 | m/z = 796.17 ($C_{52}H_{32}N_2OS_3$ = 797.02) |
| P-67 | m/z = 716.20 ($C_{49}H_{32}N_2OS_2$ = 716.92) |
| P-68 | m/z = 613.24 ($C_{42}H_{23}D_5N_2O_3$ = 613.73) |
| P-69 | m/z = 690.18 ($C_{46}H_{30}N_2OS_2$ = 690.88) |
| P-70 | m/z = 766.21 ($C_{52}H_{34}N_2OS_2$ = 766.98) |
| P-71 | m/z = 766.21 ($C_{52}H_{34}N_2OS_2$ = 766.98) |
| P-72 | m/z = 796.17 ($C_{52}H_{32}N_2OS_3$ = 797.02) |
| P-73 | m/z = 878.28 ($C_{62}H_{40}N_2O_2S$ = 877.07) |
| P-74 | m/z = 633.21 ($C_{43}H_{27}N_3O_3$ = 633.71) |
| P-75 | m/z = 752.22 ($C_{50}H_{32}N_4O_2S_2$ = 752.89) |
| P-76 | m/z = 871.21 ($C_{58}H_{37}N_3S_3$ = 872.14) |
| P-77 | m/z = 699.23 ($C_{48}H_{33}N_3OS$ = 699.87) |
| P-78 | m/z = 790.24 ($C_{53}H_{34}N_4OS$ = 790.94) |
| P-79 | m/z = 642.18 ($C_{42}H_{27}FN_2O_2S$ = 642.75) |
| P-80 | m/z = 830.21 ($C_{55}H_{34}N_2O_2S_2$ = 831.02) |
| P-81 | m/z = 698.22 ($C_{48}H_{30}N_2O_4$ = 698.78) |
| P-82 | m/z = 896.30 ($C_{55}H_{40}N_2O_3$ = 897.05) |
| P-83 | m/z = 1022.28 ($C_{71}H_{46}N_2S_3$ = 1023.34) |
| P-84 | m/z = 716.20 ($C_{48}H_{32}N_2OS_2$ = 716.92) |
| P-85 | m/z = 796.17 ($C_{52}H_{32}N_2OS_3$ = 797.02) |
| P-86 | m/z = 749.25 ($C_{52}H_{35}N_3OS$ = 749.93) |
| P-87 | m/z = 944.29 ($C_{63}H_{40}N_6O_2S$ = 945.11) |
| P-88 | m/z = 789.24 ($C_{54}H_{35}N_3O_2S$ = 789.95) |
| P-89 | m/z = 806.24 ($C_{55}H_{38}N_2O_2S$ = 807.04) |
| P-90 | m/z = 716.20 ($C_{48}H_{32}N_2OS_2$ = 716.92) |
| P-91 | m/z = 641.16 ($C_{41}H_{27}N_3OS_2$ = 641.81) |
| P-92 | m/z = 840.28 ($C_{59}H_{40}N_2O_2S$ = 841.04) |
| P-93 | m/z = 822.18 ($C_{54}H_{34}N_2OS_3$ = 423.06) |
| P-94 | m/z = 823.21 ($C_{54}H_{37}N_3S_3$ = 824.09) |
| P-95 | m/z = 956.32 ($C_{65}H_{44}N_4O_2S$ = 957.16) |
| P-96 | m/z = 897.25 ($C_{50}H_{39}N_3O_32$ = 898.11) |
| P-97 | m/z = 776.12 ($C_{48}H_3N_2OS_4$ = 779.02) |
| P-98 | m/z = 853.17 ($C_{54}H_{35}N_3S_4$ = 854.14) |
| P-99 | m/z = 784.27 ($C_{56}H_{36}N_2O_3$ = 784.92) |
| P-100 | m/z = 775.28 ($C_{54}H_{37}N_3O_3$ = 775.91) |
| P-101 | m/z = 780.19 ($C_{52}H_{32}N_2O_2S_2$ = 780.96) |
| P-102 | m/z = 819.26 ($C_{55}H_{37}N_3O_3S$ = 819.98) |
| P-103 | m/z = 717.19 ($C_{47}H_{31}N_3OS_2$ = 717.91) |
| P-104 | m/z = 841.28 ($C_{58}H_{39}N_3O_2S$ = 842.03) |

Manufacturing and Evaluation of Organic Electric Element

[Example 1] Red Organic Electric Element (an Emission-Auxiliary Layer)

After vacuum-depositing 4,4',4"-tris[2-naphthyl(phenyl) amino]triphenylamine (hereinafter, abbreviated as 2-TNATA) on an ITO layer (anode) formed on a glass substrate to form a hole injection layer with a thickness of 60 nm, a hole transport layer with a thickness of 60 nm was formed by vacuum-depositing N,N'-bis(1-naphthalenyl)-N,N'-bis-phenyl-(1,1'-biphenyl)-4,4'-diamine (hereinafter, abbreviated as "NPB") on the hole injection layer.

Subsequently, an emission-auxiliary layer with a thickness of 20 nm was formed by vacuum-depositing the compound P-1 of the present invention on the hole transport layer and 4,4'-N,N'-dicarbazole-biphenyl (hereinafter, abbreviated as CBP) as a host material and bis-(1-phenylisoquinolyl)iridium(III)acetylacetonate (hereinafter, abbreviated as (piq)$_2$Ir(acac)) as a dopant material in a weight ratio of 95:5 were deposited on the emission-auxiliary layer to form a light emitting layer with a thickness of 30 nm.

Subsequently, (1,1'-biphenyl-4-olato)bis(2-methyl-8-quinolinolato)aluminum (hereinafter, abbreviated as BAlq) was vacuum-deposited to a thickness of 10 nm on the light emitting layer to form a hole blocking layer, and tris-(8-hydroxyquinoline)aluminum (hereinafter, abbreviated as "Alq$_3$") was vacuum-deposited to a thickness of 40 nm on the hole blocking layer to form a an electron transport layer.

Thereafter, LiF was deposited to a thickness of 0.2 nm to form an electron injection layer, and then Al was deposited to a thickness of 150 nm to form a cathode. In this way, an organic electric element was manufactured.

[Example 2] to [Example 19] Red Organic Electric Element (an Emission-Auxiliary Layer)

The organic electric elements were manufactured in the same manner as described in Example 1 except that the compounds of the present invention described in the following Table 5, instead of compound P-1 of the present invention, were used as material of an emission-auxiliary layer.

[Comparative Example 1] and [Comparative Example 2]

The organic electric elements were manufactured in the same manner as described in Example 1 except that Comparative Compound 1 or 2 were used as material of an emission-auxiliary layer.

<Comparative Compound 1>

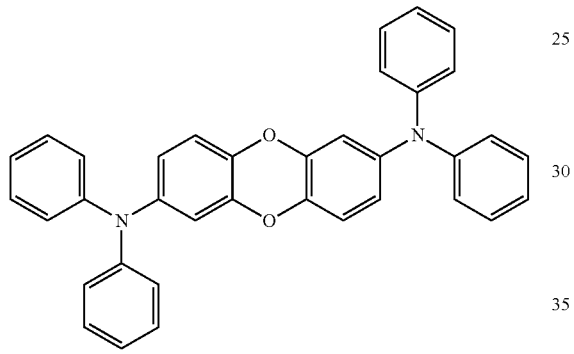

<Comparative Compound 2>

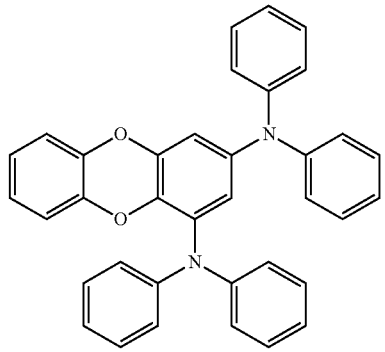

Electroluminescence characteristics were measured with a PR-650 from Photo research company by applying a forward bias DC voltage to the organic electric elements manufactured in Examples 1 to 19 of the present invention and Comparative Examples 1 and 2. T(95) life time was measured using a life time measuring apparatus manufactured by Mc science Inc. at reference brightness of 2500 cd/m². The measurement results are shown in the table 4 below.

TABLE 4

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| comp.Ex (1) | Comp. compd1 | 6.6 | 26.0 | 2500.0 | 9.6 | 110.3 | 0.63 | 0.30 |
| comp.Ex (2) | Comp. compd2 | 6.4 | 24.8 | 2500.0 | 10.1 | 109.7 | 0.63 | 0.32 |
| Ex.(1) | P-1 | 6.1 | 10.1 | 2500.0 | 22.8 | 165.7 | 0.63 | 0.30 |
| Ex.(2) | P-6 | 6.2 | 12.4 | 2500.0 | 22.3 | 167.1 | 0.64 | 0.33 |
| Ex.(3) | P-10 | 6.3 | 13.5 | 2500.0 | 21.9 | 159.8 | 0.62 | 0.33 |
| Ex.(4) | P-13 | 5.9 | 9.2 | 2500.0 | 27.6 | 153.2 | 0.64 | 0.31 |
| Ex.(5) | P-16 | 6.0 | 9.7 | 2500.0 | 25.7 | 146.4 | 0.65 | 0.34 |
| Ex.(6) | P-24 | 6.1 | 10.3 | 2500.0 | 23.5 | 140.8 | 0.64 | 0.31 |
| Ex.(7) | P-25 | 5.9 | 9.3 | 2500.0 | 22.6 | 164.9 | 0.61 | 0.33 |
| Ex.(8) | P-28 | 6.1 | 10.6 | 2500.0 | 21.7 | 160.1 | 0.60 | 0.32 |
| Ex.(9) | P-31 | 6.3 | 13.1 | 2500.0 | 18.9 | 161.7 | 0.64 | 0.34 |
| Ex.(10) | P-33 | 6.2 | 12.1 | 2500.0 | 20.8 | 158.4 | 0.64 | 0.34 |
| Ex.(11) | P-37 | 5.9 | 9.3 | 2500.0 | 26.3 | 143.7 | 0.63 | 0.32 |
| Ex.(12) | P-41 | 6.1 | 9.9 | 2500.0 | 24.6 | 148.6 | 0.60 | 0.35 |
| Ex.(13) | P-49 | 6.2 | 10.0 | 2500.0 | 20.5 | 157.8 | 0.61 | 0.34 |
| Ex.(14) | P-53 | 6.0 | 9.7 | 2500.0 | 25.1 | 145.1 | 0.62 | 0.33 |
| Ex.(15) | P-55 | 6.0 | 10.2 | 2500.0 | 24.0 | 142.0 | 0.60 | 0.32 |
| Ex.(16) | P-57 | 6.2 | 10.8 | 2500.0 | 21.4 | 159.5 | 0.63 | 0.34 |
| Ex.(17) | P-66 | 6.3 | 13.0 | 2500.0 | 19.9 | 155.3 | 0.61 | 0.32 |
| Ex.(18) | P-92 | 6.3 | 11.0 | 2500.0 | 23.1 | 138.9 | 0.63 | 0.33 |
| Ex.(19) | P-94 | 6.0 | 11.4 | 2500.0 | 21.1 | 158.9 | 0.60 | 0.34 |

From of Table 4, it can be seen that it is possible to not only lower the driving voltage of an organic electroluminescent element, but also significantly improve luminous efficiency and lifespan when a red organic electroluminescent element is manufactured using the material for an organic electroluminescent element of the present invention as a light emitting auxiliary layer material, compared to Comparative Examples using Comparative Compound 1 or Comparative Compound 2.

Comparing Comparative Compounds 1 and 2, the driving voltage and efficiency of the element were better when Comparative Compound 2, in which two amine groups are bonded to the same benzene ring of the dibenzodioxin core, is used as an auxiliary layer material, compared to Comparative Compound 1 in which amine groups are respectively bonded to both benzene rings of the dibenzodioxin core.

Comparing the compound of the present invention and the comparative compound, the basic skeleton of the core is similar to each other, but the compound of the present invention is different from the comparative compound in that a specific substituent such as dibenzothiophene, dibenzofuran, carbazole, or fluorene is necessarily substituted for the amine group. Due to these structural differences, when the compound of the present invention is used as a light emitting auxiliary layer material, the driving voltage, efficiency and lifespan are significantly improved compared to the comparative compound. This seems to be because the refractive index is significantly higher, Tg is also increased, and thermal stability is improved when three or more cyclic compounds such as dibenzothiophene and dibenzofuran are introduced as a substituent than when a general aryl group substituent is substituted.

In particular, the element result of the compound in which two amine groups are substituted on the same benzene ring among the comparative compounds shows more improved in terms of luminous efficiency. This result suggests that even if the core of compound is a similar, the characteristics such as hole characteristics, light efficiency characteristics, energy levels (LUMO, HOMO level, T1 level), hole injection, hole mobility and electron blocking ability vary depending on the bonding position of a substituent, and completely different element results can be derived due to differences in these characteristics.

Although the exemplary embodiments of the present invention have been described for illustrative purposes, those skilled in the art to which the present invention pertains will be capable of various modifications without departing from the essential characteristics of the present invention. Therefore, the embodiments disclosed in this specification are not intended to limit the present invention, but to illustrate the present invention, and the spirit and scope of the present invention are not limited by the embodiments. The scope of the present invention shall be construed on the basis of the accompanying claims, and it shall be construed that all of the technical ideas included within the scope equivalent to the claims belong to the present invention.

The invention claimed is:
1. A compound of Formula 1:

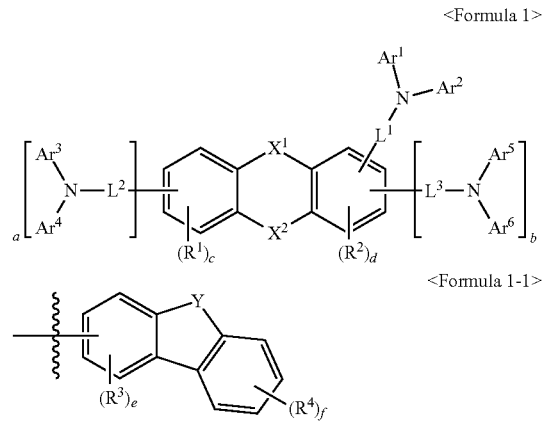

<Formula 1>

<Formula 1-1> wherein:
$X^1$ and $X^2$ are each independently O or S,
$Ar^1$ to $Ar^6$ are each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a $C_1$-$C_{60}$ alkyl group, a $C_2$-$C_{20}$ alkenyl group, a $C_2$-$C_{20}$ alkynyl group, a $C_1$-$C_{30}$ alkoxyl group and a $C_6$-$C_{30}$ aryloxy group, with the proviso that at least one of $Ar^1$ to $Ar^6$ is Formula 1-1,
$L^1$ to $L^3$ are each independently selected from the group consisting of a single bond, a $C_6$-$C_{60}$ arylene group, a fluorenylene group, a $C_3$-$C_{60}$ aliphatic ring, a $C_2$-$C_{60}$ heterocyclic group comprising at least one heteroatom selected from the group consisting of O, N, S, Si and P, and a combination thereof,
a and b are each an integer of 0 or 1, and at least one of a and b is 1,
$R^1$ and $R^2$ are each independently selected from the group consisting of hydrogen, deuterium, tritium, halogen, a cyano group, a nitro group, a $C_6$-$C_{60}$ aryl group, a fluorenyl group, a $C_2$-$C_{60}$ heterocyclic group comprising at least one heteroatom selected from the group consisting of O, N, S, Si and P, a fused ring of a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), and adjacent groups may be bonded to each other to form a ring,
c is an integer from 0 to 4, d is an integer from 0 to 3, and when each of these is an integer of 2 or more, each of a plurality of $R^1$ and each of a plurality of $R^2$ are the same as or different from each other,
in Formula 1-1,
Y is C(R')(R''), N(R'), O or S,
$R^3$ and $R^4$ are each independently selected from the group consisting of hydrogen, deuterium, tritium, halogen, a cyano group, a nitro group, a $C_6$-$C_{60}$ aryl group, a fluorenyl group, a $C_2$-$C_{60}$ heterocyclic group comprising at least one heteroatom selected from the group consisting of O, N, S, Si and P, a fused ring of a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), and adjacent groups may be bonded to each other to form a ring, e is an integer of 0-3, f is an integer of 0-4, and when each of these is an integer of 2 or more, each of a plurality of $R^3$ and each of a plurality of $R^4$ are the same as or different from each other, R' and R" are each independently selected from the group consisting of hydrogen, a $C_6$-$C_{60}$ aryl group, a fluorenyl group, a $C_3$-$C_{60}$ heterocyclic group, a $C_1$-$C_{50}$ alkyl group, a $C_2$-$C_{60}$ alkenyl group, and a $C_6$-$C_{60}$ aryloxy group, and R' and R" may be bonded to each other to form a ring, with the proviso that the alkyl group is excluded from R' and R" where a is 1 and Y is C(R')(R"), L' is selected from the group consisting of a single bond, a $C_6$-$C_{60}$ arylene group, a fluorenylene group, a $C_3$-$C_{60}$ aliphatic ring, a $C_2$-$C_{60}$ heterocyclic group comprising at least one heteroatom selected from the group consisting of O, N, S, Si and P, and a combination thereof, $R_a$ and $R_b$ are each independently selected from the group consisting of a $C_6$-$C_{60}$ aryl group, a fluorenyl group, a $C_3$-$C_{60}$ aliphatic ring, and a $C_2$-$C_{60}$ heterocyclic group comprising at least one heteroatom selected from the group consisting of O, N, S, Si and P, and the aryl group, arylene group, fluorenyl group, fluorenylene group, heterocyclic group, aliphatic ring group, fused ring group, alkyl group, alkenyl group, alkynyl group, alkoxyl group, or aryloxyl group of $Ar^1$ to $Ar^6$, $L^1$ to $L^3$, $R^1$ to $R^4$, R', R", L', $R_a$, $R_b$, or the ring formed by adjacent groups of $R^1$ to $R^4$ or formed by R' and R" may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ aliphatic ring group, a $C_7$-$C_{20}$ arylalkyl group and $C_8$-$C_{20}$ arylalkenyl group.

2. The compound of claim 1, wherein Formula 1 is represented by one of Formula 2 to Formula 4:

<Formula 2>

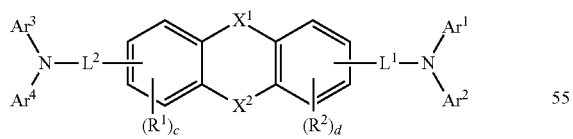

<Formula 3>

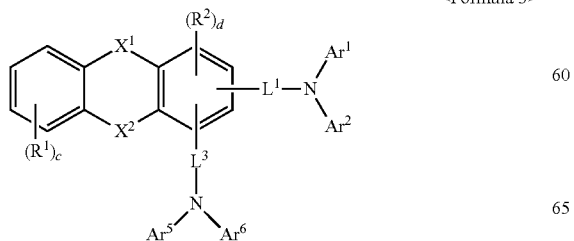

<Formula 4>

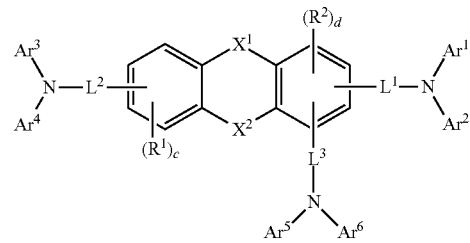

wherein $X^1$, $X^2$, $R^1$, $R^2$, $L^1$ to $L^3$, $Ar^1$ to $Ar^6$, c and d are the same as defined in claim 1.

3. The compound of claim 1, wherein Formula 1 is represented by one of Formula 5 to Formula 13:

<Formula 5>

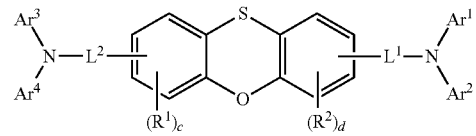

<Formula 6>

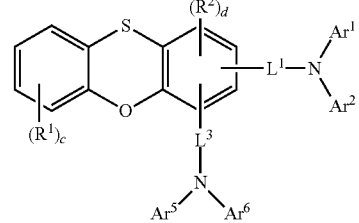

<Formula 7>

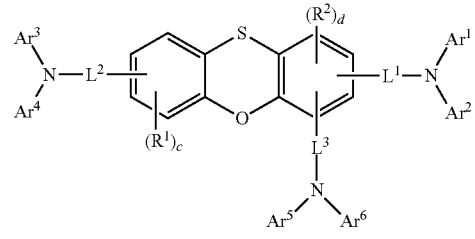

<Formula 8>

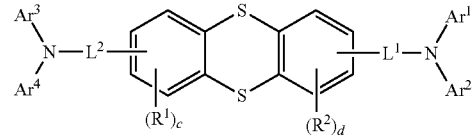

<Formula 9>

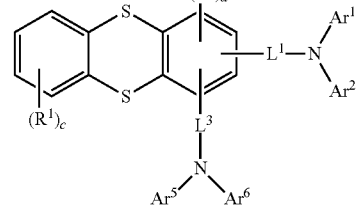

<Formula 10>
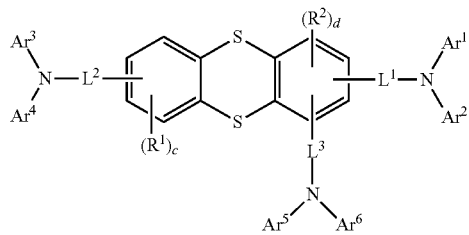
<Formula 11>
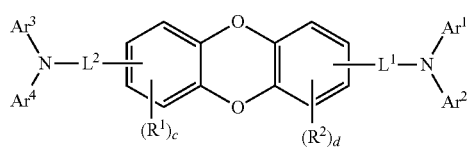
<Formula 12>
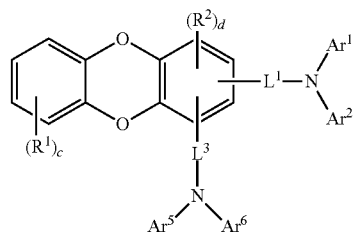
<Formula 13>
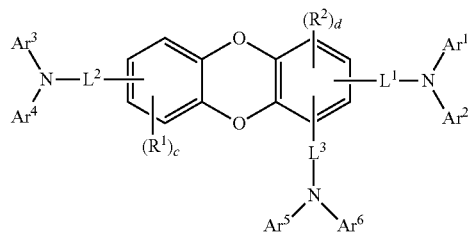
wherein $R^1$, $R^2$, $L^1$ to $L^3$, $Ar^1$ to $Ar^6$, c and d are the same as defined in claim 1.
4. The compound of claim 1, wherein the compound represented by Formula 1 is one of the following compounds:
P-1
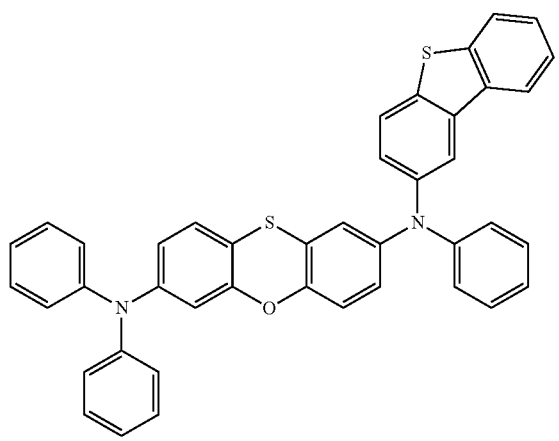
P-2
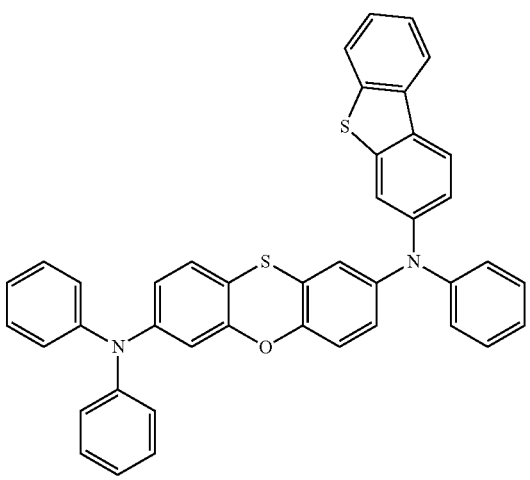
P-3
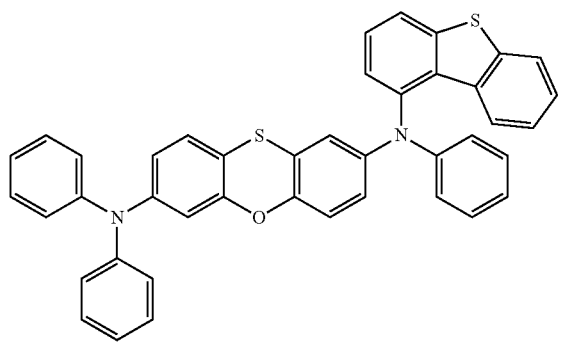
P-4
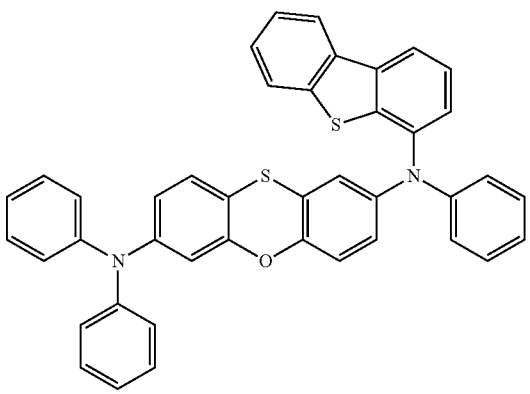

-continued
P-5
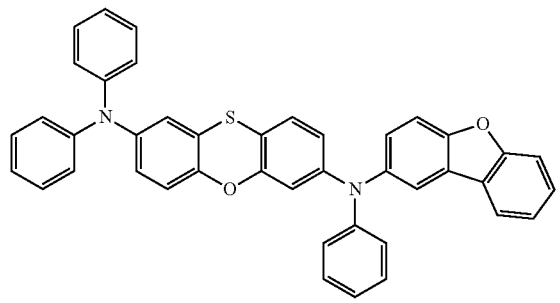
P-6
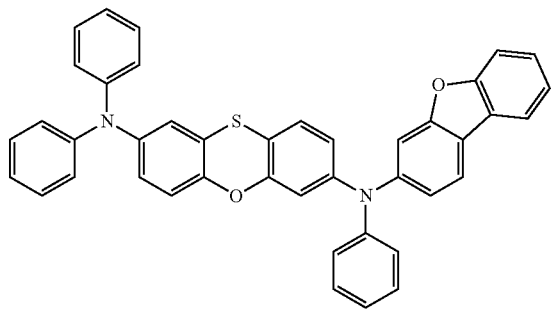
P-7
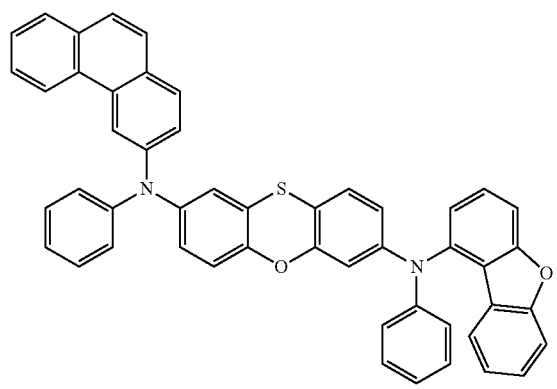
P-8
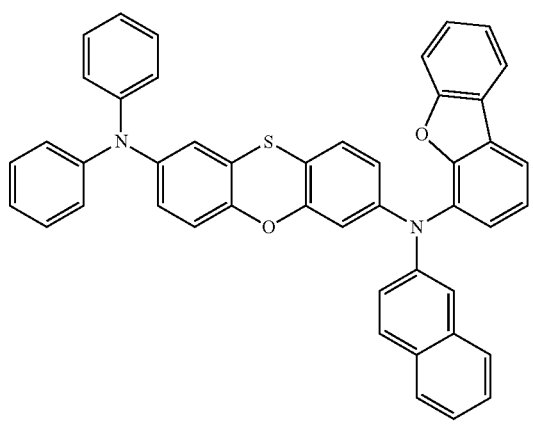
P-9
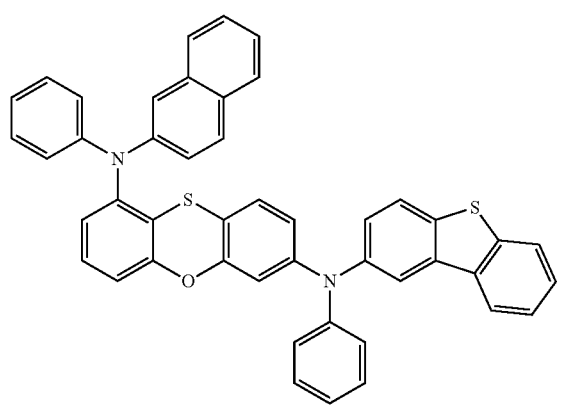
P-10
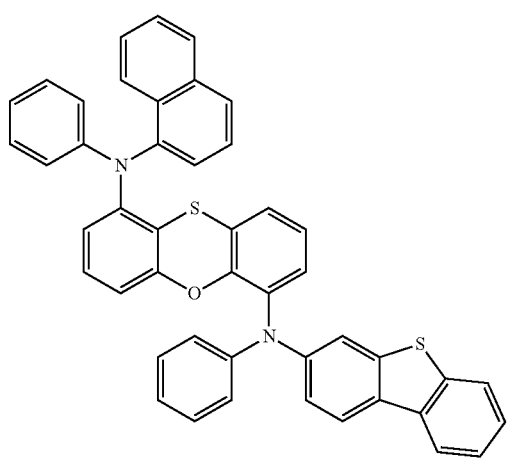

-continued
P-11
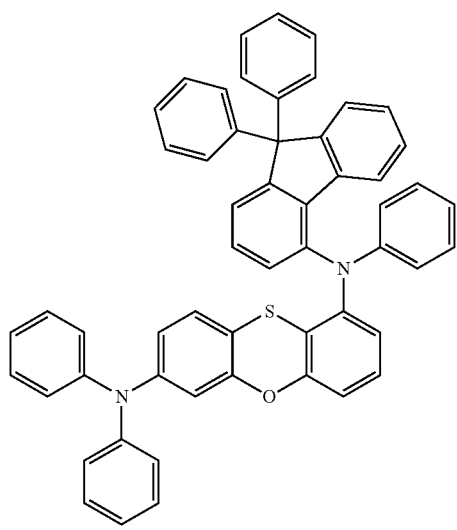
P-12
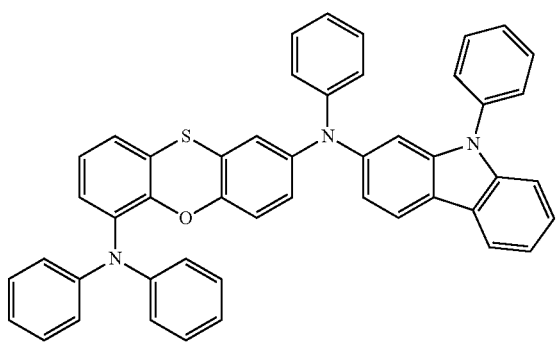
P-13
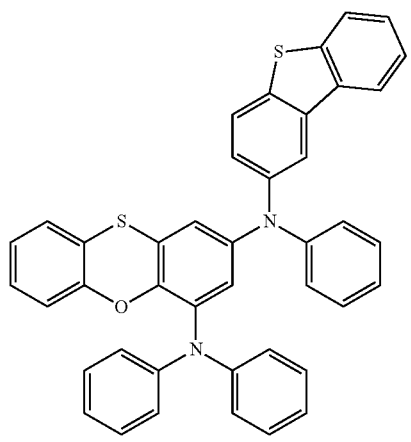
P-14
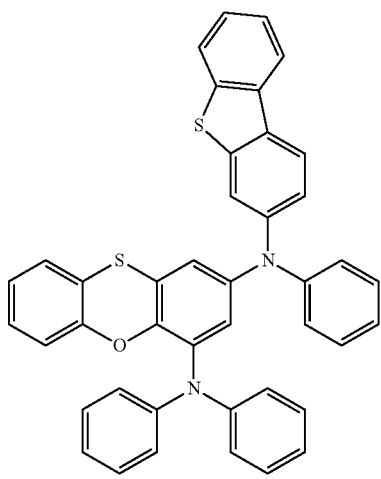
P-15
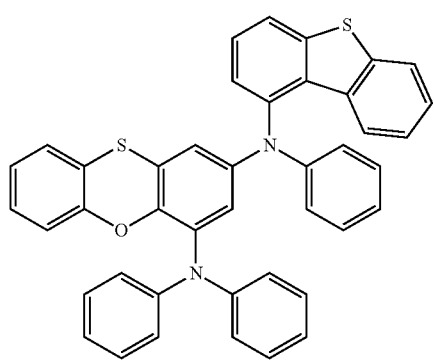
P-16
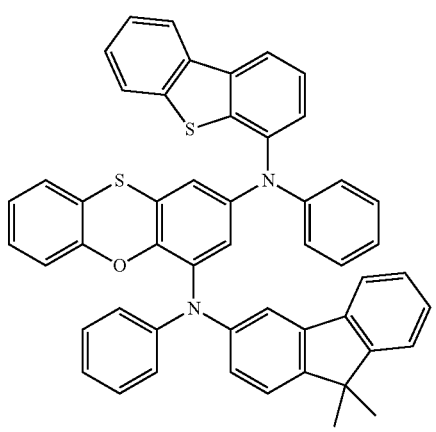

-continued
P-17
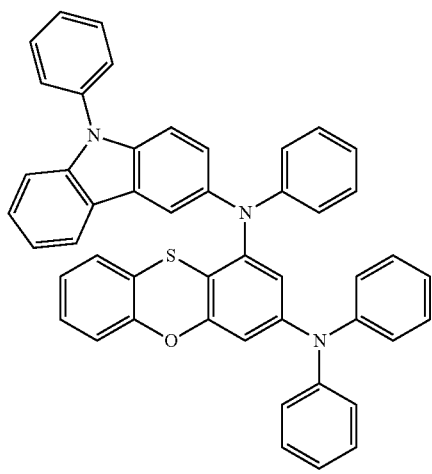
P-18
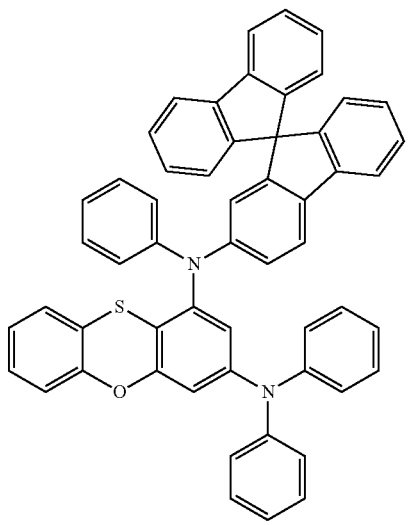
P-19
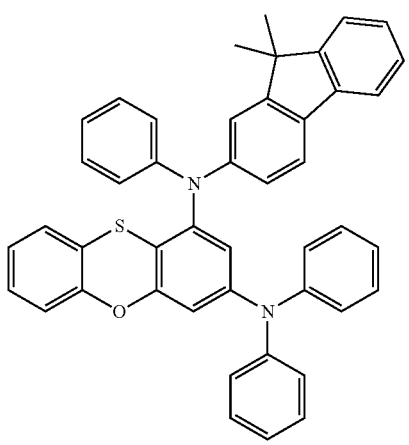
P-20
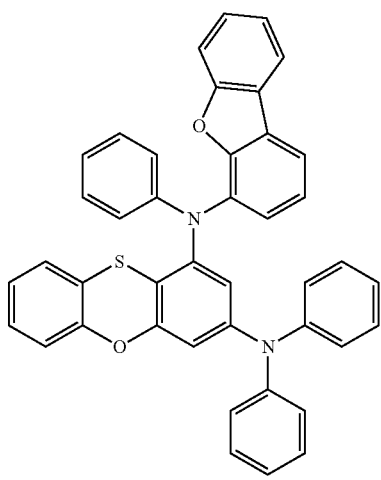
P-21
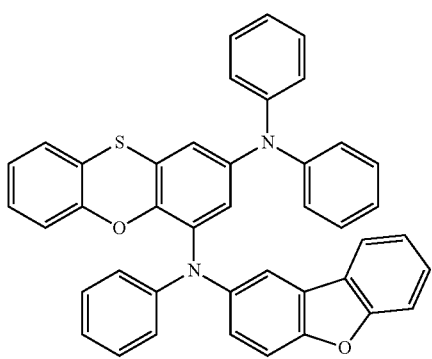
P-22
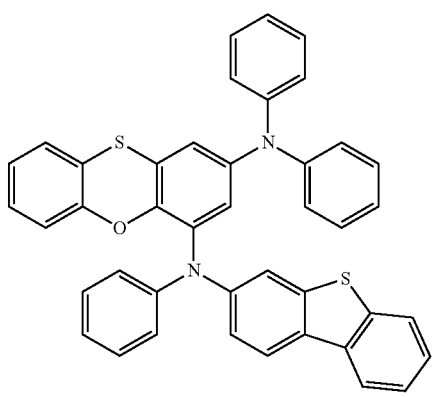

-continued
P-23
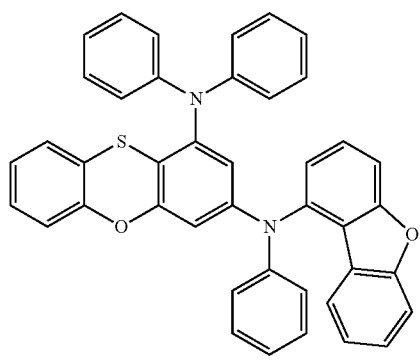
P-24
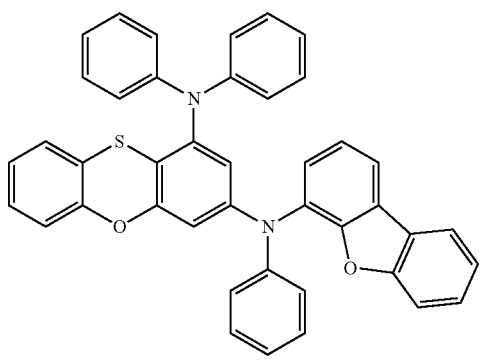
P-25
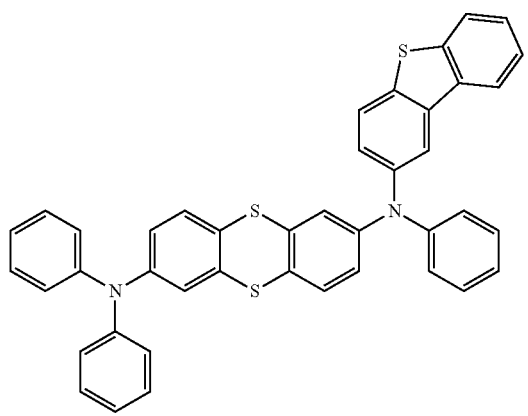
P-26
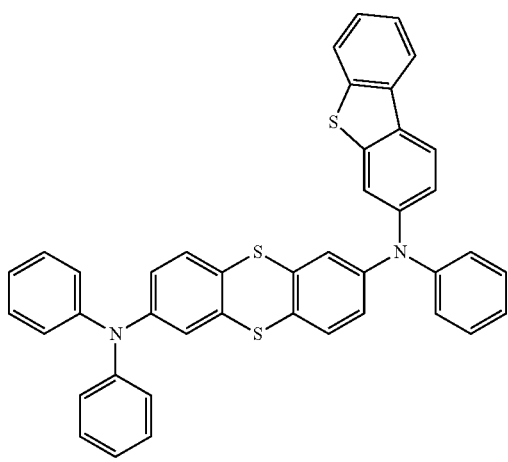
P-27
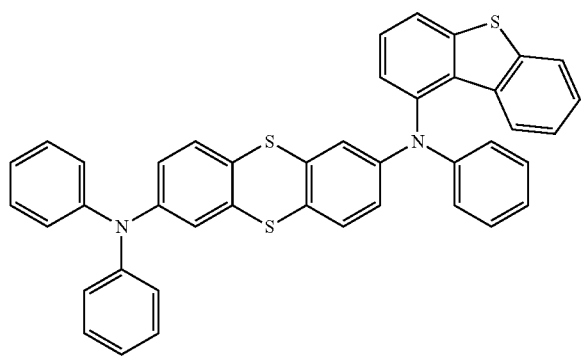
P-28
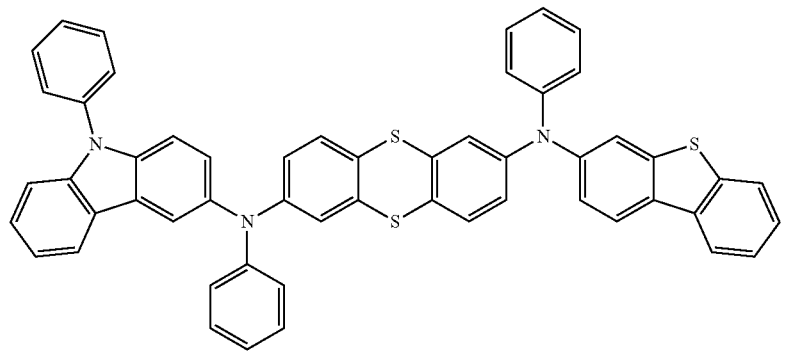

-continued
P-29
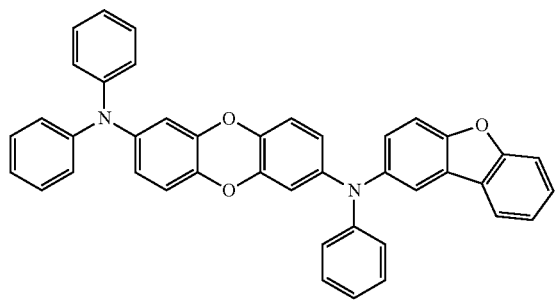
P-30
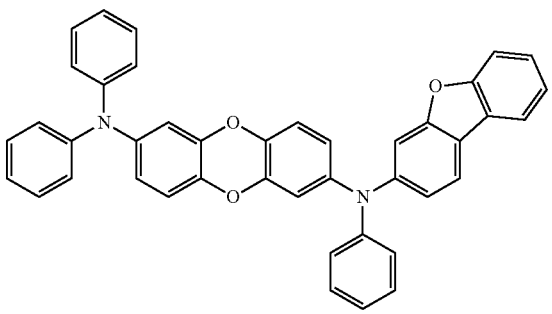
P-31
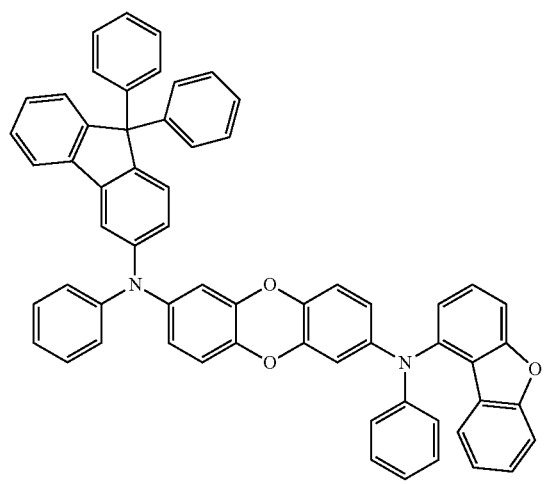
P-32
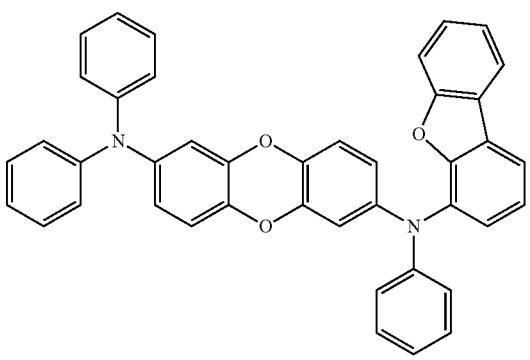
P-33
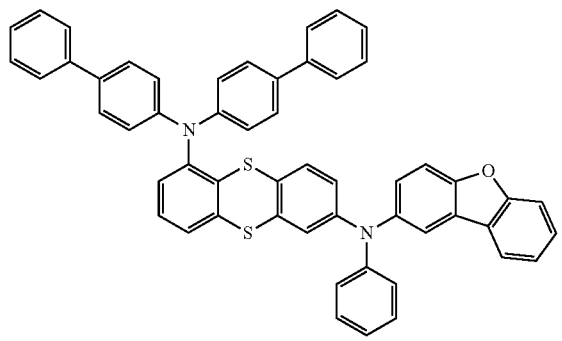
P-34
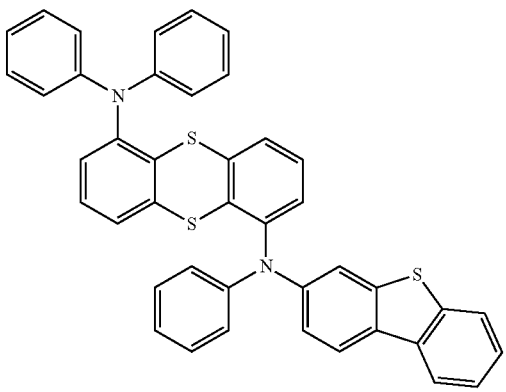

-continued
P-35
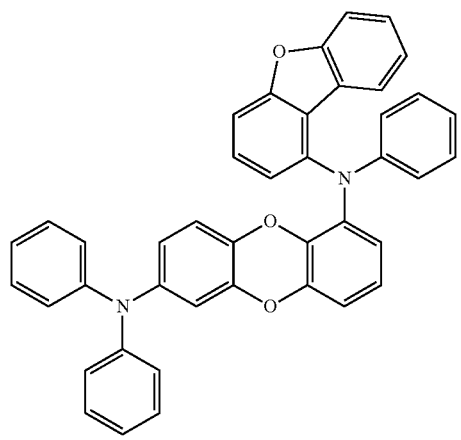
P-36
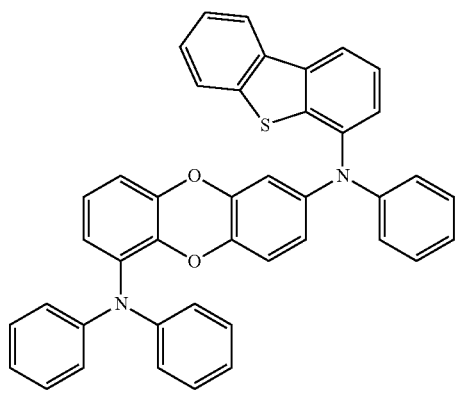
P-37
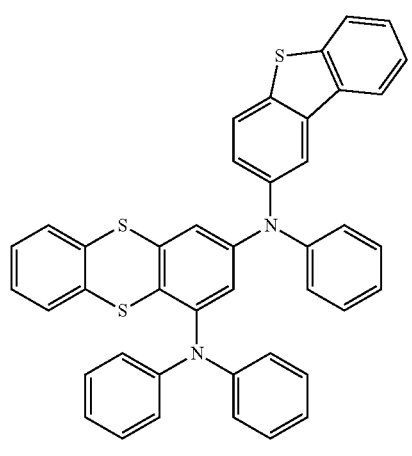
P-38
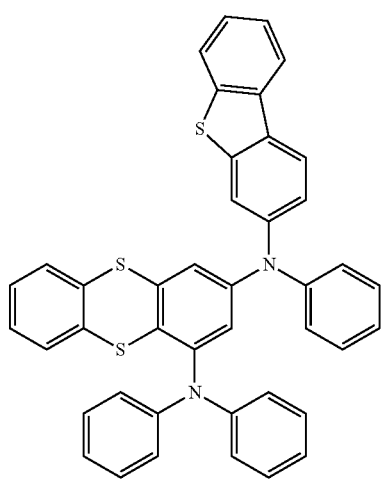
P-39
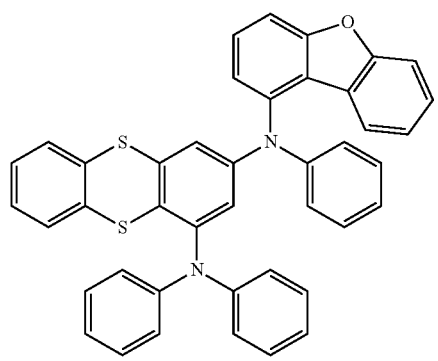
P-40
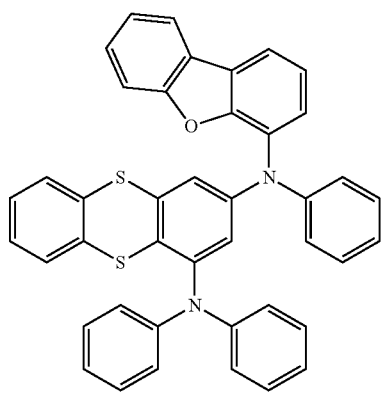

-continued
P-41
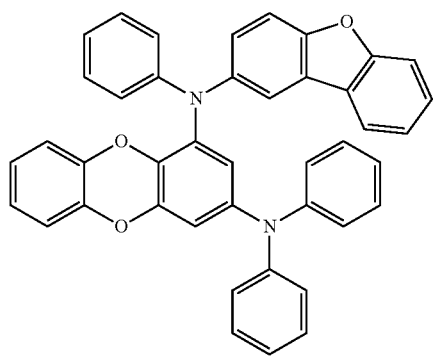
P-42
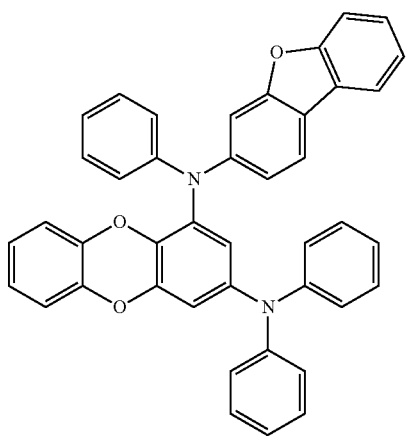
P-43
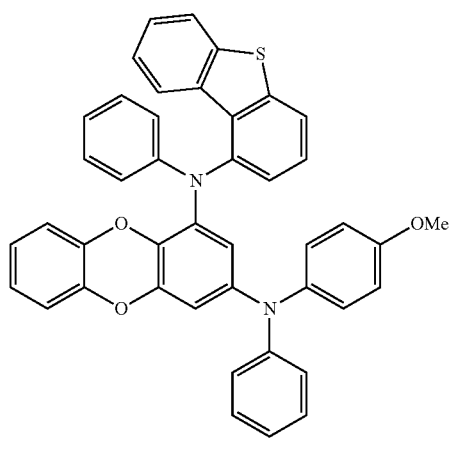
P-44
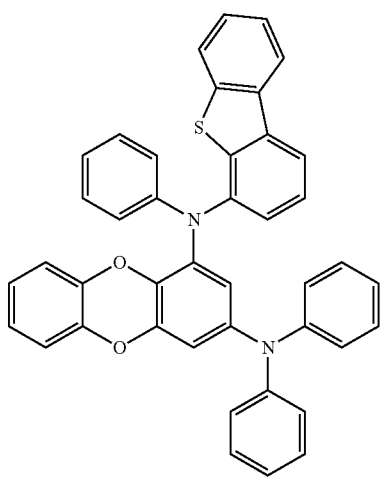
P-45
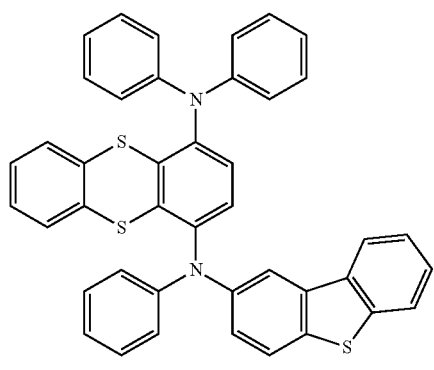
P-46
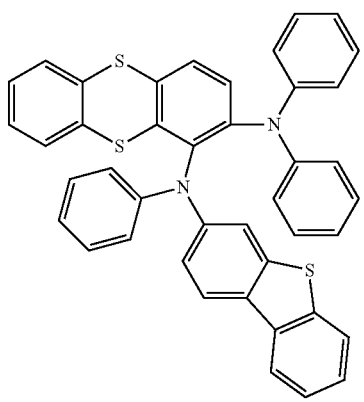

-continued
P-47
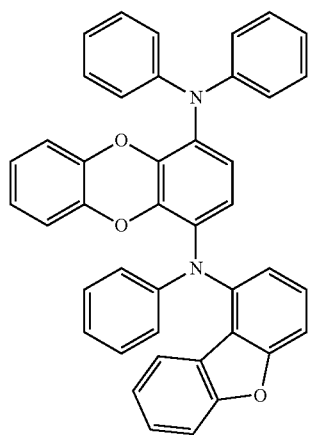
P-48
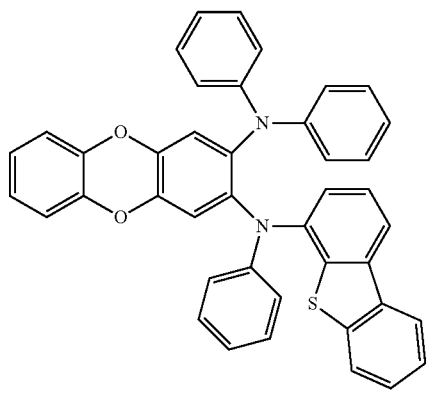
P-49
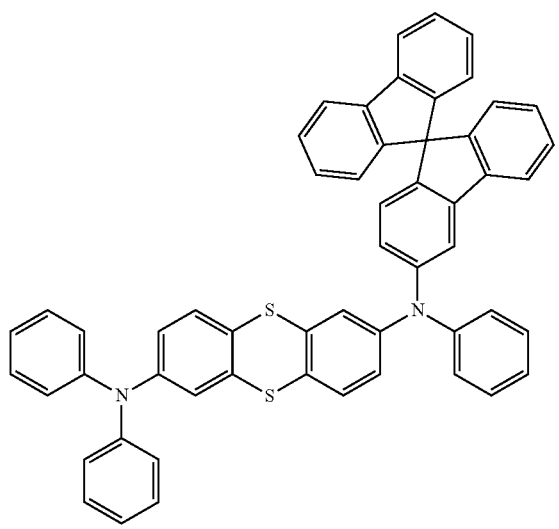
P-50
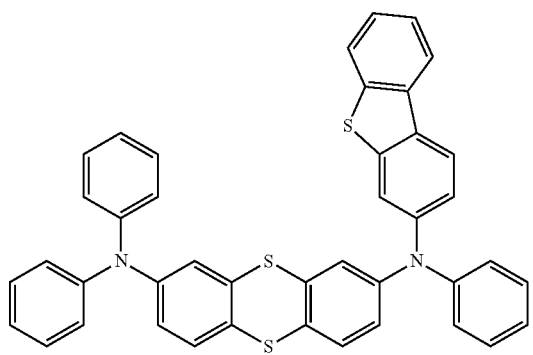
P-51
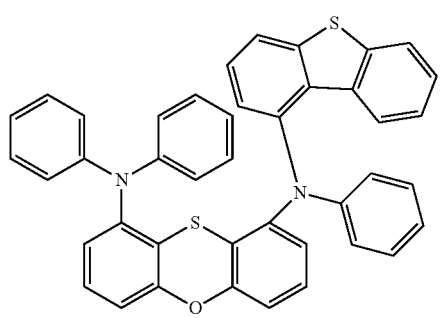
P-52
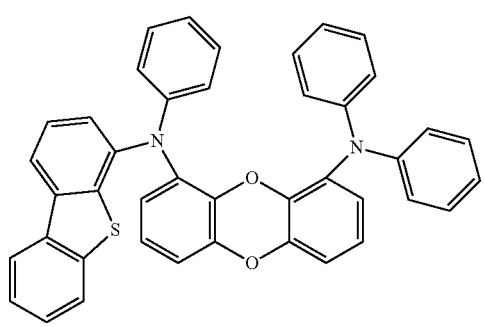

-continued
P-53
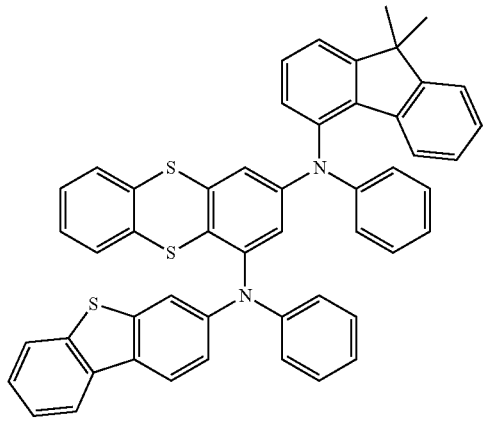
P-54
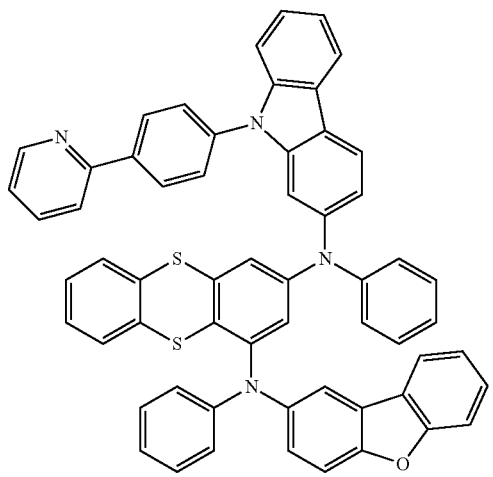
P-55
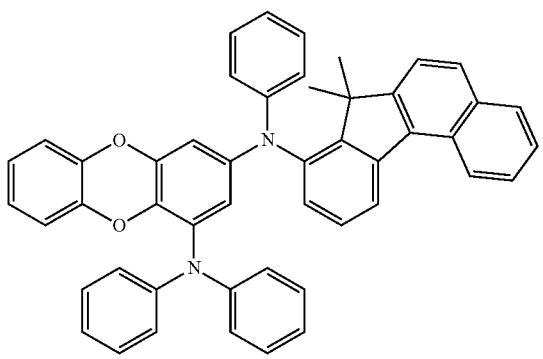
P-56
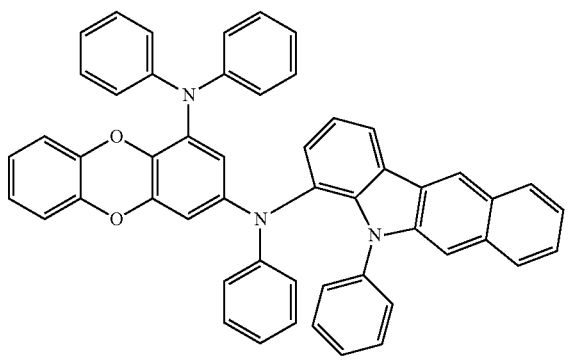
P-57
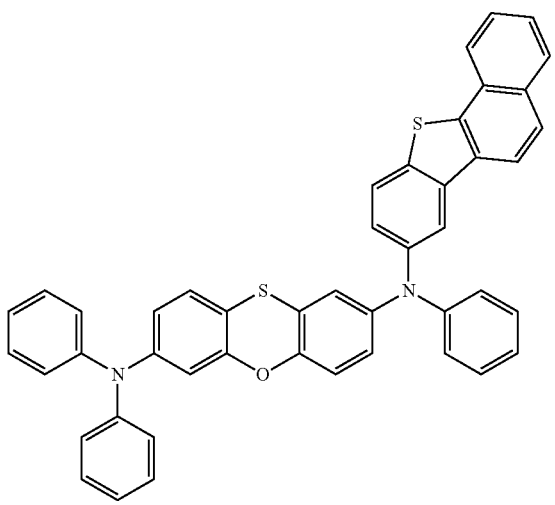
P-58
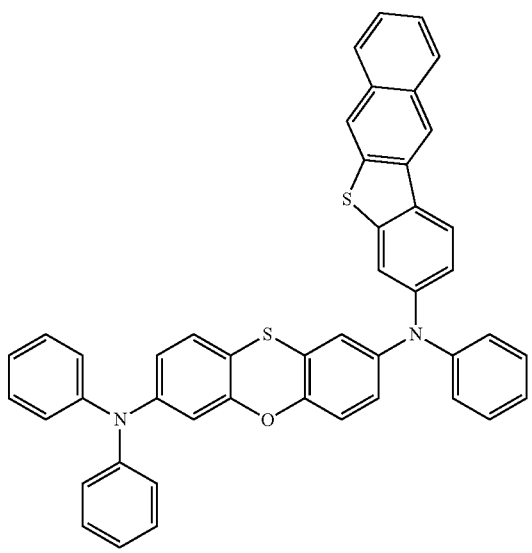

-continued
P-59
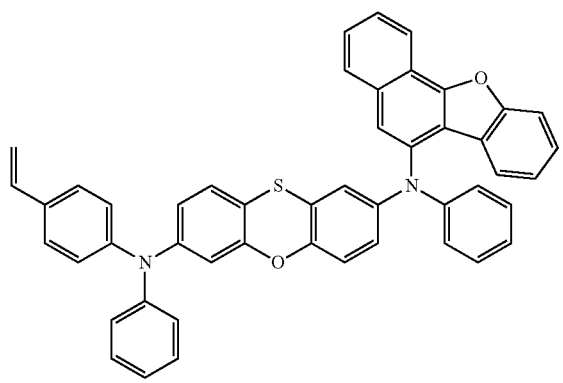
P-60
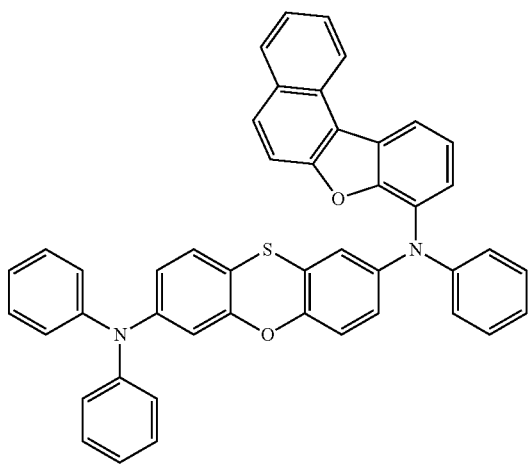
P-61
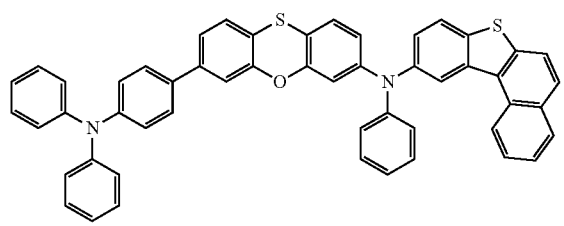
P-62
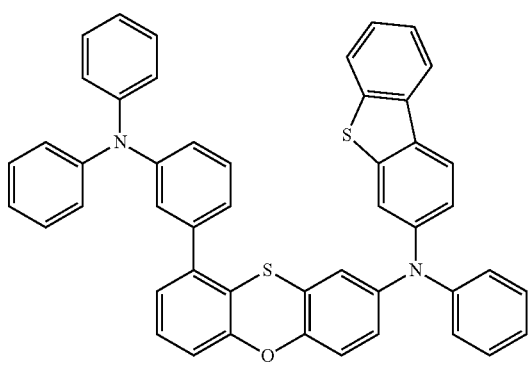
P-63
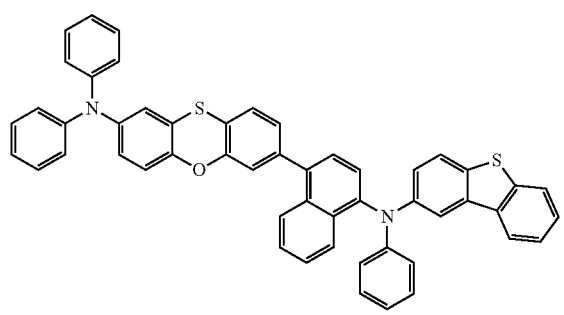
P-64
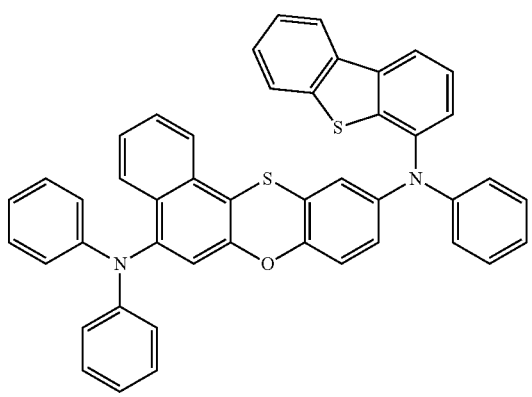

-continued
P-65
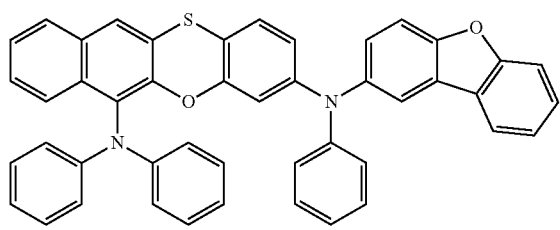
P-66
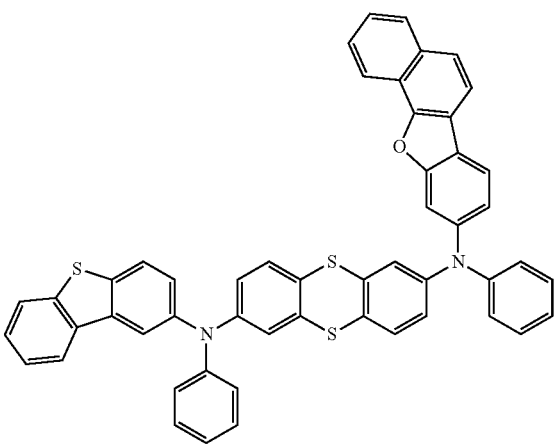
P-67
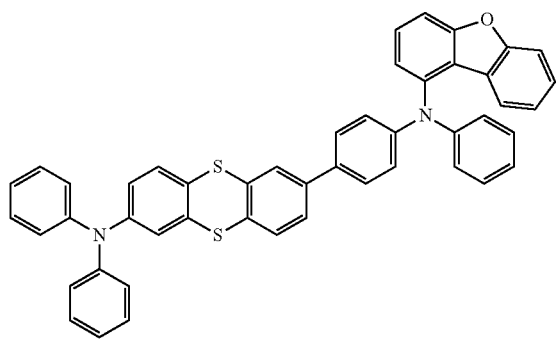
P-68
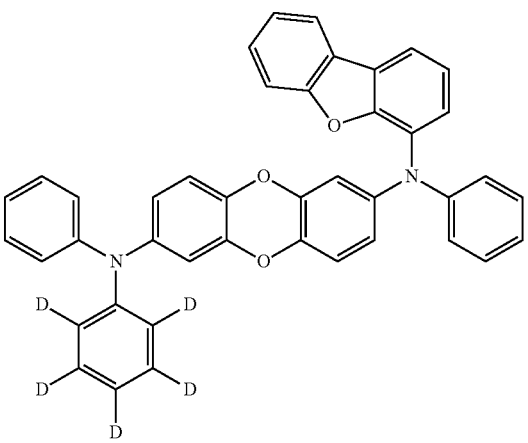
P-69
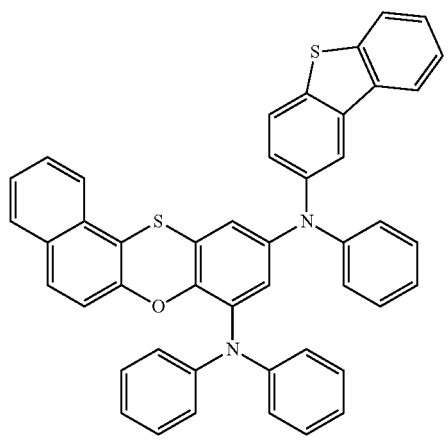
P-70
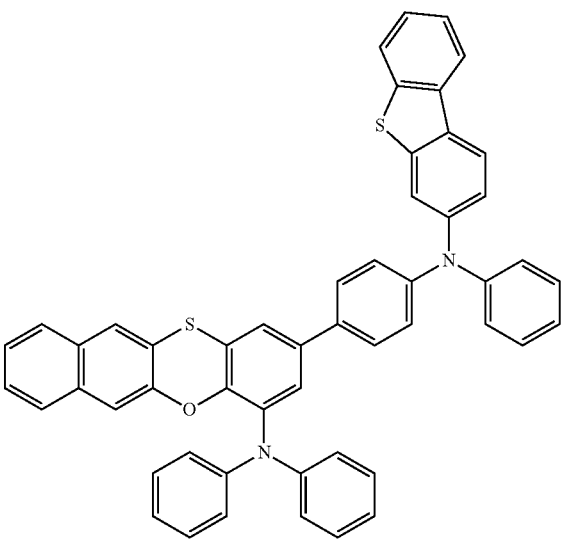

-continued
P-71
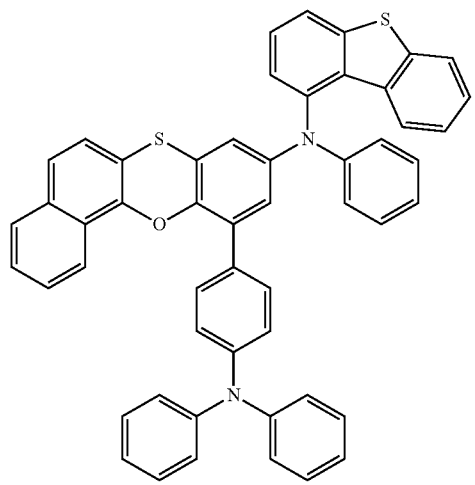
P-72
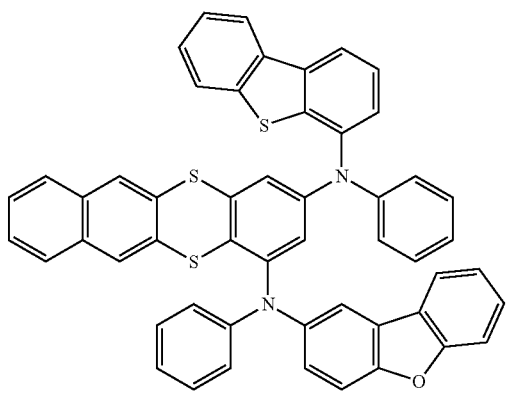
P-73
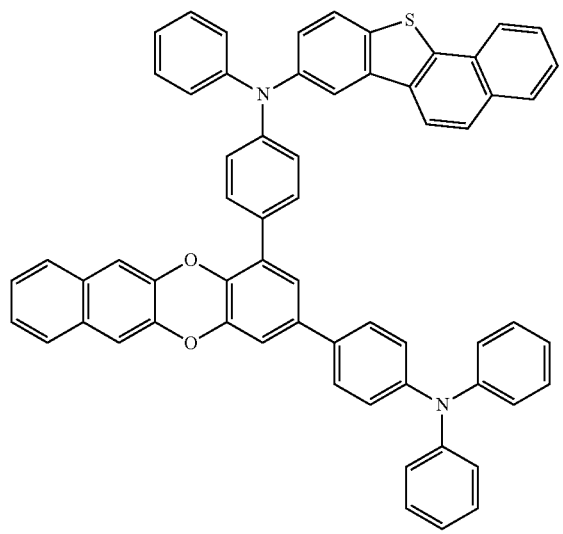
P-74
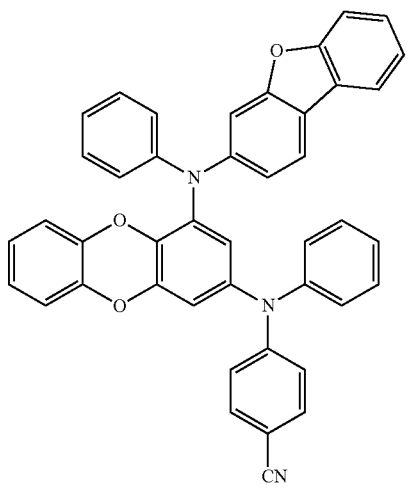
P-75
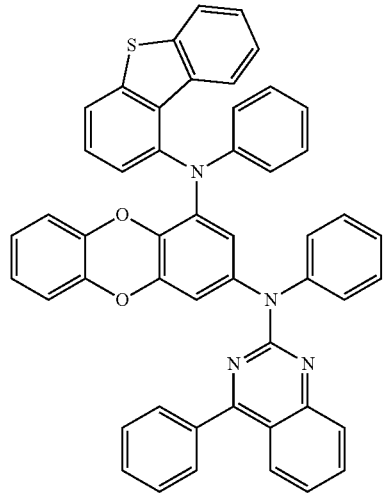
P-76
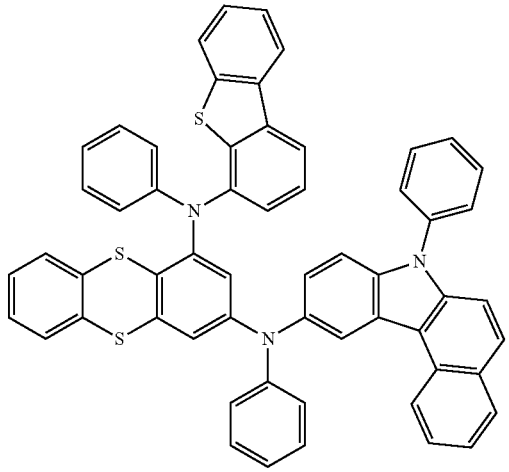

P-77
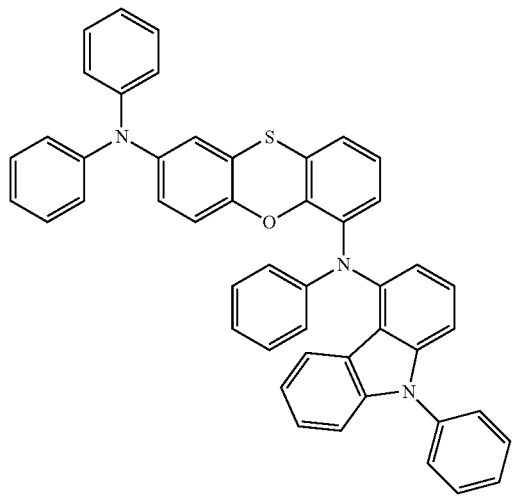
P-78
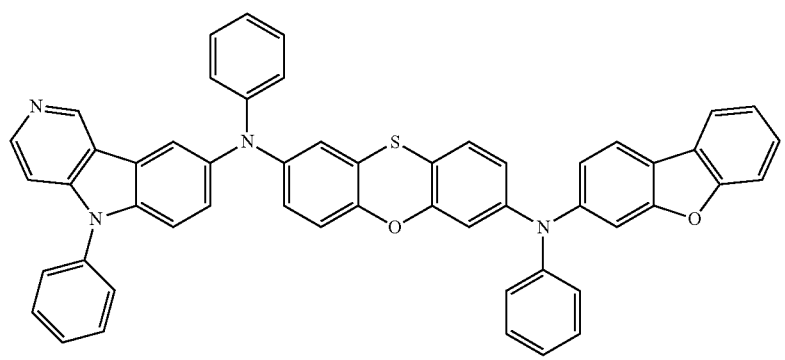
P-79
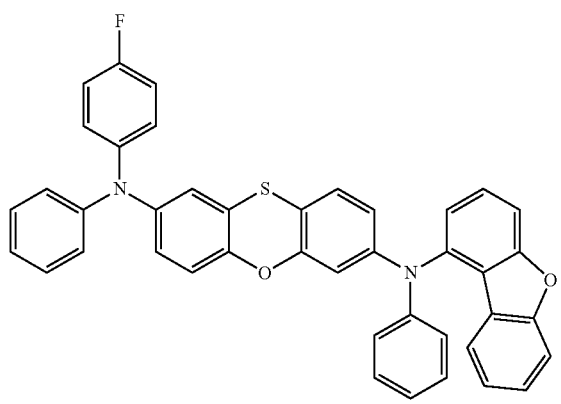
P-80
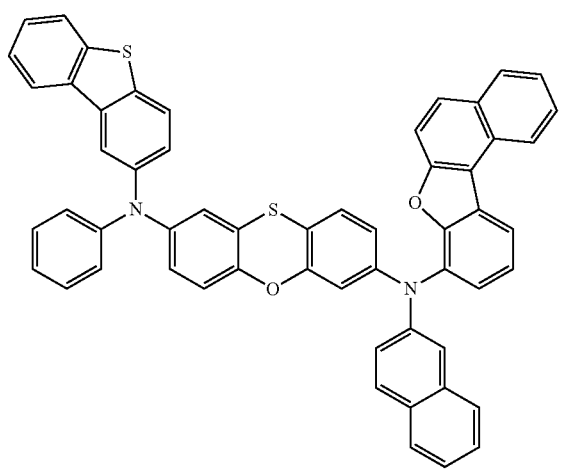

-continued
P-81
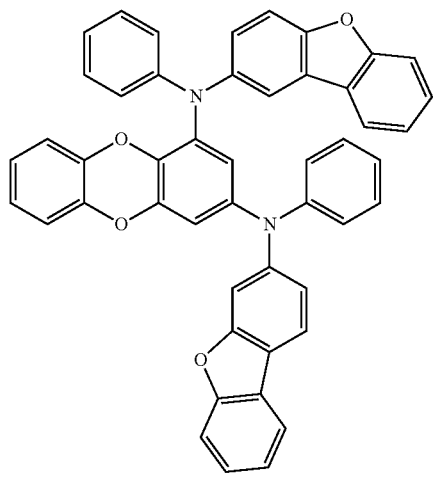
P-82
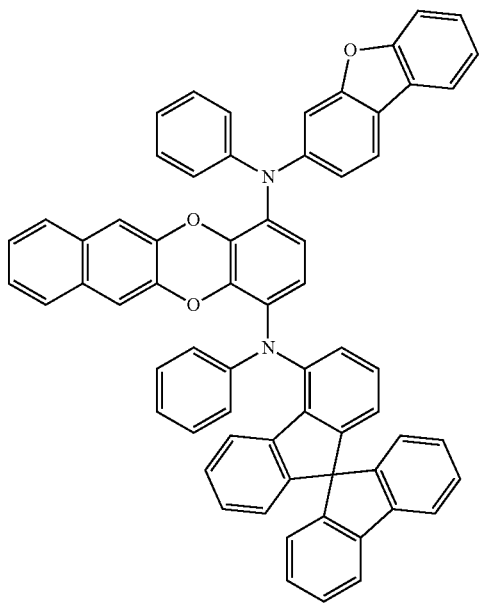
P-83
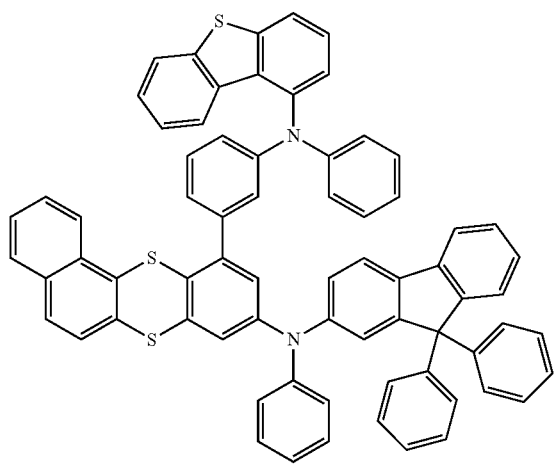
P-84
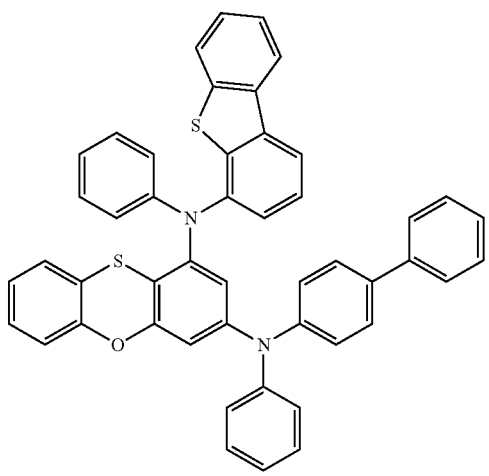
P-85
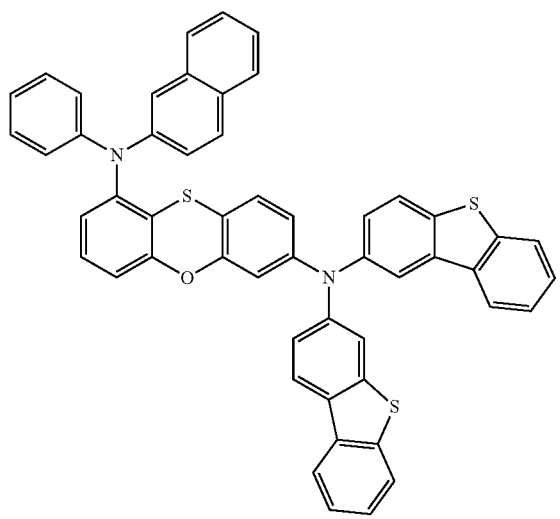
P-86
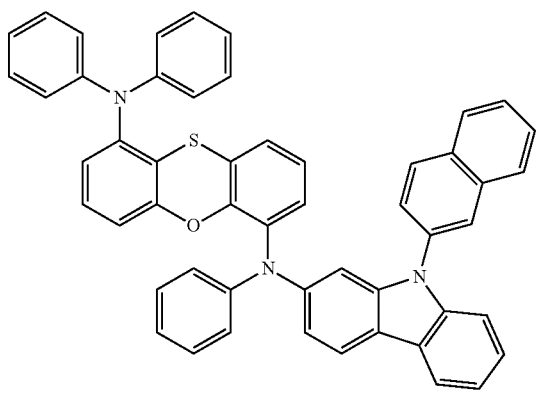

-continued
P-87
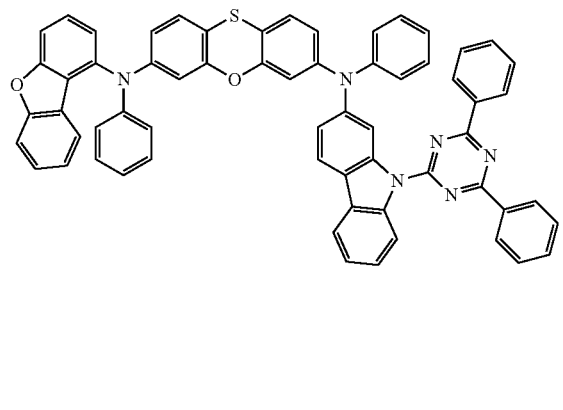
P-88
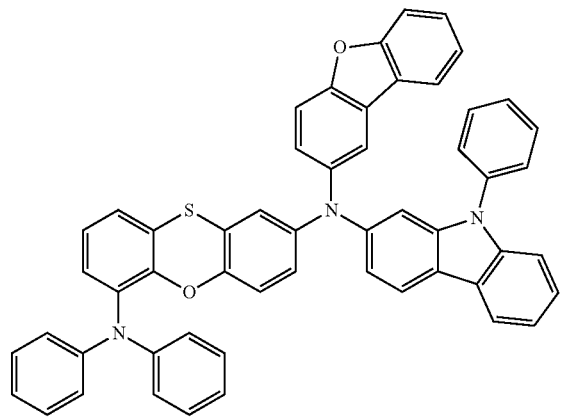
P-89
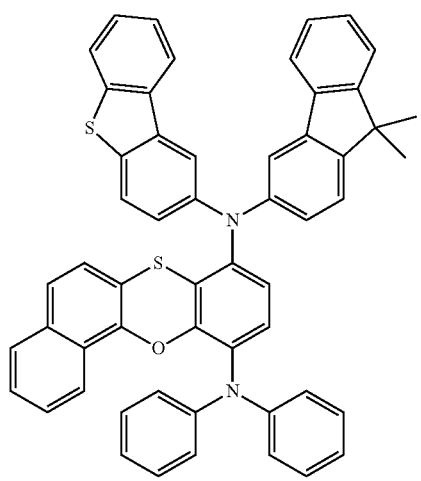
P-90
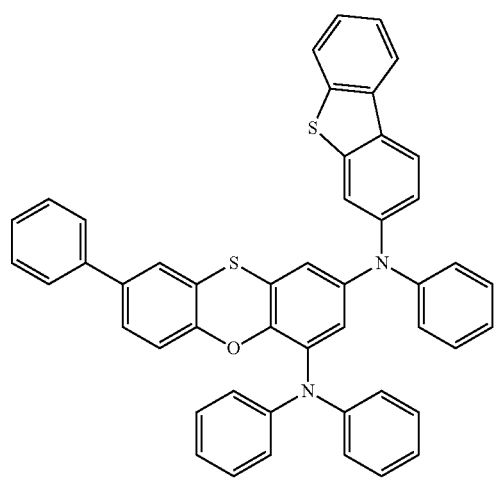
P-91
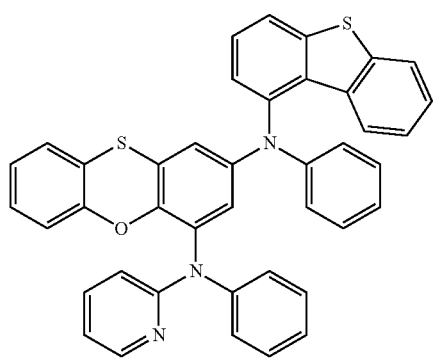
P-92
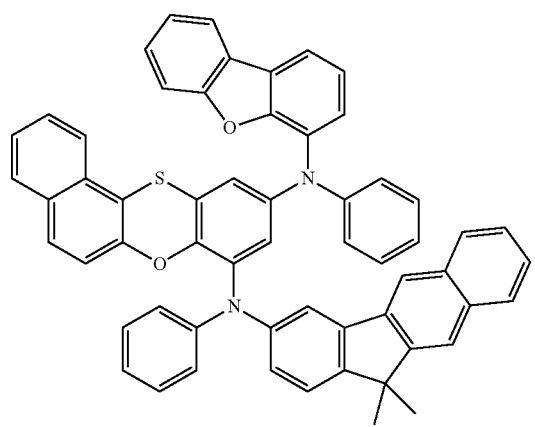

-continued
P-93
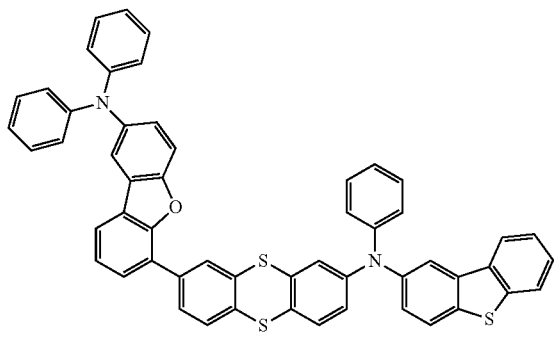
P-94
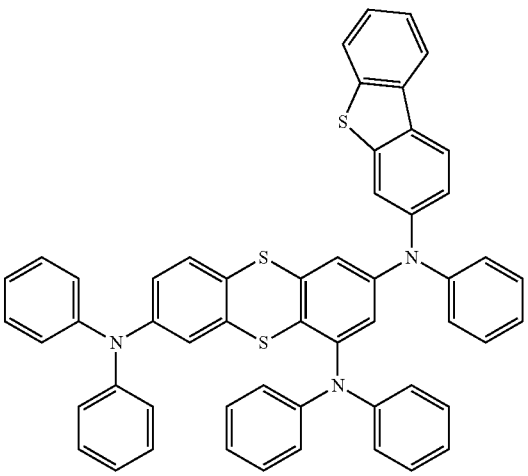
P-95
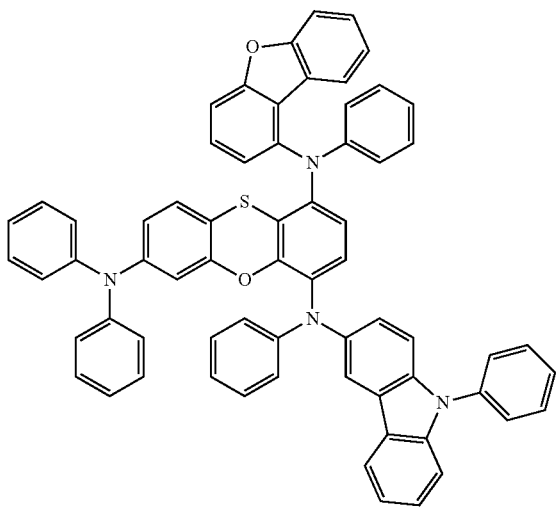
P-96
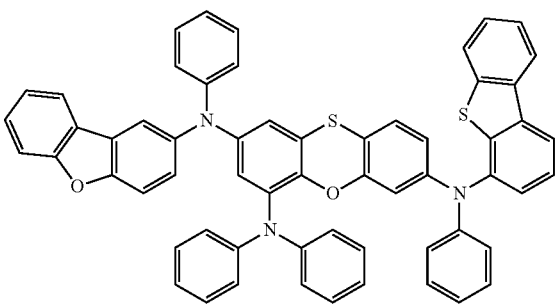
P-97
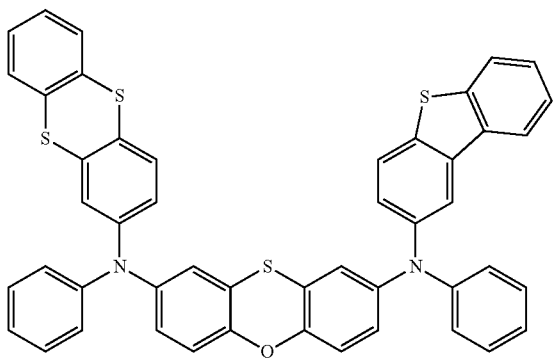
P-98
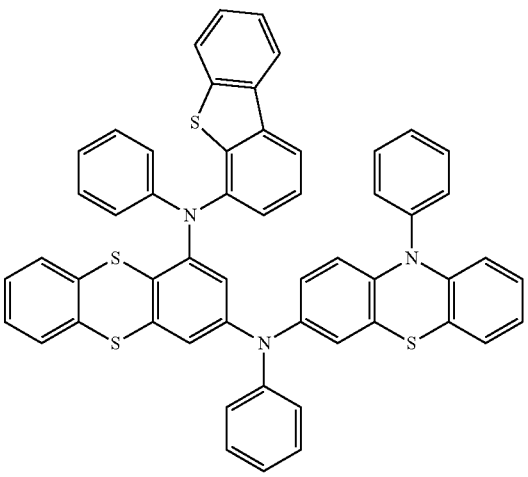

-continued
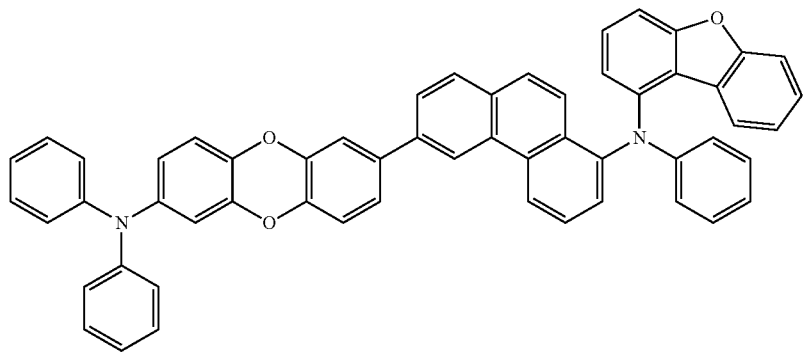
P-99
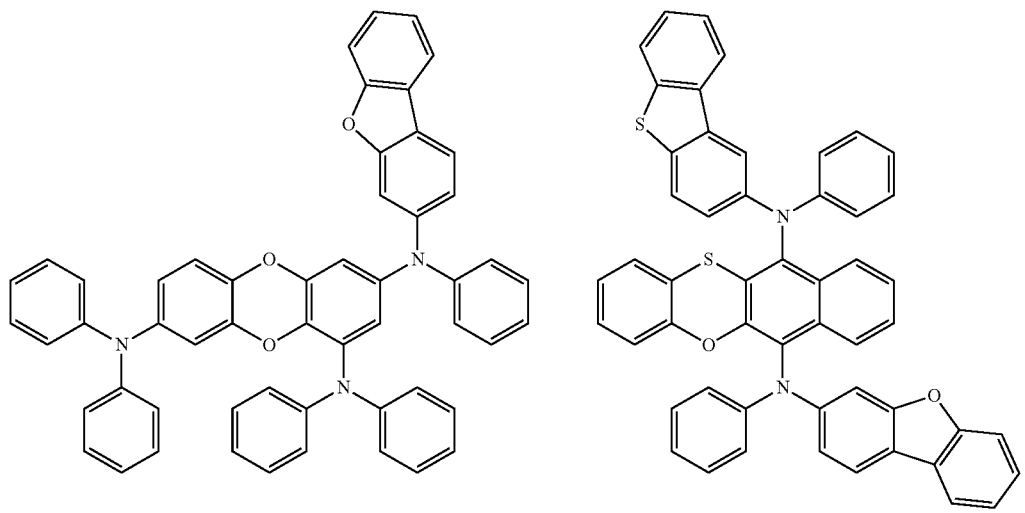
P-100  P-101
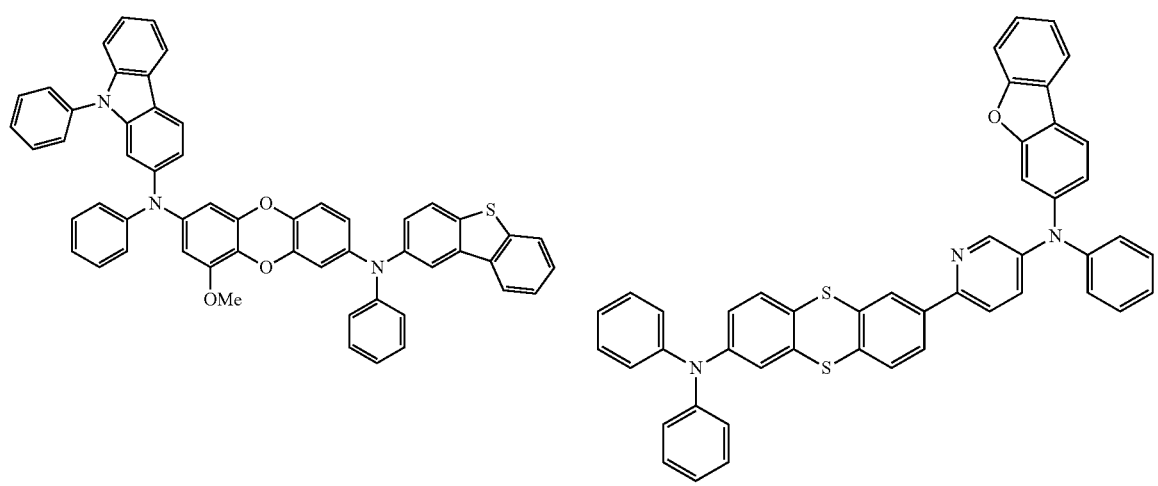
P-102  P-103

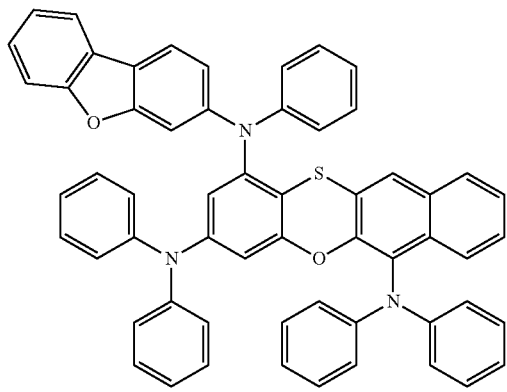

P-104

5. An organic electric element comprising a first electrode, a second electrode, and an organic material layer formed between the first electrode and the second electrode, wherein the organic material layer comprises compound represented by Formula 1 of claim 1.

6. The organic electric element of claim 5, wherein the organic material layer comprises at least one of a hole injection layer, a hole transport layer, an emission-auxiliary layer, a light emitting layer, an electron transport-auxiliary layer, an electron transport layer and an electron injection layer.

7. The organic electric element of claim 6, wherein the compound is comprised in the emission-auxiliary layer.

8. An electronic device comprising a display device and a control unit for driving the display device, wherein the display device comprises the organic electric element of claim 5.

9. The electronic device of claim 8, wherein the organic electric element is selected from the group consisting of an organic electroluminescent element, an organic solar cell, an organic photo conductor, an organic transistor, an element for monochromatic illumination and a quantum dot display.

* * * * *